(12) United States Patent
Hicks et al.

(10) Patent No.: US 10,782,238 B2
(45) Date of Patent: *Sep. 22, 2020

(54) DEVICE INCLUDING A POLYMERIC MATERIAL FOR DETECTING SPECIES AND STIMULUS AND METHOD OF USING THEREOF

(71) Applicants: Smith & Nephew PLC, Watford, Hertfordshire (GB); University of Sheffield, Sheffield (GB)

(72) Inventors: John Kenneth Hicks, York (GB); Stephen Rimmer, Sheffield (GB); Richard Hoskins, York (GB); Dorothy McCulloch, York (GB)

(73) Assignees: Smith & Nephew PLC, Watford (GB); University of Sheffield, Sheffield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/325,076

(22) PCT Filed: Jul. 3, 2015

(86) PCT No.: PCT/EP2015/065227
§ 371 (c)(1),
(2) Date: Jan. 9, 2017

(87) PCT Pub. No.: WO2016/012219
PCT Pub. Date: Jan. 28, 2016

(65) Prior Publication Data
US 2017/0234802 A1    Aug. 17, 2017

(30) Foreign Application Priority Data

Jul. 10, 2014 (GB) .................... 1412332.7
Jul. 10, 2014 (GB) .................... 1412345.9
Jul. 10, 2014 (GB) .................... 1412427.5
Apr. 16, 2015 (GB) .................... 1506451.2
Apr. 16, 2015 (GB) .................... 1506453.8
Apr. 16, 2015 (GB) .................... 1506463.7

(51) Int. Cl.
*G01N 21/78* (2006.01)
*G01N 21/77* (2006.01)
(Continued)

(52) U.S. Cl.
CPC ............. *G01N 21/78* (2013.01); *A61L 15/26* (2013.01); *A61L 15/425* (2013.01); *A61L 15/58* (2013.01); *C08F 220/56* (2013.01); *C08G 18/10* (2013.01); *C08G 18/42* (2013.01); *C08G 18/4277* (2013.01); *C08G 18/44* (2013.01); *C08G 18/48* (2013.01); *C08G 18/4833* (2013.01); *C08G 18/4854* (2013.01); *C08G 18/73* (2013.01); *C08G 18/758* (2013.01); *C08G 18/7614* (2013.01); *C08G 18/7621* (2013.01); *C08G 18/7671* (2013.01); *C08G 18/7678* (2013.01); *C08K 3/00* (2013.01); *C08L 33/26* (2013.01); *C08L 75/02* (2013.01); *C12Q 1/18* (2013.01); *G01N 21/77* (2013.01); *G01N 33/56911* (2013.01); *G01N 33/56938* (2013.01); *C08G 2101/00* (2013.01); *C08G 2101/0091* (2013.01); *C08G 2270/00* (2013.01); *C08K 2003/2227* (2013.01); *C08L 75/04* (2013.01);
(Continued)

(58) Field of Classification Search
None
See application file for complete search history.

(56) References Cited

U.S. PATENT DOCUMENTS 2,249,867 A    7/1941 Snelling
3,675,654 A    7/1972 Baker et al.
(Continued)

FOREIGN PATENT DOCUMENTS

AU    2003204827    5/2006
CN    100484501    5/2009
(Continued)

OTHER PUBLICATIONS

Reddy et al. 2008 (Synthesis and Characterization of Semi-Interpenetrating Polymer Networks based on Polyurethane and N-isopropylacrylamide for Wound Dressing; Journal of Biomedical Materials Research Part B: Applied Biomaterials; 32-40). (Year: 2008).*

(Continued)

Primary Examiner — Mary Maille Lyons
(74) Attorney, Agent, or Firm — Knobbe, Martens, Olson & Bear LLP

(57) ABSTRACT

A device for sensing and/or detecting species or stimulus at a locus, preferably at a fluid or moist locus by means of fluid communication therewith, comprising a surface configured to contact the locus, wherein the surface comprises a polyurethane material which material comprises a polyurethane polymer network having a hydrophilic polymer immobilised therein wherein the hydrophilic polymer comprises immobilised therein a ligand or moiety for detecting or sensing species or stimulus and an indicator for indicating detection or sensing prior to contact with the locus and change in indication as a function of species or stimulus present at the locus wherein species or stimulus are selected from chemical and biological species or stimulus; the use thereof preferably for detecting and/or sensing or binding bacteria, or for detecting or sensing pH or for detection or scanning with use of a reader; and a Kit.

23 Claims, 11 Drawing Sheets

(51) Int. Cl.

| | |
|---|---|
| *A61L 15/26* | (2006.01) |
| *A61L 15/42* | (2006.01) |
| *A61L 15/58* | (2006.01) |
| *C08G 18/10* | (2006.01) |
| *C08G 18/73* | (2006.01) |
| *C08G 18/75* | (2006.01) |
| *C08G 18/76* | (2006.01) |
| *C08G 18/48* | (2006.01) |
| *C08G 18/42* | (2006.01) |
| *C08G 18/44* | (2006.01) |
| *C08K 3/00* | (2018.01) |
| *C08L 33/26* | (2006.01) |
| *C08L 75/02* | (2006.01) |
| *C12Q 1/18* | (2006.01) |
| *C08F 220/56* | (2006.01) |
| *G01N 33/569* | (2006.01) |
| C08L 75/04 | (2006.01) |
| C08K 3/22 | (2006.01) |
| C08G 101/00 | (2006.01) |

(52) U.S. Cl.
CPC ...... *C08L 2205/04* (2013.01); *G01N 2333/21* (2013.01); *G01N 2333/31* (2013.01); *G01N 2800/26* (2013.01)

(56) References Cited

U.S. PATENT DOCUMENTS

| | | |
|---|---|---|
| 3,759,261 A | 9/1973 | Wang |
| 4,029,598 A | 6/1977 | Neisius et al. |
| 4,192,311 A | 3/1980 | Felfoldi |
| 4,382,380 A | 5/1983 | Martin |
| 4,705,513 A | 11/1987 | Sheldon et al. |
| 4,728,499 A | 3/1988 | Fehder |
| 4,813,942 A | 3/1989 | Alvarez |
| 4,885,077 A * | 12/1989 | Karakelle ............. G01N 27/40 204/403.06 |
| 4,999,306 A | 3/1991 | Yafuso et al. |
| 5,104,660 A | 4/1992 | Chvapil et al. |
| 5,181,905 A | 1/1993 | Flam |
| 5,277,872 A | 1/1994 | Bankert et al. |
| 5,536,783 A | 7/1996 | Olstein et al. |
| 5,571,684 A | 11/1996 | Lawrence et al. |
| 5,690,624 A | 11/1997 | Sasaki et al. |
| 5,766,212 A | 6/1998 | Jitoe et al. |
| 5,788,687 A | 8/1998 | Batich et al. |
| 5,852,126 A | 12/1998 | Barnard et al. |
| 5,853,669 A | 12/1998 | Wolfbeis |
| 5,897,516 A | 4/1999 | Kadash et al. |
| 6,120,904 A | 9/2000 | Hostettler et al. |
| 6,284,942 B1 | 9/2001 | Rabin |
| 6,333,093 B1 | 12/2001 | Burrell et al. |
| 6,388,043 B1 | 5/2002 | Langer et al. |
| 6,482,491 B1 | 11/2002 | Samuelsen et al. |
| 6,617,488 B1 | 9/2003 | Springer et al. |
| 6,688,525 B1 | 2/2004 | Nelson et al. |
| 6,696,240 B1 | 2/2004 | Kloepfer et al. |
| 6,747,185 B2 | 6/2004 | Inoue et al. |
| 6,772,708 B2 | 8/2004 | Klofta et al. |
| 6,815,207 B2 | 11/2004 | Yabuki et al. |
| 7,159,532 B2 | 1/2007 | Klofta et al. |
| 7,605,298 B2 | 10/2009 | Bechert et al. |
| 7,622,629 B2 | 11/2009 | Aail |
| 7,749,531 B2 | 7/2010 | Booher |
| 7,777,092 B2 | 8/2010 | Lykke et al. |
| 7,873,141 B2 | 1/2011 | Imai et al. |
| 8,372,049 B2 | 2/2013 | Jaeb et al. |
| 8,425,996 B2 | 4/2013 | Gorski et al. |
| 8,791,315 B2 | 7/2014 | Lattimore et al. |
| 8,795,257 B2 | 8/2014 | Coulthard et al. |
| 8,896,706 B2 | 11/2014 | van Den Hengel et al. |
| 8,927,801 B2 | 1/2015 | Klofta |
| 8,997,682 B1 | 4/2015 | Ashcroft |
| 9,311,520 B2 | 4/2016 | Burg et al. |
| 9,445,749 B2 | 9/2016 | Erickson et al. |
| 9,504,421 B2 | 11/2016 | Greener |
| 9,829,471 B2 | 11/2017 | Hammond et al. |
| 10,053,532 B2 | 8/2018 | Hanson et al. |
| 2002/0062114 A1 | 5/2002 | Murai et al. |
| 2002/0091347 A1 | 7/2002 | Eakin |
| 2004/0044299 A1 | 3/2004 | Utsugi |
| 2004/0133090 A1 | 7/2004 | Dostoinov et al. |
| 2005/0105789 A1 | 5/2005 | Isaacs et al. |
| 2005/0187146 A1 | 8/2005 | Helmus et al. |
| 2005/0199055 A1 | 9/2005 | Browne |
| 2006/0140999 A1 | 6/2006 | Lendlein et al. |
| 2007/0003606 A1 * | 1/2007 | Booher ............. A61B 5/14539 424/448 |
| 2007/0048224 A1 | 3/2007 | Howell et al. |
| 2007/0129784 A1 | 6/2007 | Lendlein et al. |
| 2007/0142762 A1 | 6/2007 | Kaplan et al. |
| 2007/0188759 A1 | 8/2007 | Mehendale et al. |
| 2007/0225663 A1 | 9/2007 | Watt et al. |
| 2007/0270774 A1 | 11/2007 | Bergman et al. |
| 2007/0276207 A1 | 11/2007 | Eagland et al. |
| 2008/0021166 A1 | 1/2008 | Tong et al. |
| 2008/0208151 A1 | 8/2008 | Zacharias et al. |
| 2009/0062757 A1 | 3/2009 | Long et al. |
| 2009/0157024 A1 | 6/2009 | Song |
| 2009/0190135 A1 * | 7/2009 | Clarizia ............. C12N 5/0068 356/432 |
| 2009/0198167 A1 | 8/2009 | Ambrosio |
| 2009/0216168 A1 | 8/2009 | Eckstein et al. |
| 2009/0221977 A1 | 9/2009 | Blott et al. |
| 2010/0041968 A1 | 2/2010 | Meschisen et al. |
| 2010/0069838 A1 | 3/2010 | Weber et al. |
| 2010/0112680 A1 | 5/2010 | Brockwell et al. |
| 2010/0168695 A1 | 7/2010 | Robles et al. |
| 2010/0168700 A1 | 7/2010 | Schmidt et al. |
| 2010/0178203 A1 | 7/2010 | Kane et al. |
| 2011/0274593 A1 | 11/2011 | Gorski et al. |
| 2012/0123220 A1 | 5/2012 | Iyer et al. |
| 2012/0201437 A1 | 8/2012 | Ohnemus |
| 2012/0215190 A1 | 8/2012 | Kawashima |
| 2012/0256750 A1 | 10/2012 | Novak |
| 2012/0264163 A1 | 10/2012 | Booher |
| 2012/0279101 A1 | 11/2012 | Pretsch et al. |
| 2012/0323274 A1 | 12/2012 | Lendlein et al. |
| 2013/0066285 A1 | 3/2013 | Locke et al. |
| 2013/0066289 A1 | 3/2013 | Song et al. |
| 2013/0087298 A1 | 4/2013 | Phillips et al. |
| 2013/0131621 A1 | 5/2013 | Van Holten et al. |
| 2013/0303865 A1 | 11/2013 | Rebec et al. |
| 2014/0098209 A1 | 4/2014 | Neff |
| 2014/0121487 A1 | 5/2014 | Faybishenko et al. |
| 2014/0138441 A1 | 5/2014 | Davalos et al. |
| 2014/0154789 A1 | 6/2014 | Polwart et al. |
| 2014/0296808 A1 | 10/2014 | Curran et al. |
| 2015/0055134 A1 | 2/2015 | Papautsky et al. |
| 2015/0080685 A1 | 3/2015 | Markle et al. |
| 2015/0246995 A1 | 9/2015 | Hanson et al. |
| 2015/0265743 A1 | 9/2015 | Hanson et al. |
| 2015/0351970 A1 | 12/2015 | Dagger et al. |
| 2016/0100987 A1 | 4/2016 | Hartwell et al. |
| 2016/0262672 A1 | 9/2016 | Hammond et al. |
| 2016/0346421 A1 | 12/2016 | Courage et al. |
| 2017/0000407 A1 | 1/2017 | Saxby et al. |
| 2018/0196021 A1 | 7/2018 | Hammond et al. |

FOREIGN PATENT DOCUMENTS

| | | |
|---|---|---|
| CN | 101453969 | 6/2009 |
| CN | 101490556 | 7/2009 |
| CN | 201414880 | 3/2010 |
| CN | 101894212 | 11/2010 |
| CN | 102879393 | 1/2013 |
| CN | 103217503 | 7/2013 |
| EP | 0 340 018 | 11/1989 |
| EP | 0 430 608 | 6/1991 |
| GB | 905040 | 9/1962 |
| GB | 1255395 | 12/1971 |
| JP | S54-176283 | 12/1979 |

(56) References Cited

FOREIGN PATENT DOCUMENTS

| | | |
|---|---|---|
| JP | S57-162304 | 10/1982 |
| JP | H07-055788 | 3/1995 |
| JP | 2002-165757 | 6/2002 |
| JP | 2006-338521 | 12/2006 |
| JP | 2007-163350 | 6/2007 |
| JP | 2012-157438 | 8/2012 |
| KR | 10 2006 01331 | 12/2006 |
| KR | 20120059006 | 6/2012 |
| RU | 114854 | 4/2012 |
| WO | WO 1983/00742 | 3/1983 |
| WO | WO 1998/12996 | 4/1998 |
| WO | WO 1999/12581 | 3/1999 |
| WO | WO 2002/047737 | 6/2002 |
| WO | WO 2005/052572 | 6/2005 |
| WO | WO 2006/042871 | 4/2006 |
| WO | WO 2006/110502 | 10/2006 |
| WO | WO 2006/133430 | 12/2006 |
| WO | WO 2008/125995 | 10/2008 |
| WO | WO 2011/098575 | 8/2011 |
| WO | WO 2012/074509 | 6/2012 |
| WO | WO 2012/131386 | 10/2012 |
| WO | WO 2013/074509 | 5/2013 |
| WO | WO 2014/066913 | 5/2014 |
| WO | WO 2014/113770 | 7/2014 |
| WO | WO 2016/012219 | 1/2016 |

OTHER PUBLICATIONS

Reddy et al. 2008 (Synthesis and Characterization of Semi-Interpenetrating Polymer Networks Based on Polurethane and N-isopropylacrylamide for Wound Dressing; Journal of Biomedical Materials Research Part B: Applied Biomaterials; 2008: 42-40) (Year: 2008).*

International Search Report and Written Opinion, re PCT Application No. PCT/EP2015/065227, dated Apr. 11, 2016.

International Preliminary Report on Patentability, re PCT Application No. PCT/EP2015/065227, dated Jan. 19, 2017.

Chen et al., "A PNIPAM-based fluorescent nanothermometer with ratiometric readout", Chemical Communications, vol. 47, No. 3, Nov. 26, 2010 pp. 994-996.

Reddy et al., "Synthesis and characterization of semi-interpenetrating polymer networks based on polyurethane and N-isopropylacrylamide for wound dressing", Journal of Biomedical Materials Research Part B: Applied Biomaterials, vol. 88B, No. 1, Sep. 8, 2008, pp. 32-40.

Uchiyama et al., "Fluorescent molecular thermometers based on polymers showing temperature-induced phase transitions and labeled with polarity-responsive benzofurazans", Analytical Chemistry, Amercial Chemical Society, vol. 75, No. 21, Oct. 4, 2003, pp. 5926-5935.

Loh, B.Y. et al., "Automated Mobile pH Reader on a Camera Phone", IAENG International Journal of Computer Science, vol. 38(3), Aug. 2011, in 7 pages.

Trupp, S., "Development of pH-sensitive indicator dyes for the preparation of micro-patterned optical sensor layers", Sensors and Actuators B, vol. 150, Jul. 15, 2010, pp. 206-210, in 5 pages.

Dargaville, T. et al., "Sensors and imaging for wound healing: A review," Biosensors and Bioelectronics, vol. 41, Mar. 2013, pp. 30-42, in 13 pages.

Mohr, G. et al., "Design of acidochromic dyes for facile preparation of pH sensor layers", Anal Bioanal Chem, vol. 392, pp. 1411-1418, in 8 pp.

Cho, S.M. et al., "Thermo-sensitive hydrogels based on interpenetrating polymer networks made of poly(N-isopropylacrylamide) and polyurethane", Journal of Biomaterials Science, vol. 21 (8-9), 2010, pp. 1051-1068, in 18 pages.

* cited by examiner

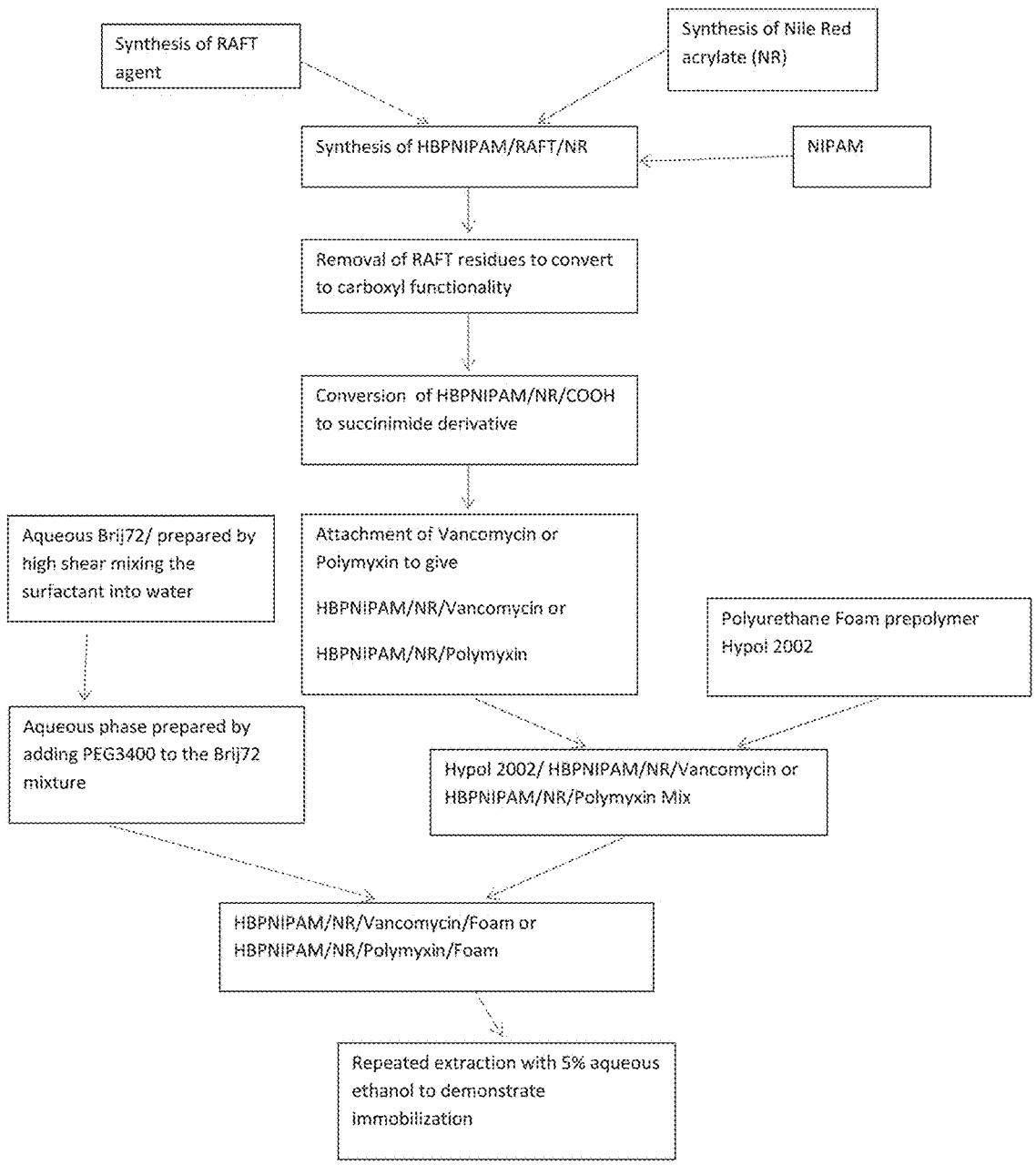
Figure 1.1

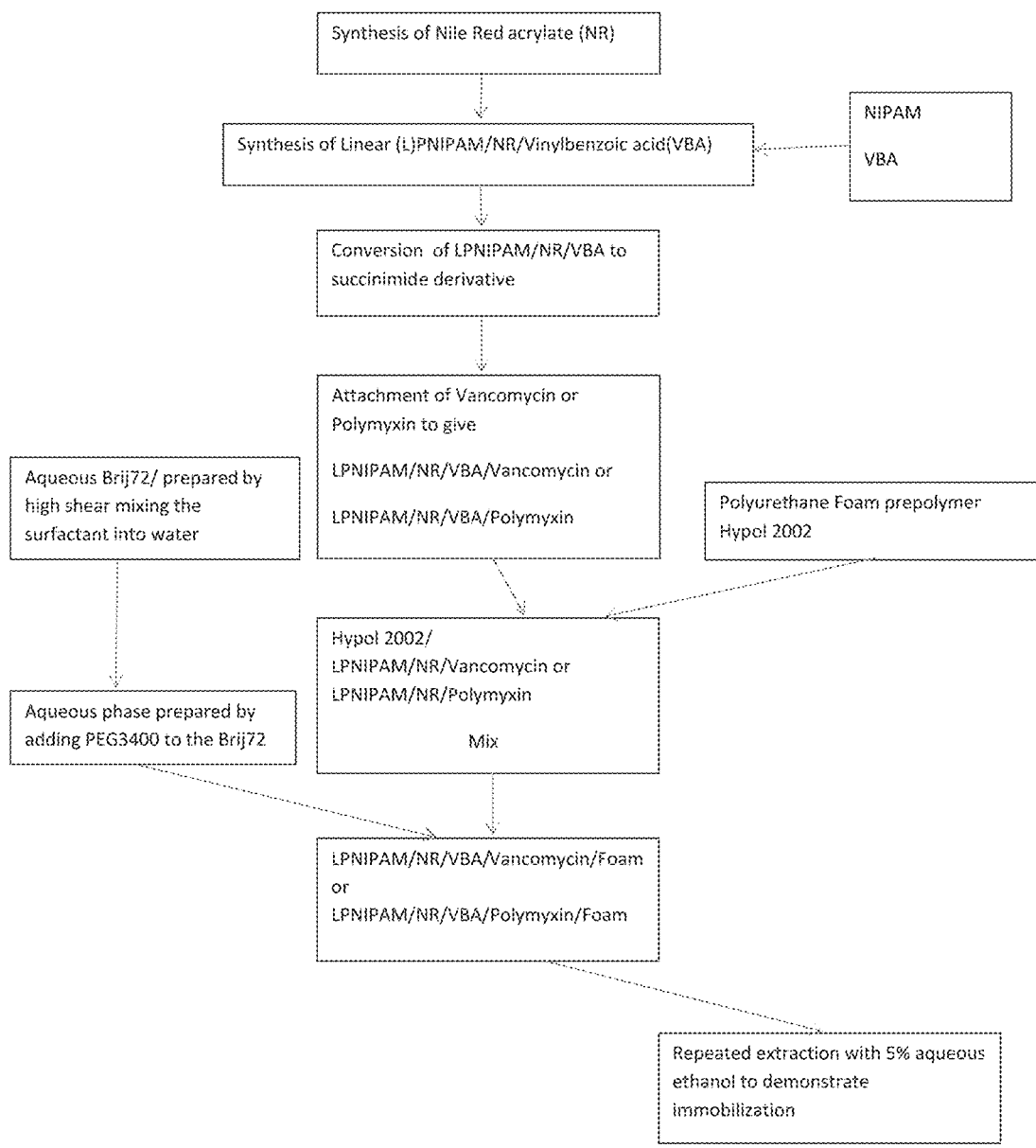
Figure 1.2

Figure 1.3 Synthesis of highly branched poly(N-isopropylacrylamide) and three step chain end modification to attach vancomycin. Stepwise from N-*isopropyl* acrylamide to highly branched Pyrrole ended polymer, Acid ended polymer, NHS-Succinimide ended polymer and then vancomycin (labelled as R) ended polymer.
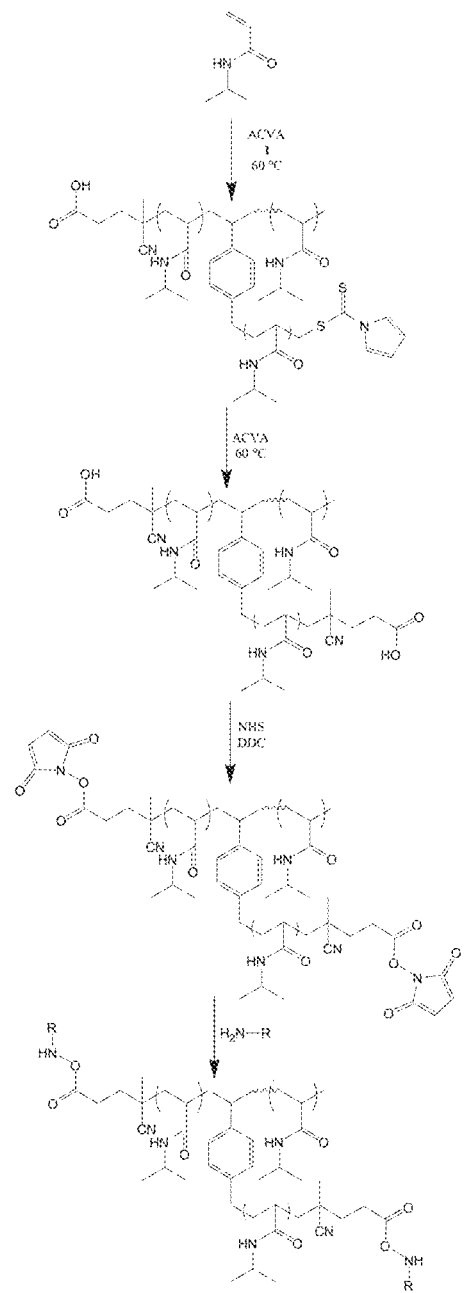

Shift in peak fluorescence emission wavelength poly(NIPAM-co-NRA-*block*-NIPAM) (black)

poly(NIPAM-*block*-NIPAM-co-NRA) (clear)

poly(NIPAM-co-NRA) (grey)

Figure 3.1 (a)
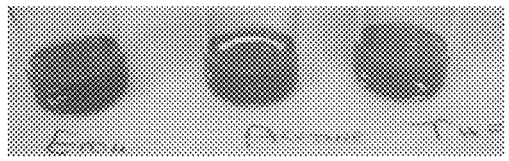
Sample 3.1.1 in ethanol, acetone and THF
Figure 3.1 (b)
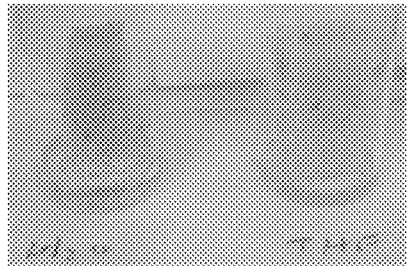
Sample 3.1.1 in deionised water and THF
Figure 3.2 Light microscope images of HBPNIPAM/Polymyxin copolymer foam 3.3.2
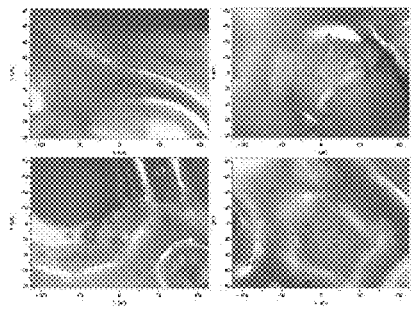
Fig 3.3
(a) 25:1 P-NIPAM/Van/NR 4%wt PU, washed 5x    (b) 25:1 P-NIPAM/van NR 10wt% PU, washed 5x
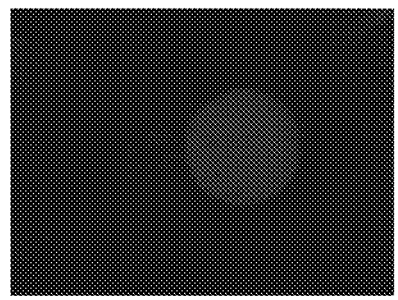 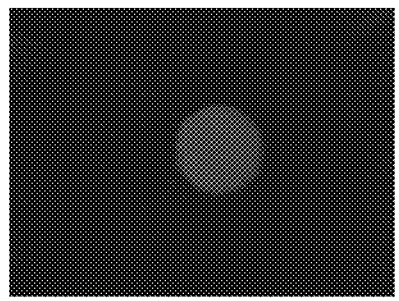

Figure 4.1 Distribution of polymer in foam
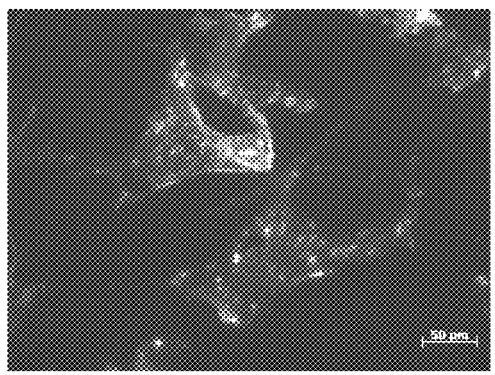
Figure 4.2.1
Figure 4.2.1 (a) cold (control)   Figure 4.2.1 (b) warm   Figure 4.2.1 (c) hot
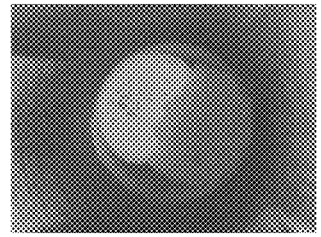 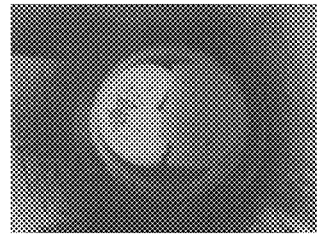 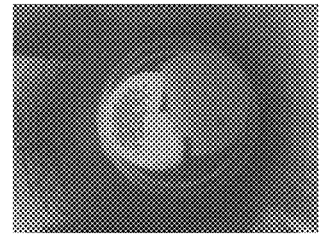
Figure 4.2.2 Fluorescent activity of dressing comprising polymer in PU foam supported on adhesive film
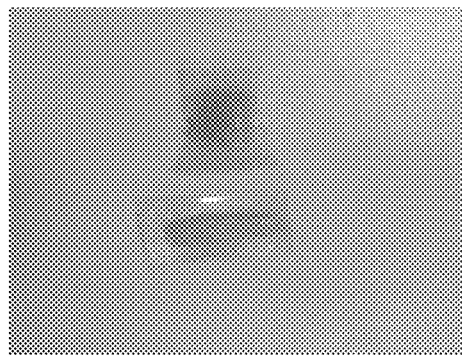 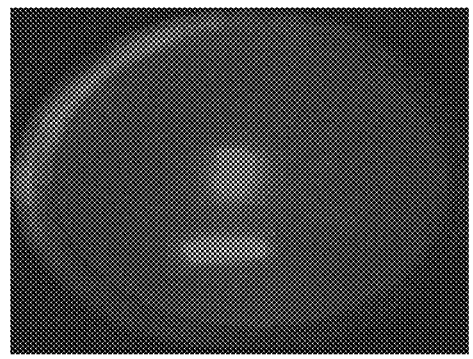

Figure 4.3
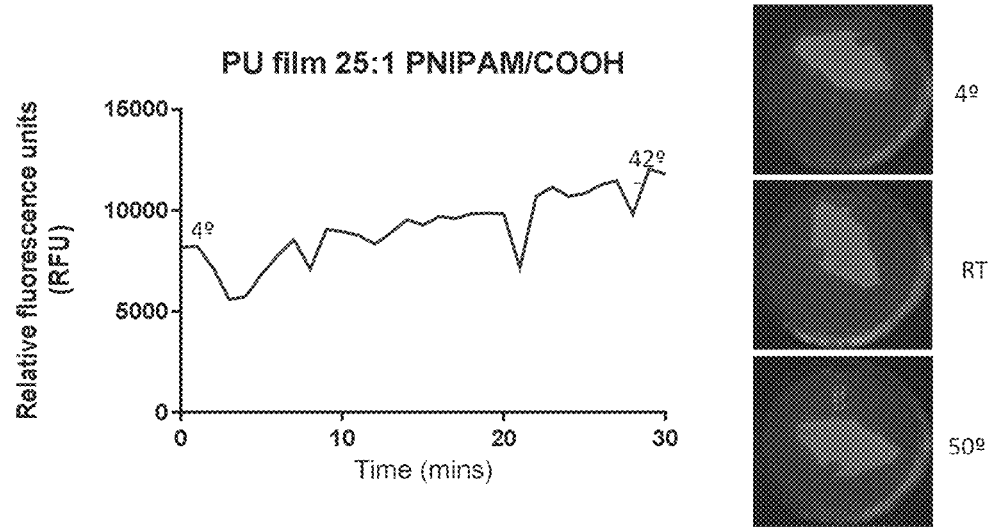
Figure 5.1 Selective Binding of bacteria (by gram type) by polymer in PU
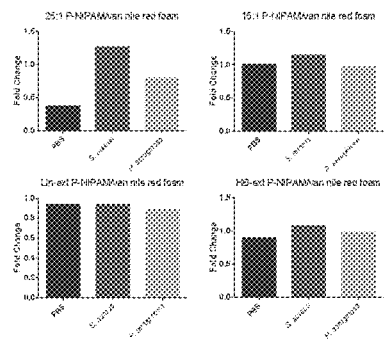

Figure 5.2 Bacterial Inhibition S. aureus (left: vancomycin; right : 25:1 P-NIPAM/van NR polymer)
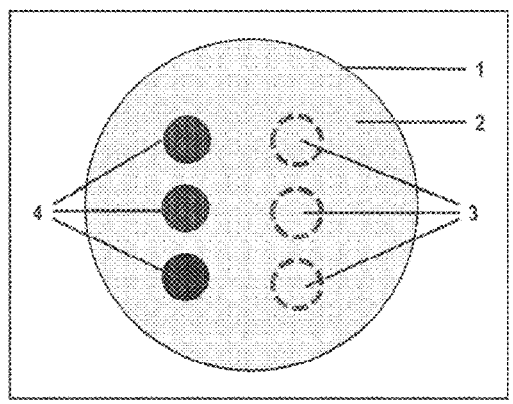
Figure 5.3 Bacterial recovery after binding
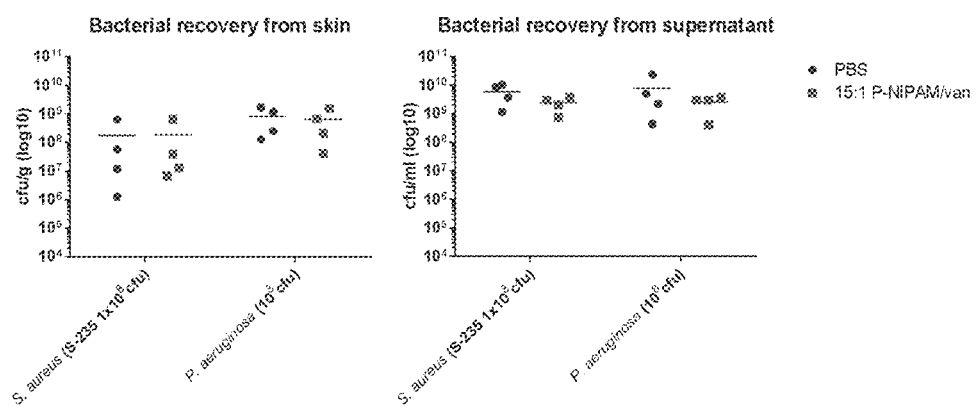

Figure 5.4
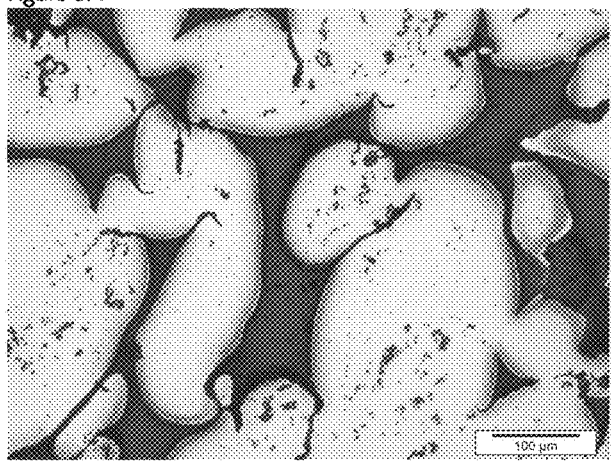
Figure 5.5.1 control foam with staph (100x)    Figure 5.5.2 Vancomycin foam in PBS (100x)
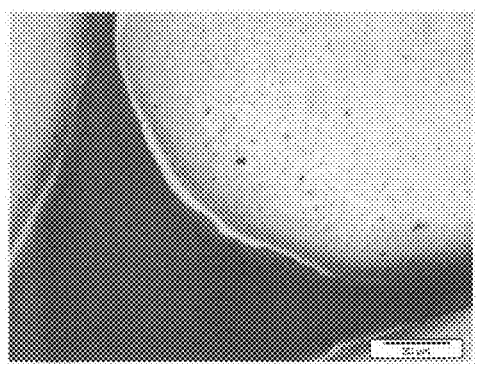 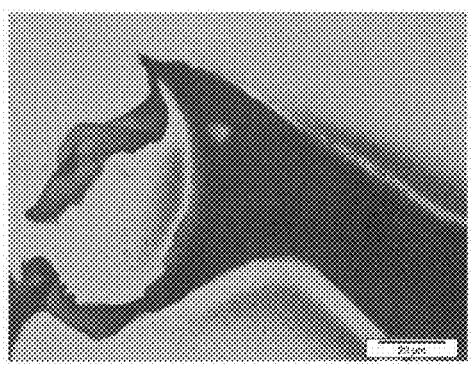
Figure 5.5.3    Vancomycin foam in PSA (100x) Figure 5.5.4  Vancomycin foam staph (100x)
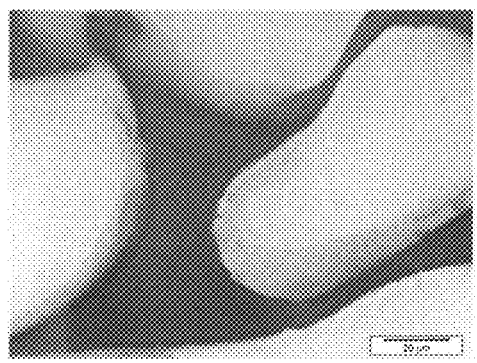 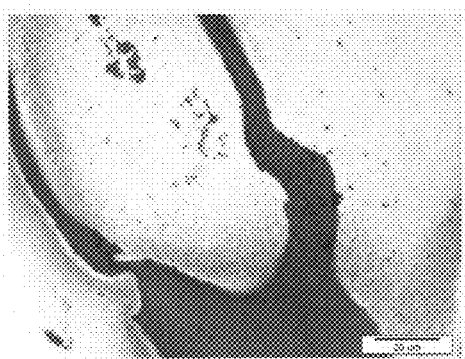

Figure 6.1
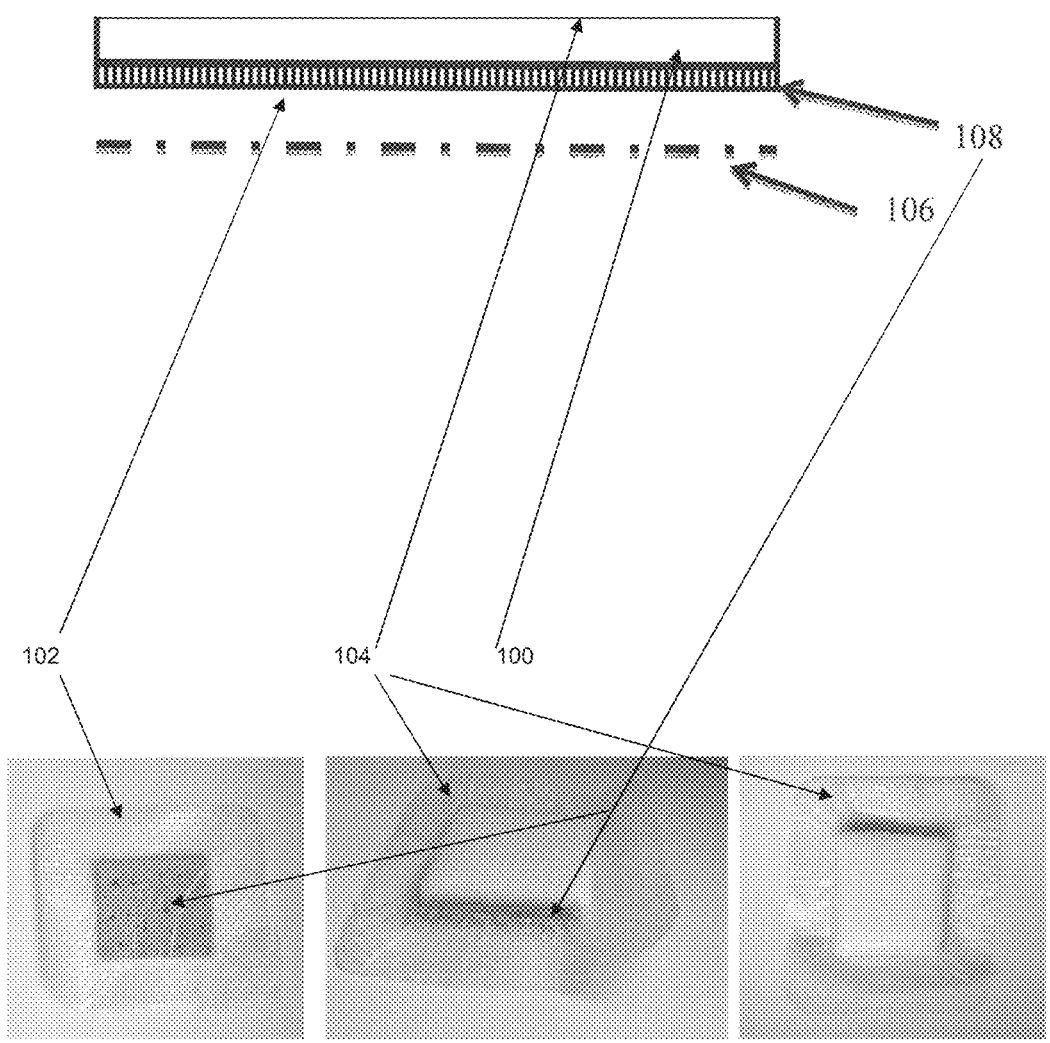
Figures 6.2.1 – 6.2.3

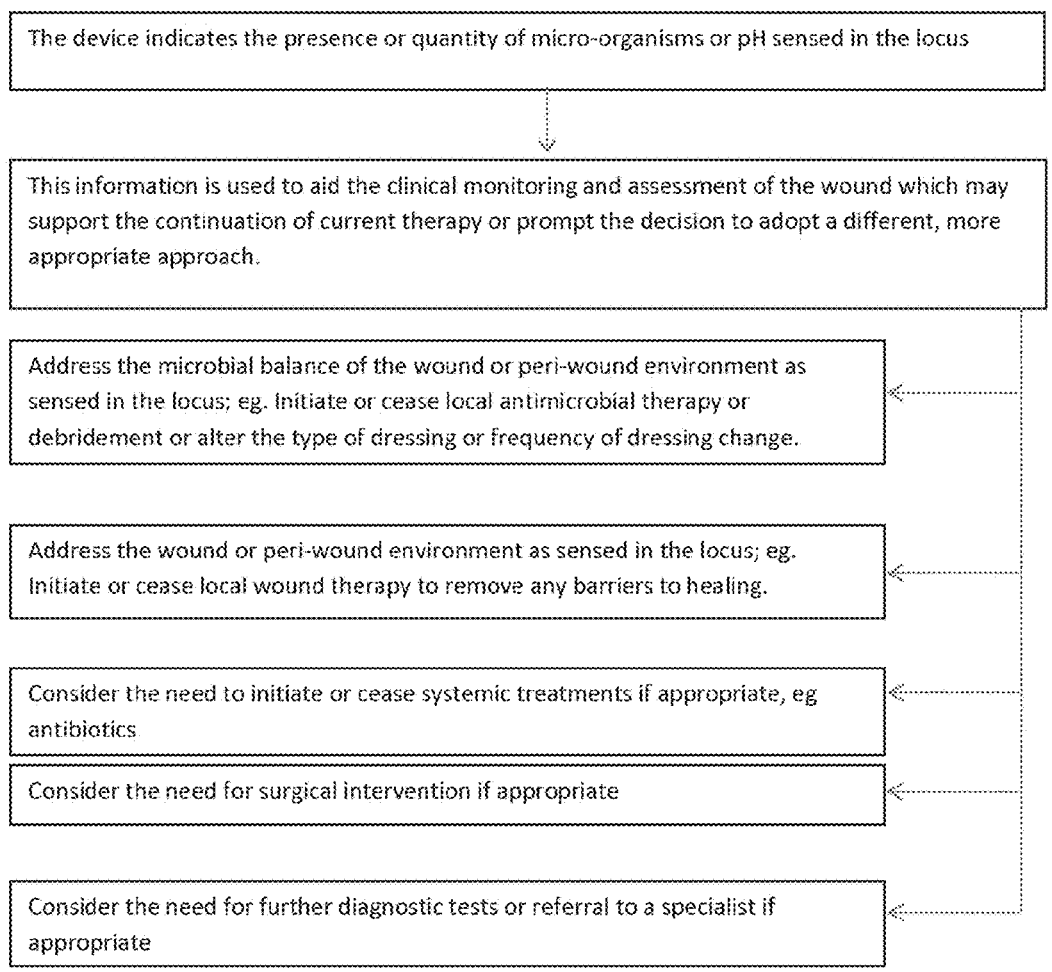
Figure 6.3 Flow scheme "use of device as indicator on wounds"

DEVICE INCLUDING A POLYMERIC MATERIAL FOR DETECTING SPECIES AND STIMULUS AND METHOD OF USING THEREOF

CROSS-REFERENCES TO RELATED APPLICATIONS

This application is a national stage application of International Patent Application No. PCT/EP2015/065227, filed on Jul. 3, 2015, titled "IMPROVEMENTS IN AND RELATING TO DEVICES," which claims priority to GB Patent Application No. GB1412345.9, filed Jul. 10, 2014, titled "IMPROVEMENTS IN AND RELATING TO DEVICES"; GB Patent Application No. GB1412427.5, filed Jul. 10, 2014, titled "IMPROVEMENTS IN AND RELATING TO POLYMER MATERIALS-I"; GB Patent Application No. GB 1412332.7, filed Jul. 10, 2014, titled "IMPROVEMENTS IN AND RELATING TO POLYMER MATERIALS-II"; GB Patent Application No. GB1506451.2, filed Apr. 16, 2015, titled "IMPROVEMENTS IN AND RELATING TO DEVICES"; GB Patent Application No. GB1506453.8, filed Apr. 16, 2015, titled "IMPROVEMENTS IN AND RELATING TO POLYMER MATERIALS-I"; and GB Patent Application No. GB1506463.7, filed Apr. 16, 2015, titled "IMPROVEMENTS IN AND RELATING TO POLYMER MATERIALS-II".

FIELD OF INVENTION

The present invention relates to a device for detecting or sensing chemical or biological species or stimulus including microbes such as bacteria or pH, in particular for sensing and/or assessing and/or detecting microbes at or in a locus or pH at a locus, a construct or wound dressing for the same, processes for their preparation, a device for interfacing therewith, methods for detecting and/or sensing chemical or biological species or stimulus including microbes such as bacteria or pH, associated methods for detecting microbes and/or pH, and their use for example in medical care, dental care, sanitation, point of use sterilisation, hygiene, personal care, biosurveillance or packaging.

More particularly the invention relates to the device for detecting microbes by type for example detecting bacteria by type selected from gram positive type bacteria, gram negative type bacteria and a combination thereof, or pH, a construct comprising a bacteria sensor, more particularly a bacteria sensing wound dressing or wipe or part thereof or pH sensor, processes, method for detecting bacteria or pH and use in wound management, sanitation applications and the like most particularly in wound care, including care of moderately and highly exuding chronic and acute wounds, in sterilisation, hygiene or sanitation including air conditioning, water sanitation and the like.

BACKGROUND

The field of wound care management has long understood that the pH of a wound can be an indication of wound healing status and can indicate when further action may be necessary to aid wound healing. The pH can affect many factors including oxygen release, angiogenesis, protease activity and bacterial toxicity. Acute and chronic wounds with an elevated alkaline pH have been shown to have lower rates of healing than wounds in which the pH is closer to neutral. For example, if a chronic wound has a pH of between 6 to 7.5 this indicates that wound healing is progressing well. In comparison, if the pH is between 7.5 and 8, this indicates that the wound should be monitored and a pH of above 8 indicates that clinical intervention is required. It is therefore important to be able to monitor wound pH in order to be able to assess wound healing and intervene, if necessary.

Wounds can become infected and there is no quick and easy way to determine if the bacteria present are gram negative or gram positive. At present any dressing would need to be removed and the wound inspected to determine if the wound is infected thus exposing the wound to further bacteria and potential complications. Invasive sampling such as by tissue biopsy, withdrawing a swab or wound fluid sample for testing, investigating pH by probe and the like is the usual means to confirm presence of infection.

Stimulus responsive polymers undergo a response event which drives the polymer through a phase change within a particular temperature range: the coil-to globule transition ($T_{c-g}$). The phase change may be observed directly or may be detected as a change in hydrophilicity or hydrophobicity of the polymer. The lower critical transition temperature (LCST) marks the transition temperature.

WO2010/094976 (Rimmer et al) discloses hyper branched, herein referred as highly branched, hydrophilic thermoresponsive polymers with bacteria binding functionality which can be used to remove infective bacteria from media such as wounds and biofluids. Thermoresponsive polymers belong to the general class of stimulus responsive polymers. These thermoresponsive polymers undergo a binding event on binding bacteria which drives the polymer through the $T_{c-g}$.

Adding bacteria-binding functionality to otherwise non-active polymeric devices and surfaces is an attractive proposition for enabling in situ identification of bacteria. However, in many instances simply mixing a functional polymer and non-active polymer material to produce blends produces material that is subject to leaching of the linear hydrophilic polymer. This occurs if the linear hydrophilic polymer is water-soluble whereby it can generally be extracted into an aqueous phase, precluding application from solution or use in the aqueous environment of a medical application. Therefore, in order to add such polymer to structural material used in medical devices it is necessary to prevent it from being leached.

Fully interpenetrating networks (F-IPN) are defined as a polymer comprising two or more crosslinked polymer networks characterized by the two or more crosslinked networks interpenetrating each other.

Such S-IPNs allow theoretical separation of network and polymer or macromolecule without breaking of bonds.

F-IPNs are of great utility in many sectors because they can provide materials with properties and functionality of both components. However F-IPNs are difficult to manufacture because it is often necessary to find either concurrent polymerisation processes that do not interfere with each other or to swell a preformed network with another monomer and then polymerise this polymer/monomer blend. The concurrent polymerisation route is only applicable to certain combinations of materials and the swelling approach can produce distortions of premolded devices.

On the other hand semi-interpenetrating networks (S-IPN) are materials that contain two polymer components. One of the polymer components is a crosslinked network and the other is not cross-linked. Within this definition both branched and linear polymers can comprise the non-cross-linked component. S-IPNS can be more easily manufactured by mixing in a macromolecule during the polymerisation and crosslinking of the network polymer.

However, most of the known semi-interpenetrating networks contain linear non-crosslinked components and semi-interpenetrating networks with soluble components designed to respond to the presence of infective species and are often used in contact with fluids that swell the crosslinked component whereby the linear component is easily extracted or is capable of leaching from the crosslinked component. Semi-IPNs composed of a brached or unbranched water soluble non-crosslinked component which is designed to be retained within the network on use are unknown.

There is therefore a need for a polymeric device comprising non-leachable bacteria binding polymer.

The present invention relates to the improvement of dressings with the use of S-IPNs wherein the functional hydrophilic polymer, more particularly the at least partly highly branched hydrophilic polymer as hereinbefore defined, is immobilised within a polyurethane polymer network. We have surprisingly found that the functional hydrophilic polymer as herein defined is not leached or extracted from the polyurethane polymer network.

There is therefore provided herein a device comprising a polyurethane material of a polyurethane network modified by the immobilisation therein of a hydrophilic polymer wherein the hydrophilic polymer comprises immobilised ligand or moiety for the detection or sensing of species or stimulus preferably in a fluid or moist environment or locus by means of fluid communication therewith, and comprising immobilised indicator for indicating detection or sensing wherein species are selected from acid and base groups and microbes.

Immobilised ligand or moiety is bound to the hydrophilic polymer in manner that it remains bound in a fluid environment.

Microbial species preferably include bacterial, such as type-specific bacterial, yeast or fungi. Acid and base groups are preferably indicative of pH for example of an environment or locus. The device is preferably for sensing or detecting species or stimulus by means of intimate contact therewith.

Polyurethanes/ureas may be formed by polymerisation of isocyanates and alcohols and/or water. Polyurethane networks such as chain extended or crosslinked polyurethanes may be formed by polymerisation of multi-functional alcohols with diisocyanates. We have now surprisingly found that hydrophilic bacteria-binding polymer may be immobilised in polyurethanes by mixing in during polyurethane polymerisation, more particularly during or prior to network formation such as during or prior to a chain extending step or a crosslinking step or during a step growth polymerisation step. A polyurethane network appears to grow in the presence of the highly branched hydrophilic polymer. The highly branched hydrophilic polymer appears to become entwined within, and penetrate, the network whereby it is unable to diffuse out of the polyurethane network.

Our finding has enabled the provision of a device and construct such as a bacterial sensor or detector, pH sensor or detector, bacterial sensing or detecting wound dressing and the like for species detection such as bacterial detection or pH detection comprising an indicator for indication of detection or sensing. For example the detection or sensing of bacteria or acid or base groups indicative of pH may be evidenced by visual inspection or scan in situ of the device or material such as a dressing cover layer or wound contact layer, for change in appearance thereof.

The device, construct and dressing provided herein comprise in novel manner a semi-IPN or entangled network composed of a brached or unbranched water soluble non-crosslinked component which is designed to be retained within the network on use.

Our finding has moreover enabled the provision of an inspection or scanning device or reader for inspecting or scanning or reading the detection device and displaying information relating to sensed or detected microbes such as bacteria or pH, for example for displaying an image or information relating thereto. The detection device is conveniently provided together with a separate or integral inspection or scanning strip providing reference information to facilitate generating output information relating to bacteria or pH. Our finding has moreover enabled the provision of a method for inspection or scanning.

With the current invention the wound dressing may not need to be removed to determine the type of bacteria (gram positive or gram negative) that is present and the amount present. This will be done either visually through a colour change of the dressing or by an optical reader. It may be necessary to remove opaque dressings and examine the wound facing side to determine the type of bacteria present either visually or by use of an optical reader. In addition as the bacteria are detected they may also be captured by the hydrophilic polymer thus removing them from the wound by capturing them in the dressing itself.

Microbial or microbes herein include bacterial or bacteria, yeast, fungal, fungus or fungi or combinations thereof. Reference hereinbelow to bacteria includes reference to microbes unless otherwise specifically indicated or unless the sense dictates otherwise.

In a particular advantage the polyurethane material is obtained in a simple manner that involves only blending of polymerisation components, preferably blending of hydrophilic polymer with reaction components during the polyurethane polymerisation reaction.

More particularly the hydrophilic polymer, for example the hydrophilic bacteria or pH detecting polymer, or bacteria-binding polymer, may be immobilised in polyurethanes by mixing in during the polymerisation reaction. More particularly the hydrophilic polymer appears to become entwined within, and penetrate, or entangled by, the network whereby it is unable to diffuse out of the polyurethane network.

Preferably the hydrophilic polymer comprises detection or sensing ligand or moiety and indicator for indication of detection or sensing. Preferably indication is by visual inspection or by scan in situ of the device for change in appearance thereof. Preferably the device enables quantification of bacteria or pH.

BRIEF DESCRIPTION OF THE INVENTION

In its broadest aspect or as hereinbefore defined there is provided a device for sensing and/or detecting species or stimulus at a locus, preferably at a fluid or moist locus or by means of fluid communication therewith,
  comprising a surface configured to contact the locus,
  wherein the surface comprises a polyurethane material which material comprises a polyurethane network having a hydrophilic polymer immobilised therein
  wherein the hydrophilic polymer comprises immobilised therein a ligand or moiety for detecting or sensing species or stimulus and an indicator for indicating detection or sensing prior to contact with the locus and change in indication as a function of species or stimulus present at the locus wherein species or stimulus are selected from chemical and biological species or stimulus.

More particularly there is provided a device for sensing and/or detecting species or stimulus at a locus, preferably at a fluid or moist locus by means of fluid communication therewith, comprising a surface configured to contact the locus, wherein the surface comprises a polyurethane material which material comprises a polyurethane polymer network having a hydrophilic polymer immobilised therein wherein the hydrophilic polymer comprises immobilised therein a ligand or moiety for detecting or sensing species or stimulus and an indicator wherein indicator provides a first indication prior to contact with the locus and changes indication as a function of species or stimulus present at the locus wherein species or stimulus are selected from chemical and biological species or stimulus.

Species are preferably selected from acid and base groups and microbes, preferably bacteria, yeast, fungus, and combinations thereof.

Stimulus is suitably selected from temperature, pH, ionic strength, hydrophilicity, polarity and species-response.

Suitably the device is also for assessing species or stimulus, such as microbes or pH at the locus. Preferably change in indication includes a change from a neutral first indication or from a first indication sensing or detecting species or stimulus.

Preferably the device is a device as hereinbefore defined having microbial or pH detecting function.

Preferably the device comprises in addition to the locus-contacting surface, an opposing non-locus contacting surface, wherein either surface or both provides a species or stimulus detection or sensing zone comprising a polyurethane material as hereinbefore defined.

Preferably either surface or both provides a microbe or pH detection or sensing zone comprising a polyurethane material as hereinbefore defined.

The surface may be a polyurethane material surface or the polyurethane material may be applied to a locus contacting surface. The surface may comprise polyurethane material at a face thereof configured to contact the locus or at an opposing face thereof.

The surface and/or the material is suitably fluid permeable at least on a locus contacting face thereof. The surface and/or the material may be fluid permeable throughout. The surface and/or material and/or device may be fluid impermeable at an opposing face thereof.

The device may be rigid or conformable. Preferably the device is conformable. The surface may be planar or shaped, preferably is planar for example is sheet-form. The device may be configured for immersing in a locus or applying to a surface of a locus. Preferably the device is for applying to a surface of a locus.

A locus as hereinbefore defined, which may comprise or be provided in an environment as hereinbelow referred, preferably comprises or contains or consists of fluid, in particular aqueous fluid including moisture and physiological fluids. The device is preferably configured to be in fluid communication with the locus. Preferably a locus is a moist locus such as an exuding locus. A device as hereinbefore defined may be activated by fluid contact.

In a first embodiment of the hereinbefore defined device, polyurethane material comprises a crosslinked polyurethane polymer network having a highly branched hydrophilic polymer or polymeric moiety immobilised therein, preferably a highly branched stimulus responsive hydrophilic polymer or moiety, more preferably which highly branched hydrophilic polymer or moiety is responsive to change in one or more of stimulus selected from temperature, pH, ionic strength, hydrophilicity and polarity, wherein such stimulus or change in stimulus is responsive to bacteria or pH at the locus.

Response to stimulus selected from temperature, pH and ionic strength may be induced or modified by one or more factors or by an environment at the locus selected from polar, and hydrophilic factors or environment and species conferring such factor or environment at or in fluid communication with the surface.

Preferably highly branched hydrophilic polymer responds at critical values of stimulus by transition from an open (solvated) coil to a collapsed state known as a globule, preferably wherein such transition comprises indication as hereinbefore defined.

Preferably indication of stimulus response of hydrophilic polymer provides quantification of binding as a function of concentration of detection or binding of bacteria.

In a second embodiment of the hereinbefore defined device, polyurethane material comprises a polyurethane polymer network having a linear or moderately branched hydrophilic polymer immobilised therein.

The hydrophilic polymer may be highly branched or linear or a part or moiety thereof may be highly branched and a part or moiety thereof may be branched or linear. A highly branched or linear polymer may incorporate a part or moiety which is moderately branched. Such part highly branched part linear hydrophilic polymers are referred herein as extended polymers. Extended hydrophilic polymers are obtained with a first polyurethane reaction step conducted in the presence of a first hydrophilic polymer, the reaction extended with use of a second polyurethane reaction step conducted in the presence of a second hydrophilic polymer.

Highly branched polymer is also termed hyper branched in the art, reference herein to highly branched polymer is to be taken as referring also to such hyper branched polymer.

Reference herein to hydrophilic polymer is to include highly branched hydrophilic polymer, moderately branched hydrophilic polymer, linear hydrophilic polymer or block copolymers thereof herein termed extended hydrophilic polymer unless indicated as only one or several thereof or unless the sense dictates only one or several thereof.

In a further aspect there is provided a novel hydrophilic polymer comprising ligand or species as herein defined comprising at least one block copolymer of a highly branched hydrophilic polymer and a linear hydrophilic polymer as herein defined. Preferably the block copolymer comprises a core block and an outer or peripheral block or blocks.

Preferably the block copolymer is characterised by its preparation wherein the core is prepared by the process for preparing one of highly branched and linear hydrophilic polymer and the process terminated and subsequently extended or recommenced following the process for preparing the other of highly branched and linear hydrophilic polymer. The polyurethane material may comprise one hydrophilic polymer or a plurality or blend thereof.

The LCST of the herein defined hydrophilic block polymers is dependent on the block architecture, in particular the architecture of the peripheral block. FIG. 2.1 shows shift in peak fluorescence emission wavelength (average mean of distribution) of vancomycin derived extended poly(NIPAM-co-NRA-block-NIPAM)(XBI, black), poly(NIPAM-block-NIPAM-co-NRA) (XBO, clear) samples compared to poly(NIPAM-co-NRA) (grey).

Accordingly a device comprising a plurality or blend of hydrophilic block copolymers is characterised by multiple LCST. Preferably LCST fall in a range with the branched-branched polymers having a much lower LCST than the branched-linear equivalents. The device is useful in detecting or sensing and quantifying species or stimulus.

In a further advantage a device comprising hydrophilic block copolymer providing a distribution of LCST provides for quantitative assessment of species or stimulus, wherein level of detected or sensed response is proportional to the amount of species or degree of proliferation thereof, or the degree of stimulus present.

Indicator may comprise a stimulus response as hereinbefore defined and/or hydrophilic polymer may be functionalised by attachment of indicator or indicating moiety. Indicator is preferably covalently bound to hydrophilic polymer. Preferably hydrophilic polymer or a moiety thereof is a copolymer of a hydrophilic monomer and an indicating monomer.

Device as hereinbefore defined suitably comprises hydrophilic polymer functionalised by attachment to said polymer of ligand or moieties possessing the facility to sense bacteria or pH. Preferably hydrophilic polymer is functionalised by covalently bound bacteria sensing or pH sensing ligand or moieties.

Preferably said ligand possesses the facility to sense bacteria by type selected from gram positive type bacteria, gram negative type bacteria and a combination thereof. Preferably the device provides a first indication prior to contact with the locus and changes indication as a function of bacteria at the locus. Preferably the device provides a change of indication as a function of detection, for example by binding, of bacteria present at the locus by type of bacteria.

Alternatively or additionally the device comprises hydrophilic polymer functionalised by attachment to said polymer of ligand or moieties such as functional groups possessing the facility to sense pH whereby the device provides a first indication prior to contact with the locus and changes indication as a function of the pH at the locus.

Preferably the device is functionalised by attachment to said hydrophilic polymer of indicator possessing the facility to provide indication on detection of or interaction with bacteria and/or by attachment to said polymer of ligand possessing the facility to sense bacteria.

Suitably ligand or moiety is immobilised on the device. The indicator or moiety remains immobilised in the presence of water and aqueous media at ambient temperature such as in the range 0-45 C, most particularly under physiological conditions.

In a particular advantage the device comprises bacteria-binding or bacteria detecting functionality added to otherwise non-active, in particular non-bacterially active or non antibiotic, devices, polymeric materials and surfaces for enabling in situ identification of bacteria.

Suitably the device comprises non-leachable bacteria detecting or sensing and/or binding ligand or moiety or non-leachable bacteria detecting function, more particularly comprises non-leachable bacteria detecting or sensing hydrophilic polymer.

Suitably the device comprises polyurethane material as structural material having hydrophilic polymer comprising bacteria binding or bacteria detecting or sensing ligand or moiety or functionality immobilised within the structural material in manner to prevent the hydrophilic polymer, and more particularly thereby the bacteria detecting or sensing or binding ligand or moiety or functionality or function comprised thereby, from being leached.

A device for sensing and/or assessing and/or detecting microbes such as bacteria, as hereinbefore defined, is not classified as an antibiotic device. Accordingly such device may be applied to an environment or a locus such as a wound site without the need for a prescription or other authority to medicate, in particular without the need for a prescription or other authority to apply antibiotic medication.

Preferably therefore such device is not intentionally antibiotic. Preferably the device, hydrophilic polymer and bacteria detecting or sensing ligand or moiety or functionality are configured to interact with live microbes such as bacteria in order to sense, assess or detect the presence thereof, however microbes such as bacteria remain live in contact with the device.

Preferably microbes such as bacteria are substantially unchanged by interaction with the device, at least in terms of antibiotic resistance. Without being limited to this theory it is thought that microbes such as bacteria are not disrupted by interaction with the device, at least to an extent that might induce antibiotic resistance, or are not violated or entered as a result of contact with the device, at least to an extent that might induce antibiotic resistance.

Preferably the device is not configured to release microbicide such as bactericideor antibiotic which might permanently interact with microbes or bacteria.

Preferably ligand comprises antibiotic modified or immobilised or both in manner to be devoid of antibiotic activity. Preferably the device is not classified as an antibiotic device nor contemplated as having the capacity to contribute to the risk of developing antibiotic resistance.

Hydrophilic polymer is immobilised within the polyurethane polymer network as hereinbefore defined. Suitably the indicator is immobilised on the hydrophilic polymer. Reference herein to immobilisation or to a hydrophilic polymer or indicator being immobilised within or by a component such as the polyurethane polymer network or the hydrophilic polymer is to its presence within or on that component and remaining within or on that component throughout the intended use or lifetime of the device or subject to the conditions of an intended locus for use thereof.

Preferably hydrophilic polymer and thereby indicator is distributed throughout the surface of the device. Hydrophilic polymer and thereby indicator are thus characterised by location at the surface of the device. Hydrophilic polymer and/or indicator may be associated with or may provide location information. Location information may for example be in the form of a device map. For example indicator may provide location information for indication or change of indication such as a device map of indication or change of indication. Suitably indicator is adapted to detect or sense species or ligand in the direct vicinity thereof.

Preferably hydrophilic polymer, ligand or moiety and/or indicator remain immobilised in the presence of water, aqueous media or physiological fluid and the like at ambient temperature such as in the range 0-45 C, most particularly under physiological conditions.

Immobilised hydrophilic polymer, ligand, moiety and/or indicator are thus retained within or on the device. Hydrophilic polymer, ligand, moiety and/or indicator are thus able to sense, detect or indicate bacteria present or pH at the device. Immobilised hydrophilic polymer, ligand, moiety and/or indicator may be retained at one or a plurality of zones within or on the device. Hydrophilic polymer, ligand, moiety and/or indicator are thus able to sense, detect or indicate bacteria or pH at the zone.

In a particular advantage the polyurethane material is obtained in a simple manner that involves only blending of hydrophilic polymer with polyurethane reaction components or polymerisation components.

Preferably therefore the hydrophilic polymer is immobilised within the network by introduction during the polymerisation reaction, which may be during formation of prepolymer or step growth of the polyurethane network whereby the hydrophilic polymer is present during the growth of the network, or during chain extension or crosslinking thereof.

BRIEF DESCRIPTION OF THE INVENTION

Immobilised hydrophilic polymer is conveniently introduced in the manner of a semi interpenetrating network (s-IPN) or entangled network with the polyurethane network, conveniently referred herein as an entrapped semi inter[enetrating network (es-IPN). Immobilised highly branched hydrophilic polymer such as for example stimulus-responsive polymer may be present in the form of a semi interpenetrating network (s-IPN or e s-IPN)) within the polyurethane network. Immobilised hydrophilic polymer which is moderately branched or linear or a combination thereof optionally with highly branched polymer may be present in the form of an entangled network with the polyurethane network.

Alternatively or additionally immobilised hydrophilic polymer may be subject to other bonding or polar or ionic attraction with the polyurethane network.

Immobilised hydrophilic polymer is that polymer remaining after generation of the polyurethane network, preferably after process work up, including subsequent processing steps such as isolation thereof from polymerisation medium and washing.

Effective immobilisation may conveniently be assessed for example by residual extraction in an aqueous solvent for the polymer.

In a particular advantage, immobilised hydrophilic polymer is retained within the polyurethane network under conditions including or selected from aqueous conditions, aqueous solvent conditions, such as physiological medium, and conditions for detection and/or binding of species including or selected from bacteria, acid or base conditions and the like.

The present invention relates to the improvement of S-IPNs in the form of the ES-IPN as hereinbefore defined wherein the highly branched hydrophilic polymer is entwined within and penetrated by the chain extended or crosslinked polyurethane polymer network and thereby entrapped therein. We have surprisingly found that the highly branched hydrophilic polymer as hereinbefore defined is separable from the penetrating network in theory only and not in practice and is not capable of leaching or of being extracted from the crosslinked polyurethane polymer network. Without being limited to this theory the highly branched hydrophilic polymer is not capable of diffusing through the network because the branch points can not diffuse past the crosslinks of the network. Alternatively or additionally some or all or part of the highly branched hydrophilic polymer forms bonds with the polyurethane, in the form of H-bonds, covalent bonds, grafts or other interactions. Bonds remain intact in the presence of aqueous solvent. Immobilisation of highly branched hydrophilic polymer may be the result of such bond formation or of entrapment by the penetrating network or both.

In the second embodiment the invention relates to the improvement of entangled networks as known in the art wherein a linear or moderately branched hydrophilic polymer is entangled by the chain extended or crosslinked polyurethane polymer network and thereby entrapped therein. We have surprisingly found that the linear or moderately branched hydrophilic polymer as hereinbefore defined is separable from the penetrating network in theory only and not in practice and is not capable of leaching or of being extracted from the polyurethane polymer network.

Without being limited to this theory the linear hydrophilic polymer is not capable of diffusing through the network because the polymer is entangled such that it can not diffuse out of the network. For example the polymer may be entangled or comprise internal steric factors or polar attractions such that it resembles a highly branched hydrophilic polymer and behaves in manner as hereinbefore defined for ES-IPNs.

We have surprisingly found that the hereinbefore and hereinbelow defined device does not release the entrapped or entangled hydrophilic polymer. Upon exhaustive washing in solvents effective for the copolymer, such as aqueous ethanol, ethanol, dichloromethane or acetone, the copolymer remains held in the polyurethane network, despite polarity, lipid effects, swelling or safety of the polyurethane network in said solvents. The copolymer is therefore held in manner such that it is resistant to removal by swelling of the surrounding polymer network, by solvent extraction or by solvation effects.

We have shown that the herein defined hydrophilic polymer is immobilized in the device with use of a range of solvents with differing degrees of polarity solvating power to attempt to remove the hydrophilic polymer from the polyurethane network. Solvents included:
water containing ethanol (5%),
dichloromethane (DCM),
acetone
ethanol and
DMSO.

DCM is the least polar and DMSO the most polar.

Solvents were selected from a consideration of the increasing solubility of the hydrophilic polymer with increasing solvent polarity. Solvents were further selected from a consideration of the ability of the solvent to swell the polyurethane material.

DMSO presents the solvent most likely to remove the material in view both of polarity and swelling of polyurethane material.

Polyurethane material was prepared for solvent extraction by work up to remove residual or low MW hydrophilic polymer entrained within the network.

Immobilised hydrophilic polymer was not leached from the polyurethane by any solvent.

Preferably therefore highly branched hydrophilic polymer is functionalised by attachment to said polymer of ligand possessing the facility to detect or sense microbes or pH, for example to detect or sense species or stimulus including microbes such as bacteria and acid or base groups and pH. Preferably hydrophilic polymer is functionalised by covalently bound bacteria sensing or pH sensing ligand or moieties.

More preferably polymer is highly functionalised by attachment of one or more ligands or moieties at a plurality or multitude of branches, preferably at the termini of said branches or at a plurality of positions along the hydrophilic polymer backbone and at the ends thereof. Preferred highly branched polymer adopts a fully solvated open coil structure below the LCST whereby ligands are highly exposed and available to take part in species binding or aggregation events. Preferably response to a change in stimulus as hereinbefore defined is induced by a species binding or aggregation event involving said ligand(s).

Herein microbial or microbes include bacterial or bacteria, yeast, fungal, fungus or fungi or combinations thereof. Reference hereinabove and hereinbelow to bacteria includes reference to microbes unless otherwise specifically indicated or unless the sense dictates otherwise.

The device may be rigid or conformable. Preferably the device is conformable.

Hydrophilic polymer comprises linear or highly branched hydrophilic polymer or a combination thereof. Preferably hydrophilic polymer is highly branched or comprises a highly branched moiety. A plurality of highly branched moieties may differ in polymer units or branching ratio or the like.

Highly branched hydrophilic polymer may be stimulus responsive hydrophilic polymer as hereinbefore defined. Preferably highly branched hydrophilic polymer comprises functionality for the detection and/or binding of species which induce a stimulus response. Response to stimulus selected from temperature, pH and ionic strength may be induced or modified by one or more factors or by an environment selected from polar, and hydrophilic factors or environment and species conferring such factor or environment on or in proximity of the device.

Highly branched hydrophilic polymer as hereinbefore defined such as poly(N-isopropylacrylamide) (PNIPAM or PIPAAm) preferably dissolve in aqueous media below a critical temperature, herein referred to as the lower critical solution temperature (LCST). As the temperature is raised above the LCST, the polymer forms primary particles which aggregate and then undergo sedimentation in the reaction vessel to form a solid mass. Such polymers having a temperature dependent solubility are known as thermoresponsive polymers and generically as stimulus responsive polymers.

The macroscopic changes that can occur at critical values of pH, temperature or ionic strength with such polymers come about because the polymer changes from an open (solvated) coil to a collapsed state known as a globule.

In a further advantage the stimulus response possesses the facility to be detected or monitored by means of the coil to globule transition. This enables for the first time the real time monitoring of species or factors which it is desired to detect or monitor with a useful device.

Any aqueous polymer solution will respond in this way to changes in pH, temperature or ionic strength but, for many systems, the critical points occur at temperatures that are above 100 C or below 0 C.

The highly branched stimulus responsive polymers defined herein respond to bacterial binding by passing through a desolvation driven transition in which the polymer passes from a fully solvated open coil to a desolvated globular structure. This desolvation of highly solvated ligands produces a large perturbation in the overall solvency of the polymer and this perturbation can produce significant decreases in its lower critical solution temperature (LCST) to the extent that polymer collapse to globule can occur at body temperature.

Such functionalisation of highly branched stimulus responsive polymers to bind bacteria can usefully induce or modify stimulus response and LCST. For example functionalisation to confer an ability to bond or interact with species such as bacteria or with polar or hydrophilic environments drives the polymer into its collapsed state at a temperature below its LCST, its LCST is typically above 60 C. Consequently there is no need for precise control of temperature in the handling of this polymer because it will not spontaneously change conformation at room temperature or body temperature, but will only collapse at this temperature when bacteria bind to it.

More preferably the response to stimulus is a change in LCST, such as a reduction in LCST. This can be harnessed to advantage by reduction in LCST to within an intended temperature range of use, for example within the temperature range of the environment within which the material is to be responsive. In the case of medical applications, the LCST may be influenced by modification to lie within the range from room temperature to physiological body temperature.

Highly branched hydrophilic polymer thus provides an inherent indicator for indicating change of indication, and may optionally be functionalised by attachment to said hydrophilic polymer of additional indicator possessing the facility to provide indication as hereinbefore defined on detection of or interaction with bacteria.

In a second embodiment or additionally hydrophilic polymer comprises linear hydrophilic polymer functionalised by the attachment to said hydrophilic polymer of indicator possessing the facility to provide indication as hereinbefore defined on detection of or interaction with bacteria.

More particularly indication as hereinbefore defined indicates an event selected from the stimulus response, interaction with or binding of bacteria by means of an optical change, a molecular or phase change, or a change in adsorption or emission spectra in the UV, visible or Infra red regions of the electromagnetic spectrum.

Conveniently change of indication is displayed as an optical change such as a change in colour, more particularly as a change in fluorescence, or intensity, quantity or magnitude or signal thereof, most preferably as a change in fluorescence wavelength or fluorescence intensity.

Indication of stimulus response, or of interaction with or binding of bacteria thus advantageously provides a means for detection and/or binding of bacteria by type, and additionally quantification thereof.

A device as hereinbefore defined is preferably configured for detecting or sensing species or stimulus present in or comprised at a locus or in an environment preferably in an environment comprising or containing or consisting of or associated with fluid, in particular aqueous fluid including aqueous liquids and vapours such as moisture and physiological fluids. The device is preferably configured to be in fluid communication with such environment. Preferably such environment is a moist environment such as an exuding or humid environment, for example an exuding or humid wound environment or an associated environment such as a wound fluid reservoir or conduit. A device as hereinbefore defined may be activated by fluid contact In a further advantage the device is for monitoring of species, stimulus or stimulus response. This enables for the first time the real time in situ monitoring of species or stimulus or change in species present or in stimulus in a vicinity of or locus of a device.

In a particular advantage the device as hereinbefore defined comprises an indicator which indicates the detection or sensing of species or stimulus or stimulus response by means of an optical change such as a change in colour, more particularly as a change in fluorescence, or intensity, quantity, magnitude or signal thereof such as wavelength, or a molecular or phase change, more preferably a change in adsorption or emission spectra in the UV, visible or Infra red regions of the electromagnetic spectrum, most preferably as a change in fluorescence or fluorescence intensity.

Indication may be by means of stimulus response and/or of indicator comprised within the device. Preferably hydrophilic polymer or a moiety thereof is a copolymer of a hydrophilic monomer and an indicating monomer.

Preferably the hydrophilic polymer is functionalised by the attachment to said polymer of indicator in chain or at branch termini. Indicator may for example comprise one or more dyes, imaging agents, indicating monomers or markers which undergo a detectable change, for example on interaction or binding with bacteria.

We have been able to introduce hydrophilic polymer within a polyurethane network, whereby it is immobilised therein and is not leached.

We have shown the following:
  incorporation of highly branched, linear or extended PNIPAM with carboxylic acid or succinimide end groups into a polyurethane foam and extraction studies to show that PNIPAM can be immobilised and cannot be removed.
  incorporation of highly branched, linear or extended PNIPAM with bacteria binding end groups into a polyurethane foam and extraction studies to show that the PNIPAM can be immobilised and cannot be removed.
  incorporation of highly branched, linear or extended PNIPAM with carboxylic acid or bacteria binding end groups and with nile red labels along the polymer chain into a polyurethane foam or film and extraction studies to show that the PNIPAM can be immobilised and cannot be removed.

We have shown selective bacterial binding by type indicating whether bacteria is Gram positive or Gram negative.

Reference hereinbelow to hydrophilic polymer as highly branched or linear may be read interchangeably unless the sense dictates otherwise.

DESCRIPTION OF THE FIGURES

FIGS. 1.1 and 1.2 illustrate schemes for the preparation of herein defined polyurethane material;

FIG. 1.3 illustrates a scheme for the preparation of herein defined hydrophilic polymer comprising ligand and indicator;

FIGS. 3.1(a) and (b) illustrate stimulus response of samples;

FIG. 3.2 illustrates material herein;

FIGS. 3.3 (a) and (b) illustrate retention and hydrophilic polymer loading of material herein;

FIG. 4.1 illustrates distribution of hydrophilic polymer throughout histological section of material herein;

FIGS. 4.2.1, 4.2.2 and 4.3 illustrate fluorescent activity of material herein;

FIG. 5.1 illustrates selective binding of bacteria by device herein;

FIGS. 5.2 and 5.3 illustrate device herein as bacterially non-inhibiting;

FIGS. 5.4 and 5.5.1 to 5.5.4 illustrate Gram stains of material herein showing type specific binding and indication of bacteria.

FIGS. 6.1 and 6.2.1 to 6.2.3 illustrate a device or dressing herein.

FIG. 6.3 illustrates a flow scheme using the device as indicator on wounds.

DETAILED DESCRIPTION

Stimulus-Responsive Polyurethane Material

Figure 2:
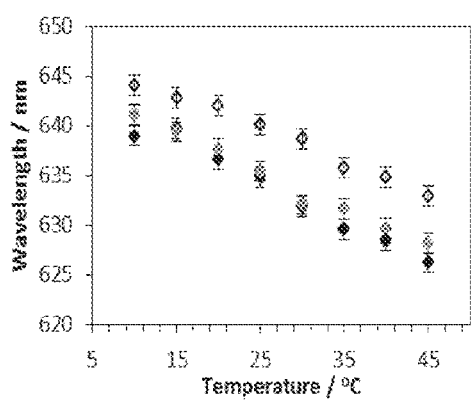
FIG. 2 illustrates LCST effect of extended hydrophilic polymer architecture by shift in peak fluorescence emission wavelength (average mean of distribution) of vancomycin derived extended poly (NIPAM-co-NRA-block-NIPAM) (XBI, black), poly(NIPAM-block-NIPAM-co-NRA) (XBO, clear) samples compared to poly(NIPAM-co-NRA) (gray)

Highly branched hydrophilic polymer as hereinbefore defined such as poly(N-isopropylacrylamide) (PNIPAM or PIPAAm) preferably dissolve in aqueous media below a critical temperature, herein referred to as the lower critical solution temperature (LCST). As the temperature is raised above the LCST, the polymer forms primary particles which aggregate and then undergo sedimentation in the reaction vessel to form a solid mass. Such polymers having a temperature dependent solubility are known as thermoresponsive polymers, and generically as stimulus responsive polymers.

The macroscopic changes that can occur at critical values of pH, temperature or ionic strength with such polymers come about because the polymer changes from an open (solvated) coil to a collapsed state known as a globule. Any aqueous polymer solution will respond in this way to changes in pH, temperature or ionic strength but, for many systems, the critical points occur at temperatures that are above 100 C or below 0 C.

Functionalised stimulus responsive polymers are disclosed in WO2010/094976 hereinabove in the form of hyper branched, otherwise termed highly branched, hydrophilic thermoresponsive polymers with bacteria binding functionality. These functional polymers respond to bacterial binding by passing through a desolvation driven transition in which the polymer passes from a fully solvated open coil to a desolvated globular structure (Tc-g). This desolvation of highly solvated ligands produces a large perturbation in the overall solvency of the polymer and this perturbation can produce significant decreases in its lower critical solution temperature (LCST) to the extent that polymer collapse to globule can occur at body temperature.

Such functionalisation of highly branched stimulus responsive polymers to bind bacteria can usefully induce or modify stimulus response and LCST. For example functionalisation to confer an ability to bond or interact with species such as bacteria or with polar or hydrophilic environments drives the polymer into its collapsed state at a temperature below its LCST, its LCST is typically above 60 C. Consequently there is no need for precise control of temperature in the handling of this polymer because it will not spontaneously change conformation at room temperature or body temperature, but will only collapse at this temperature when bacteria bind to it.

Preferably therefore the highly branched hydrophilic polymer is functionalised by attachment to said polymer of ligand possessing the facility to interact with species in manner to induce or modify stimulus response. More preferably the response to stimulus is a change in LCST, such as a reduction in LCST. This can be harnessed to advantage by reduction in LCST to within an intended temperature range of use, for example within the temperature range of the environment within which the material is to be responsive. In the case of medical applications, the LCST may be influenced by modification to lie within the range from room temperature to physiological body temperature.

Polyurethane Material

The polyurethane material is in the form of an entrapped semi interpenetrating network (ES-IPN) of a polyurethane polymer penetrated by a hydrophilic polymer as hereinbefore defined. By this is meant that it follows the same synthesis route although we cannot be certain that it forms a true IPN structure. Significantly the polyurethane material is the product of polymerisation in the presence of the hydrophilic polymer. Suitably the polyurethane material is the product of step growth polymerisation in the presence of the hydrophilic polymer. Step growth polymerisation causes the polyurethane chains to grow about and through the hydrophilic polymer which thus becomes entwined and entrapped within the polyurethane network.

S-IPNs and F-IPNs are of great utility in many sectors because they can provide materials with properties and functionality of both components. However F-IPNs are difficult to manufacture because it is often necessary to find either concurrent polymerisation processes that do not interfere with each other or to swell a preformed network with another monomer and then polymerise this polymer/monomer blend. The concurrent polymerisation route is only applicable to certain combinations of materials and the swelling approach can produce distortions of premolded devices. On the other hand S-IPNS that can be more easily manufactured by mixing in a macromolecule during the polymerisation and crosslinking of the network polymer, are often used in contact with fluids that swell the crosslinked component and dissolve the linear component and are not useful because the linear component is easily extracted or is capable of leaching from the crosslinked component.

The present invention relates to the improvement of S-IPNs in the form of the ES-IPN as hereinbefore defined wherein the highly branched hydrophilic polymer is entwined within and penetrated by the polyurethane polymer network and thereby entrapped therein. We have surprisingly found that the highly branched hydrophilic polymer as hereinbefore defined is separable from the penetrating network in theory only and not in practice and is not capable of leaching or of being extracted from the crosslinked polyurethane polymer network. Without being limited to this theory the highly branched hydrophilic polymer is not capable of diffusing through the network because the branch points can not diffuse past the crosslinks of the network. Alternatively or additionally some or all or part of the highly branched hydrophilic polymer forms bonds with the polyurethane, in the form of H-bonds, covalent bonds, grafts or other interactions. Bonds remain intact in the presence of aqueous solvent. Immobilisation of highly branched hydrophilic polymer may be the result of such bond formation or of entrapment by the penetrating network or both.

We have surprisingly found that the hereinbefore and hereinbelow defined stimulus-responsive polyurethane material does not release the entrapped highly branched hydrophilic polymer. Upon exhaustive washing in solvents effective for the copolymer, such as aqueous ethanol, ethanol, dichloromethane or acetone, the copolymer remains held in the polyurethane network, despite swelling of the polyurethane network in said solvents. The copolymer is therefore held in manner such that it is resistant to removal by swelling of the surrounding polymer network, by solvent extraction or by solvation effects.

Polyurethane material may be in any form suited for the intended purpose. Preferably polyurethane material is in the form of a foam, film, perforated film, membrane, water impermeable membrane providing moisture vapour transmission (MVT), adhesive layer or coating, sheet, block, non-woven or woven fabric, fibers and the like and combinations thereof.

Polyurethane material in a form as hereinbefore defined may be foamed, unfoamed or xerogel.

A foam is preferably open cell as known in the art. We have found that a polyurethane foam formation is not disrupted by the presence of the hydrophilic polymer.

A xerogel is a solid formed from a gel by drying with unhindered shrinkage. Xerogels usually retain high porosity (15-50%) and enormous surface area (150-900 m$^2$/g), along with very small pore size (1-10 nm).

Xerogels are well suited to the immobilisation of hydrophilic polymer as hereinbefore defined in gel form. An adhesive layer or coating may be applied to a device or part thereof as a gel, more preferably a xerogel, as known in the art.

Preferably polyurethane material possesses the facility to conform to or be deformed or conformed to fit or cover a locus such as a wound surface. Conformable material possesses the advantages of facilitating mapping of species across a surface for example mapping bacteria or pH profiles across a locus, in particular a wound. This has clear benefits over detecting bacteria or pH at isolated locations. Mapping is particularly advantageous as the pH or bacteria in a wound is often not uniform across the wound. Importantly it is surmised that all wounds contain sub critical levels of bacteria, however as the population increases it reaches a detrimental magnitude in the wound which is classified in order of severity as contaminated, colonised, critically colonised and ultimately as infection level. These levels are given the meaning known in the art. Advantages are also apparent in the use of the herein defined polyurethane materials in relation to systems from which bacteria can readily propagate and for which it is desired to rapidly identify the source or epicentre of detected bacteria or their population, such as in relation to wounds, air conditioning systems, water management systems and the like. Polyurethane material in the form of conformable cover material as hereinbefore defined confers the facility to detect the location of a bacterial population which is of detrimental magnitude.

Polyurethane Network

Preferably polyurethane network is the product of reaction of an isocyanate terminated monomer and a long chain diol and/or polyol. Reaction generates the isocyanate terminated oligomeric prepolymer. The polyurethane network is the result of chain extension or crosslinking said isocyanate terminated oligomeric prepolymer, with use of chain extending long chain diol and/or polyol or crosslinking agent which may be introduced simultaneously with or subsequent to the polymerisation reaction.

Isocyanate terminated monomer may be aromatic or aliphatic. Preferably aromatic isocyanate terminated monomer is selected from one or more of toluene diisocyanate (TDI), methylenediphenyl isocyanate (MDI), para phenylene diisocyanate (PPDI) and naphthalene diisocyanate (NDI).

Preferably aliphatic isocyanate terminated monomer is selected from one or more of hexamethylene diisocyanate and dicyclohexyl methyl diisocyanate (hydrogenated MDI) and the like.

Long chain diol or polyol is conveniently selected from one or more polyols or diols of polyester, polycaprolactone, polyether and polycarbonate, more preferably the polyols thereof. For example polyether long chain polyol is selected from polytetramethylene ether glycol (PTMEG), polyoxypropylene glycol (PPG) and polyoxyethylene glycol (PEG).

Isocyanate terminated monomer and long chain diol or polyol are conveniently provided in the form of an isocyanate terminated polyether prepolymer thereof for example as commercially available in the range of HYPOL polyurethane prepolymers (W R Grace & Co). HYPOL prepolymer includes prepolymer of aromatic isocyanates HYPOL polyurethane foams may be prepared by reacting the isocyanate terminated polyether prepolymer with water.

Non-foamed HYPOL polyurethane such as blocks, films, membranes or the like may be prepared by reacting the isocyanate terminated polyether prepolymer with diol or polyol.

Essentially non aqueous polyurethane such as xerogel may be prepared by reacting a prepolymer of a polyisocyanate and a polyol such as a glycol such as diethylene glycol or low molecular weight polyethylene glycol or polypropylene glycol (PEG or PPG). Such polyisocyanate may be an aliphatic polyisocyanate. Such polyisocyanate is commercially available for example as Desmodur N100.

Hydrophilic Polymer

Suitably the hydrophilic polymer is combined with the polyurethane components prior to casting into a mould or onto a surface. Polyurethane material may be cast into a mould or onto a surface to form a foamed or non foamed block or sheet, gel, membrane or film, or to form fibers or the like.

It is one benefit of the invention that hydrophilic polymer may be simply blended with the polyurethane components or ingredients during the reaction thereof and prior to chain extension or crosslinking, whereby it is immobilised within the polyurethane network. Hydrophilic polymer may be blended with one of the polyurethane components or ingredients prior to combining the respective components or ingredients. For example hydrophilic polymer may be combined with an isocyanate component or polyol component or both such as the HYPOL phase or the long chain diol and/or polyol phase in a polyurethane system.

Preferably the hydrophilic polymer is provided in fluid phase, preferably dissolved in solvent prior to combining with one or more polymerisation reaction components or dissolved or solvated in situ in one or more of the polymerisation reaction components. Hydrophilic polymer introduced in dissolved form is more readily able to form an interpenetrating or entangled network with the polyurethane polymer.

Hydrophilic polymer provides a hydrophilic environment. Polymer or indicator immobilised thereon, provides an indication or response on change of hydrophilic nature of environment, such as increase or decrease in hydrophilicity, or decease or increase in polarity. In particular in a material as hereinbefore defined, a decrease in hydrophilicity is initiated by a number of factors including presence of lipid membranes such as in microbial environments. Change in hydrophilicity may be local, i.e. may occur within or specific to zones of the hydrophilic polymer and thereby within or specific to zones of the polyurethane material.

Indicator is comprised in the hydrophilic polymer, preferably covalently bound thereto, more preferably as a copolymer as hereinbefore defined. Indicator is configured to provide indication and change of indication in relation to the directly proximal zone of the hydrophilic polymer or surface. In a particular advantage the material is thereby configured to provide indication relating to location of detected species or stimulus such as bacteria, acid or base groups or pH.

Hydrophilic polymer may be provided in the polyurethane material in any desired amount. Hydrophilic polymer may be present in an amount from a trace amount up to the maximum amount which the crosslinking or chain extension process tolerates. Preferably hydrophilic polymer is present in an amount greater than or equal to a trace amount, preferably in an amount of from 0.01 wt % up to 20 wt %, such as from 0.1 wt % up to 20 wt %. preferably from 1 wt % up to 20 wt % An economic consideration promotes operation in the lower end of the range for example from 0.01 wt % to from 4 wt %, balanced against performance consideration which promotes operation in an intermediate region or upper end of the range for example from 4-20 wt %, for example 4-15 wt %. In a particular advantage we have found that it is possible to achieve amounts of hydrophilic polymer in the range 6-20 wt %, for example 6-15 wt %.

Highly branched hydrophilic polymer or linear hydrophilic polymer is preferably selected from polyacrylamides, polyacrylic acids, such as poly acrylamide, polyalkyl acrylamide, polyallyl acrylamide, polyacrylic acid, polymethacrylic acid, and their copolymers, polymers of acidic monomers and polymers of cationic monomers. More preferably the highly branched hydrophilic polymer is selected from polyalkyl acrylamide wherein alkyl is ethyl, propyl or butyl such as poly(N-isopropyl acrylamide) (PNIPAM), polyacrylic acid, polymethacrylic acid, and copolymers thereof. Copolymers may be with other polymers or substrates. Copolymers may confer same or different responsivity.

Particularly envisaged for microbial detection is polyalkyl acrylamide, preferably wherein alkyl is ethyl, propyl or butyl more preferably poly(N-isopropyl acrylamide) (PNIPAM).

Particularly envisaged for pH detection are polyacrylic acid and polymethacrylic acid.

Highly branched hydrophilic polymer or linear hydrophilic polymer may be present in substantially uniform molecular weight or in a distribution of molecular weight. A distribution of molecular weight presents a distribution of total branching or chain length and thereby a distribution in total functionalization, i.e. ligand content. Advantageously such polymer provided in a distribution of molecular weight provides low, intermediate and high sensitivity response or indication thereof, for example of binding of species such as bacteria.

In a further advantage hydrophilic polymer present in a distribution of molecular weight provides for quantitative assessment of species or stimulus, wherein level of detected or sensed response is proportional to the amount of species or degree of proliferation thereof, or the degree of stimulus present.

Highly Branched Hydrophilic Polymer

Highly branched stimulus responsive polymer or highly branched hydrophilic polymer is also known in the art as hyper branched. The degree of branching may vary and may be expressed in a number of ways, for example as the number of branched sites divided by the total number of monomer sites.

It is perhaps more convenient to consider the polymer as comprising a plurality of repeat units and a plurality of branch points wherein the degree of branching is defined as the ratio of repeat units to branch points. Preferably the highly branched hydrophilic polymer as hereinbefore defined is characterised by a ratio of repeat units to branch points of less than 45:1, preferably less than 35:1, such as less than 30:1, and preferably less than 20:1. For example in the range 5-45:1, preferably 8-35:1, more preferably 10-30:1, most preferably 12-20:1. This corresponds to the ratio of monomer to polymerisation agent or branching agent. Preferably monomer:branching agent, for example RAFT agent, is in the range 5-45:1, preferably 8-35:1, more preferably 10-30:1, most preferably 12-20:1.

Sensing or Detecting Ligand or Moiety

Ligand or moiety is preferably covalently bound to the hydrophilic polymer.

Ligand or moiety may be covalently bound to attachment groups such as for example carboxylic acid or succinimide groups.

Preferably hydrophilic polymer is a copolymer with attachment monomer providing attachment groups.

Preferably linear hydrophilic polymer is a copolymer of the hereinbefore defined monomers with attachment monomer for example such as vinyl benzoic acid.

Preferably highly branched hydrophilic polymer is a copolymer of the hereinbefore defined monomers with attachment monomer for example such as RAFT monomer.

Alternatively ligand or moiety may comprise functional groups provided by the hydrophilic polymer, or provided by interchange of functional groups provided by the hydrophilic polymer. Ligand or moiety may for example comprise acidic or basic functional groups.

Ligand or moiety is preferably provided at the polymer chain termini including the ends of a plurality of the polymer branches or the ends of the polymer backbone, and optionally additionally at a plurality of sites along the polymer backbone. Ligand or moiety may be provided at substantially all of the polymer branches or backbone sites and termini or at a percentage thereof.

Ligand may be bound in any convenient ratio within the hydrophilic polymer, for example up to 35:1 ligand:hydrophilic polymer.

We have found that there is an optimum range of binding ratio at the lower end of which the hydrophilic polymer presents sufficient ligand to give a measurable response and at the upper end of which the ligand is oriented to be freely available to detect bacteria. Above this optimum range it is possible that access to ligands becomes obstructed and some ligand becomes unavailable for binding.

In an advantage, ligand present in high ratio as hereinbefore defined possesses the facility to gather or accumulate species such as bacteria by binding or interaction, in manner to create a species dominant environment in the proximity of the hydrophilic polymer. We believe that this further enhances the range of sensitivity of detection, sensing or binding, and the facility of the polymer material to provide low, intermediate and high sensitivity indication of detection, sensing and/or binding, for example of species such as bacteria.

Hydrophilic polymer may comprise a plurality of ligands selective for a plurality of species or stimulus. A plurality of ligands may be provided on the same polymer molecule. Alternatively an amount of hydrophilic polymer may comprise a ligand selective for one species or stimulus and an amount of hydrophilic polymer may comprise a further ligand selective for a further species or stimulus.

In the case of more than one ligand, hydrophilic polymer may provide more than one indicator. One indicator may be specific for indicating sensing or detecting or binding by one ligand and a further indicator may be specific for indicating, sensing or detecting a further ligand.

Orientation of ligand in relation to the copolymer is not insignificant. Hydrophilic polymer suitably comprises ligand disposed in pendant manner, for example at branch termini, along the backbone or at chain termini.

Microbe detecting ligand or moiety is most preferably immobilised to hydrophilic polymer comprising a polyalkyl acrylamide or copolymer thereof.

pH sensing or detecting function or moiety is most preferably present immobilised by hydrophilic polymer such as for example polyacrylic acid, polymethacrylic acid or copolymer thereof.

Ligand or moiety is suitably provided as groups pendant to the hydrophilic polymer, at linear or branch termini, along the backbone or both.

pH Sensing Function pH detecting function, hereinabove and hereinbelow ligand or moiety, is suitably selected from one or more acid groups or base groups. Preferably pH detecting function or moiety is selected from one or more acid groups, for example comprises —COOH groups.

pH detecting function response bears charge or is uncharged at different pH. —COOH groups are charged at high pH or are uncharged at low pH. Change in pH from high to low pH at a locus causes coil to globule collapse.

pH detection or pH of stimulus response is dependent on the pH sensing functionality or moiety. Depending on the pH sensing functionality or moiety, the coil to globule collapse in a stimulus responsive polymer as hereinbefore defined occurs at a given pKa, for example where a pH sensing functionality or moiety is ~COOH the collapse is in the region of pKa 5.

Accordingly in a pH sensing or detecting device as hereinbefore defined, stimulus response is responsive to detecting or sensing species or stimulus or change in species or stimulus such as presence of microbes or change in pH, and indicator is responsive to stimulus response. Preferably stimulus is change of polarity or hydrophilicity and stimulus response is change of hydrophilicity of hydrophilic polymer, more preferably in the form of coil to globule collapse.

Microbe Detecting Ligand

Microbe detecting function is suitably selected from one or more ligands or moieties which detect or sense, and optionally interact with or bind microbe. Ligand may be specific to a microbe or microbes which it is desired to detect and/or monitor.

Preferably ligand or moiety is selected from one or more peptide antibiotics and their bacteria derivatives including glycopeptides and lipopeptides, non-peptide antibiotics and their derivatives, antibody fragments that detect, sense or bind to bacteria, peptide sequences such as small RNA and DNA sequences such as apatemers, and oligo- and monosaccharides that detect, sense or bind to bacteria and combinations thereof. Other examples of suitable bacteria binding ligands include any low molecular weight compounds that selectively detect, sense and optionally bind to any cell surface receptor on bacteria. Especially suitable ligands are bacteria sensing or detecting or binding peptides and combinations thereof and in particular antibiotic or non-antibiotic peptides and their derivatives.

A derivative includes a modification which is devoid of bactericidal activity, herein is antimicrobially inactive, preferably antibiotically inactive. A derivative may retain the capacity to detect and interact with bacteria, for example to reorganise the outer membrane of bacteria.

Bacteria detecting, sensing and/or binding ligand or moiety is suitably selected from one or more ligands for interacting with or binding Gram positive bacteria and/or one or more ligands for interacting with or binding Gram negative bacteria. Hydrophilic polymer may comprise one or more ligands selective for Gram positive bacteria and one or more ligands selective for Gram negative bacteria provided on the same polymer molecule. Alternatively an amount of hydrophilic polymer may comprise one or more ligands selective for Gram positive bacteria and an amount of hydrophilic polymer may provide one or more ligands selective for Gram negative bacteria.

In the case of more than one ligand, hydrophilic polymer may provide more than one indicator. One indicator may be specific for indicating sensing or detecting Gram positive bacteria by one ligand and a further indicator may be specific for indicating, sensing or detecting Gram negative bacteria by a further ligand.

Ligand may possess the facility to sense or detect Gram positive bacteria for example selected from *Staphylococcus* such as *Staph. aureus*, Staph. epidermidis and MRSA, *Streptococcus*, Enterococcus, Corynebacterium and Clostridium such as C. difficile, also Peptostreptococcus, Lactobacillus, Propionibacterium, Bifidobacterium and Actinomyces.

Alternatively or additionally ligand may possess the interact with facility to sense or detect Gram negative bacteria for example selected from proteobacteria such as Enterobacteriaceae for example, *Escherichia coli, Salmonella*, Shigella, Pseudomonas such as Pseudomonas aeruginosa, Proteus, Klebsiella, also Legionella, Hemophilus, Neisseria, Acinetobacter such as A. baumannii, Bacteroides, Prevotella, Fusobacterium, Porphyromonas and the cyanobacteria and spirochaetes.

Preferably ligand is selective for bacteria encountered in a wound environment. Such bacteria may include for example Gram negative aerobic bacteria such as *Pseudomonas aeruginosa*, Gram positive bacteria such as *Staphylococcus aureus*, more particularly MRSA (methicillin resistant *Staphylococcus aureus*) also known as ORSA (oxacilin resistant *Staphylococcus aureus*) anaerobic bacteria such as *Bacteroides fragilis*, yeast such as *Candida albicans* and fungi such as *Aspergillis braziliansis*. In an advantage ligand possesses the facility to sense or detect and optionally interact with and/or bind at least Gram positive and/or Gram negative bacteria, for example in a level of bioburden including any of contaminated, colonised, critically colonised and infection level. These levels are given the meaning known in the art.

More preferably the bacteria binding ligand is selected from one or more of vancomycin, polymyxin, beta-lactam and teicoplanin antibiotics and cationic peptides such as the cecropin and melittin hybrid, CEME and defensins and antimicrobially inactive, preferably antibiotically inactive derivatives thereof.

Bacteria binding ligand may be derived from a reactive form thereof suitable for reacting with or derivatising the hydrophilic polymer. For example polymyxin provided as a ligand to the hydrophilic polymer is derived from a modified polymyxin which is reactive with the hydrophilic polymer. Specifically polymyxin is provided in form devoid of antibiotic activity. Antibiotically inactive polymyxin is deacylated at one acyl chain thereof.

Preferably hydrophilic polymer is derivatised by the attachment of one or more peptide antibiotics.

Preferably attachment of said ligands to highly branched hydrophilic polymer is at the ends of a plurality of the polymer branches.

or at a plurality of sites along the polymer backbone and at the polymer chain termini. Attachment is preferably achieved by linkage to binding groups such as for example carboxylic acid or succinimide groups. Preferably attachment is at the end of a multitude of the polymer branches or at a multitude of backbone sites and polymer chain termini. Attachment may be at substantially all of the polymer branches or backbone sites and termini or at a percentage thereof.

Preferably hydrophilic polymer for sensing or detecting and optionally binding bacteria comprises vancomycin or polymyxin or derivatives as hereinbefore defined, in a ratio of up to 35 moles ligand to 1 mole hydrophilic polymer.

It is convenient to express ligand:hydrophilic polymer as a wt:wt ratio. Preferably such ligand:hydrophilic polymer is in the range 3-30:100 wt:wt.

We have found that there is an optimum range of binding ratio at the lower end of which the hydrophilic polymer presents sufficient ligand to give a measurable response and at the upper end of which the ligand is oriented to be freely available to detect bacteria. Above this optimum range it is possible that access to ligands becomes obstructed and some ligand becomes unavailable for binding.

In an advantage, ligand present in high ratio as hereinbefore defined possesses the facility to gather or accumulate species such as bacteria by binding or interaction, in manner to create a species dominant environment in the proximity of the linear polymer. We believe that this further enhances the range of sensitivity of detection or binding, and the facility of the polymer material to provide low, intermediate and high sensitivity indication of detection and/or binding, for example of bacteria.

Orientation of ligand in relation to the copolymer is not insignificant. Hydrophilic polymer suitably comprises ligand disposed in pendant manner, for example at branch termini, along the backbone or at chain termini.

Indicator

Indicator as hereinbefore defined preferably provides indication or change in indication in the form of an optical change, a molecular or phase change, or a change in adsorption or emission signal or spectrum in the UV, visible or Infra red regions of the electromagnetic spectrum.

Indicator may indicate a change in stimulus response as a result of binding or of sensitivity to its environment induced directly or indirectly by said stimulus. Preferred indicator indicates a change in stimulus or a change in stimulus response as hereinbefore defined, such as presence or type of bacteria or change in pH, or a change in polarity or hydrophilicity.

Indicator such as dyes, imaging agents, indicating monomers and the like are known in the art and include species sensitive indicators which may sense or detect a species directly, e.g. by interaction therewith, or indirectly, e.g. by sensing or detecting a change initiated by the species, such as desolvation resulting in coil to globule transition as hereinbefore described or binding to ligand as hereinbefore defined. Suitably indicator is selected from those which are sensitive to bacteria, hydrophobic or hydrophilic or polar environments, such as their lipid-rich environment, to pH and the like.

Preferably indicator is selected from solvatochromic dyes, including fluorescent dyes, colour changing indicators, and combinations thereof and their polymerisable monomers or oligomers. Solvatochromism is the ability of a chemical substance to change color due to a change in solvent polarity. Preferred indicator includes polymerisable fluorescent solvatochromic dyes, i.e. dyes which may be incorporated as a copolymer with the hydrophilic polymer and which change fluorescence in response to a change in polarity. Solvatochromic dyes provide a change in maximum absorption and in fluorescence in response to a polar to non-polar transition. Preferred solvatochromic indicator exhibits a wide range of polar sensing.

Preferred indicators include any which are polymerisable or which may be rendered polymerisable and which exhibit fluorescent solvatochromic behaviour.

More preferably indicator is selected from one or more of the naphthalenes, phenoxazines, phenylazenes and phenylazos compounds and their derivatives, for example Dansyl cadavarine (5-amino pentyl)-5-diethylamino-1-napthalene sulphonamide) and reactive derivatives thereof including Dansyl chloride and N-[2[[[(5-N,N-dimethylamino)-1-naphthalenyl sulphonyl]-amino]ethyl]-2-propenamide (DANSAEP), Nile Red™ (9-diethylamino-5H-benzo[a]phenoxazine-5-one) 2-[4(2-hydroxyethylsulfonyl)-phenyl]diazenyl]-4-methylphenol, Nile Blue 5-amino-([9-(diethylamino)benzo[a]phenoxazin-7-ium) sulphonate and polymerisable forms including the corresponding acrylamide, 1-hydroxy-4-[4[(hydroxyethylsulphonyl)-phenylazo]-napthalene-2-sulphonate, 2-fluoro-4-[4[(2-hydroxyethanesulphonyl)-phenylazo]-6-methoxy phenol, 4-[4-(2-hydroxyethylsulphonyl)-phenylazo]-2,6-dimethoxyphenol, fluorescent monomers with benzofurazan skeleton, including for example 4-(2-acryloyl oxyethylamino)-7-nitro-2,1,3-benzoxadiazole (NBD-AE) and 4-(2-acryloylaminoethylamino)-7-nitro-2,1,3-benzodiazole (NBD-AA), 4-amino-1,8 napthalimide derivatives including 2-(6-(dimethylamino)-1,3-dioxo-1H-benzo(de)isoquinolin-2(3H)-yl) ethyl methacrylate and reactive derivatives and combinations thereof.

Reference herein to Nile Red™, includes its reactive derivatives in particular hydroxyl Nile Red™ 9-(diethylamino-2-hydroxy-5H-benzo[a]phenoxazine-5-one and Nile Red™ acrylate 9-(diethylamino-2-acryloyloxy-5H-benzo[a]phenoxazine-5-one. Nile Red is known as a fluorescent indicator for bacteria and intracellular lipids. Nile Red fluoresces in lipid-rich environments. Fluorescence is at different wavelength according to the polarity of the environment, and Nile Red does not fluoresce in most polar solvents. It can be readily visualised using an epifluorescence microscope.

Nile Red™ is commercially available as 9-diethylamino-5H-benzo[a]phenoxazine-5-one. Hydroxyl Nile Red™ may be obtained in known manner or Nile Red acrylate may be obtained by synthesising the hydroxyl derivative of Nile Red and reacting with acryloyl chloride for example as disclosed in Chemistry of Materials 2011, 23, 3348-3356, the contents of which are incorporated herein by reference.

The fluorescence characteristics of Nile Red™ monomer are essentially the same as Nile Red™ as follows Nile red absorbance max in water=584 nm, emission max in water=666 nm Absorbance max in cyclohexane=469 nm, emission max in cyclohexane=570 nm, ref Green Chemistry 2001, 3, 210-215

Nile Blue is commercially available as the 5-amino 9-(diethylamino)benzo[a]phenoxazin-7-ium sulphonate which may conveniently be converted to the corresponding acrylamide.

Nile blue absorbance max in water=635 nm, emission max in water=674 nm

Absorbance max in chloroform=624 nm, emission max in chloroform=647 nm,

Reference herein to Dansyl™, includes its reactive derivatives in particular Dansyl chloride. Dansyl™ is commercially available as Dansyl™ cadavarine (5-amino pentyl)-5-diethylamino-1-napthalene sulphonamide). Dansyl cadaverine may be reacted with acryloyl chloride to give an acrylamide derivative, or may be provided as N-[2[[[(5-N,N-dimethylamino)-1-naphthalenyl sulphonyl]-amino]ethyl]-2-propenamide (DANSAEP) as disclosed in Chemical Physics Letters 307 (1999) 55-61 the contents of which are incorporated herein by reference.

Dansyl cadaverine is commercially available. Dansyl acrylamide may be obtained in known manner for example as disclosed in Chemical Physics Letters 307 (1999) 55-61, the contents of which are incorporated herein by reference.

Dansyl monomer has fluorescence characteristics including absorbance max in water=329 nm, emission max in water=530 nm, absorbance max in hexane=333.7 nm, emission max in hexane=463 nm.

Fluorescent monomers with benzofurazan skeleton as hereinbefore defined may be obtained in known manner for example as disclosed in Analytical Chemistry 2003, 75, 5926-5935, the contents of which are incorporated herein by reference.

Fluorescent monomers with benzofurazan skeleton may be excited at 469 nm.

NBD-AE emission max in isobutanol 519 nm, emission max in water 535 nm

NBD-AA emission max in isobutanol 521 nm, emission max in water 536 nm 4-amino-1,8 naphthalimide derivatives as hereinbefore defined may be obtained in known manner for example as disclosed in Journal of Materials Chemistry C, 2013, 1, 6603-6612, the contents of which are incorporated herein by reference.

4-amino-1,8 naphthalimide derivatives. When polymerised with NIPAM, have an absorbance max in PBS, 20 C=448 nm, emission maximum in PBS, 20 C=544 nm, absorbance max in chloroform=422 nm, emission maximum in chloroform=513 nm.

Preferred indicator has a narrow emission range, more preferably narrow excitation and emission ranges for example in a range of 5 up to 100 nm, more preferably 5 up to 50 nm, most preferably 2-20 nm.

Indicator may be incorporated in any desired manner in the stimulus-responsive polyurethane material, and is preferably incorporated in the highly branched hydrophilic polymer, preferably by covalent binding at a plurality or multitude of branches. Preferably indicator is provided as a copolymer with hydrophilic polymer as hereinbefore described, preferably as a copolymer of a polymerisable indicating monomer. Preferably indicator is incorporated in ratio corresponding to species-detecting functional group, for example ligand or functionality. More preferably indicator is covalently bound to a plurality or multitude of branches or of branch termini. In a particular advantage indicator is present in an amount defined as molar ratio of hydrophilic polymer:indicator of >50:1, preferably 1000-2500:1, for example 1500-2200:1. Indicator present in such relatively low amounts provides the required sensitivity and moreover provides superior indication, Preferably indicating monomer is provided as wt/wt ratio with hydrophilic monomer of 3-30:100 indicating monomer:hydrophilic monomer Use The device as hereinbefore defined may be for any use in which detection or binding of a species is desired, for example detection or sensing or binding or indicating of a species or stimulus is desired, for example detection or sensing binding or indicating of a chemical or biological species or stimulus.

Suitably the device is for use in applications selected from medical, dental, hygiene, point of use sterilisation, sanitation, personal care, biosurveillance and packaging.

Preferably the device is for detecting, sensing and/or binding bacteria, or for detecting or sensing pH and the like.

Such uses include for example the management of wounds, hygiene and sterilisation of articles including medical and dental articles, hygiene and sterilisation of food or of fluids, including water and air, or systems for their preparation and generation such as food preparation or packaging plants, ventilation systems, water management systems, and in particular such uses for which the detection or binding of bacteria, monitoring of pH, and the like is beneficial.

The device may be in desired form suitable for the intended use, for example sheet form. Suitably the device is in the form of a block, sheet, film, membrane, layer or coating, fiber, woven or non-woven being foamed or non foamed, in particular being conformable foam block or sheet, film, membrane, woven or non-woven or layer is particularly envisaged as hereinabove described.

In a preferred embodiment the device is for use as a wound dressing or part thereof, for interrogating biological fluids including wound fluid, serum, urine, as a medical or dental sponge or wipe or the like, or pH probe or sensor in such applications or independent applications.

Material for use as a wound dressing or part thereof or in interrogating biological fluids includes use for interrogating wound fluid, for example may be in form of a dipstick, lining for vacuum line or wound fluid conduit, collar for wound fluid conduit port, wound fluid filter, wound filler or top film for wound filler and the like, in particular in relation to negative pressure wound therapy (NPWT), collar for port in other applications providing at the port a moist locus or environment as hereinbefore defined, and the like.

Preferably the device comprises a wound dressing or is for use as a secondary or primary dressing in conjunction with a primary or secondary wound dressing. As a primary dressing the device may be in the form of a wound contact layer or wound filler for an absorbent, odour absorbing or like secondary dressing, for example in moist wound healing. As a secondary dressing the device may be in the form of a fluid absorption or odour absorption layer supplementary to that of a primary dressing or be in the form of a top film to retain a primary dressing in place. Such decision may be the clinician's choice. pH or presence of bacteria may be assessed upon application of and removal of the device as primary dressing from the wound. The device may be intended for positioning at or near a lower surface of a secondary dressing. The device may be the wound contacting layer for the secondary dressing. The device may be for use as a cover layer, or intermediate layer for a primary dressing In management of deep or chronic wounds, the device may be placed into the wound to detect bacteria or pH and removed from the wound intact. Foam for use with negative pressure wound dressing is particularly contemplated.

Devices containing immobilized PNIPAM polymers may be used to detect pH or bacteria remote from the wound. For example polyurethane material may be provided in the form of a polyurethane film or polyurethane foam plug for insertion in the vacuum line of a NPWT device, for example at the entrance to a port provided on a NPWT dressing. A device is thereby configured to contact wound fluid emanating from a wound bed to be drawn off via a vacuum line.

Such wound fluid may thereby be caused to flow over or through the device. The device may thereby provide indication of species or stimulus in relation to the fluid.

A device may be provided in the form of a polyurethane film for use under the drape of a NPWT dressing located over a filler material. Polyurethane material is thereby configured to contact wound fluid comprised within the filler material as a reservoir of fluid for removal via a vacuum line. The device may thereby provide indication of species or stimulus in relation to the fluid.

A device may be provided in the form of a polyurethane foam for use as a dipstick or swab. The device is thereby configured to contact wound fluid comprised in a wound locus by contact with the wound surface. The device may thereby provide indication of species or stimulus in relation to the fluid.

Accordingly a device for use as a wound dressing or part thereof or in interrogating biological fluids includes use for interrogating wound fluid, for example may be in form of a dipstick, lining or plug for vacuum line or wound fluid conduit, collar for wound fluid conduit port, wound fluid filter, wound filler or top film for wound filler and the like, in particular in relation to negative pressure wound therapy, collar for port in connection with a fluid environment and the like.

The material or device may be provided in shape or size or a range of shapes or sizes suitable for use on a wound or at a locus, or may be cut to size or shape.

Preferably the device is manufactured with use of a block or sheet, film or membrane cut to size and shape in the manufacture of a device for use as hereinbefore defined for example as a wound dressing or part thereof or for use in interrogating wound fluid or other uses as hereinbefore defined.

In a particular advantage the hydrophilic polymer provides indicator and ligand or moiety distributed throughout the polyurethane network, whereby indicator and ligand or moiety are provided at any face of a device even when manufactured from material cut to size or shape. This is a particular advantage when compared to devices having bacterial or pH sensing function applied as a coating at a surface, and which are not active at a face exposed by cutting after coating.

The device may be for use in treating wounds which are contaminated by or susceptible to contamination by microbes as hereinbefore defined. A particularly useful application is in treating wounds contaminated by or susceptible to contamination by bacteria, yeast and/or fungi.

Wound management includes management of chronic and acute, full thickness, partial thickness, and shallow granulating exuding wounds. Wounds for which the hereinbefore defined material has particular use include for example ulcers and pressure sores such as leg ulcers; pressure ulcers; diabetic ulcers; surgical wounds; traumatic wounds; donor sites; burns such as partial thickness burns; tunnelling and fistulae wounds; wounds left to heal by secondary intent; and wounds that are prone to bleeding such as wounds that have been surgically or mechanically debrided, cavity wounds, sinus and open wounds.

Method for Manufacture of Device

In a further aspect the invention comprises a method for the manufacture of a device as hereinbefore defined comprising generating a surface configured to contact a locus as hereinbefore defined wherein the surface comprises a polyurethane material as hereinbefore defined.

The method may comprise cutting a sheet of polyurethane material to size or shape to generate a surface as hereinbefore defined. Alternatively the method comprises providing a surface and providing a polyurethane material as hereinbefore defined applied to a face thereof configured to contact a locus, or to an opposing face thereof.

Preferably the method comprises sterilisation in known manner.

Construct

In a further aspect the invention comprises a construct comprising a device as hereinbefore defined fabricated together with additional components. A construct may comprise a surface as hereinbefore defined provided in a device as hereinbefore defined together with one or more layers of functional material as a laminar device. Layers may be coextensive with the surface or device or otherwise, for example may comprise a strip or zone superimposed on the surface or the device or a part thereof.

A strip or zone may comprise a reference strip providing reference information for processing information relating to indication and change in indication and generating output information relating to bacteria or pH.

A reference strip may comprise information relating to wavelength, and may further comprise a temperature sensor. Wavelength and/or temperature information may be used in calibrating the construct.

A strip or zone or layer may comprise a display such as a VDU, preferably a flexible VDU such as a polymeric VDU for displaying reference information, information relating to indication or change in indication, or output information derived by processing thereof.

Layers of functional material may include one or more layers of perforated film or mesh, fluid-impermeable film, superabsorbent material and/or fluid distributing material and obscuring material.

Such layer may be of size and shape corresponding to the conventional equivalent. Alternatively such layer may extend across only one or more parts or zones of the construct. For example a foam layer may be of part thickness and may be positioned in laminar manner with a corresponding conventional layer of reduced thickness. A wound contact layer may comprise an adhesive layer of polyurethane material as herein defined such as a xerogel as herein defined optionally applied to a conventional film. A fluid impermeable film may optionally be provided and comprise polyurethane material as herein defined, applied as a film in conventional manner.

In a further aspect there is provided a method for manufacturing a construct as hereinbefore defined comprising providing a device or sheet of conformable polyurethane material as hereinbefore defined in desired shape and size, and optionally providing together with one or more layers of functional material as a laminar device, preferably together with one or more layers of perforated film, fluid-impermeable film, superabsorbent material and/or fluid distributing material. The method may comprise positioning an obscuring layer optionally comprising one or more windows to facilitate inspection or interrogation of the construct.

Wound Dressing

In a further aspect the invention comprises a wound dressing comprising (a) a wound contacting surface or layer (b) an opposing non-wound contacting surface or layer (c) an optional wound exudate absorbing layer comprised between (a) and (c)

wherein (a) and/or (b) and/or (c) comprises polyurethane material or a device or construct as hereinbefore defined which material or device or construct comprises a polyurethane polymer network having a hydrophilic polymer immobilised therein wherein the hydrophilic polymer comprises bacteria or pH detecting or sensing ligand or species and comprises indicator wherein indicator provides a first indication prior to contact with the wound and changes indication as a function of detecting bacteria, for example as a function of binding and optionally of type of bacteria.

The wound dressing may comprise any features of the device as herein described.

For example ligand or species may comprise function such as type-specific bacterial or pH detecting, sensing or binding function Preferably a wound dressing comprises (a) conformable elastomeric apertured film, (c) an intermediate conformable hydrophilic foam layer, and (b) a continuous moisture vapour transmitting conformable polymer film outer layer in which the layers are attached in a contiguous and co-extensive relationship. In this embodiment a device or wound dressing may comprise a modification of commercially available absorbent foam, woven or non-woven fiber or mesh, film or membrane, or wound dressing comprising absorbent foam, woven or non-woven fiber or mesh, film or membrane such as polyurethane foam. Polyurethane foams or polyurethane foam dressings which might beneficially incorporate the polyurethane material as hereinbefore defined include ALLEVYN™ foam, ALLEVYN™ Adhesive, ALLEVYN™ Gentle Border, ALLEVYN™ Gentle, ALLEVYN™ Ag Gentle Border, ALLEVYN™ Ag Gentle, PICO™ and other commercially available absorbent, hydrophilic polyurethane foams based on polyurethane polyol moieties, most particularly being compatible with the method of generating the polyurethane material as hereinbefore defined.

FIG. 6A depicts a device 100 having a wound-contacting surface 102 and an opposing non-wound-contacting surface 104. FIG. 1B depicts the device 100 in situ on a wound 106. The device 100 can be made of any material that is suitable for contact with the wound. Wound contact layers are known in the art and include the PROFORE wound contact non-adherent dressing (Smith and Nephew, Inc), the MEPITEL Soft Silicone Wound Contact Layer (MÖInlycke Health Care US, LLC), CUTICERIN, a low-adherent acetate gauze (Smith and Nephew, Inc) and the DRYNET Wound Veil (Smith and Nephew, Inc).

Preferably a wound contact layer is characterised by being a conformable, transparent, non-adherent porous sheet for placing on or in an open wound bed to protect the tissue from direct contact with other agents or dressings applied to the wound.

Preferably a wound contact layer is porous to allow wound exudate to pass through for absorption by an overlying, secondary dressing. Device 100 may be porous and can be a made of a non-woven, a perforated film or a mesh. Alternatively, in applications in which the device 100 is to be transiently placed into the wound to detect pH or microbes between dressing changes, the device 100 may be non-porous.

Preferably a wound contacting surface 102 surface comprises a border region for sealing to skin about the wound.

A non wound contacting surface 104 may comprise an obscuring layer. Alternatively a non wound contacting surface 104 or part thereof may be transparent to permit inspection of the wound contacting surface 102, for example may comprise a window or aperture in the obscuring layer or a plurality of windows or apertures.

The device further includes a polyurethane material as hereinbefore defined 108 which comprises or is applied as layer to one or both of surfaces 102 (shown in FIG. 6.1) and/or 104 or intermediate therebetween or which comprises device 100.

Suitably the material is provided as a sheet or layer so that it is not washed away by the wound exudate.

In embodiments on which the polyurethane material comprises only one surface of a non-porous device, then an indication, for indicating which side the material is comprised on may be provided. This indication allows the user to appropriately orient the device during placement on or in a wound to ensure that the correct surface provides the wound-contacting surface.

The polyurethane material may be applied across substantially the entire surface 102 and/or 104, to allow the detection across the entire wound bed to be mapped. Alternatively, the polyurethane material may be applied to discrete zones of surfaces 102 and/or 104.

The device may include further orientation marks and optional reference marks to assist in reading the device and identifying, recording and monitoring results. The device may additionally comprise elements of a construct as hereinbefore defined.

The device is further illustrated in FIG. 6.2.1-6.2.3 in the form of a dressing in which FIG. 6.2.1 illustrates layers a) to c) as hereinbefore defined, the polyurethane material provided as layer c), clearly visible as having pink coloration; FIG. 6.2.2 illustrates layers a) to c) as hereinbefore defined, in side elevation view with additional obscuring layer, below which the polyurethane material provided as layer c) is masked, and is visible at the edges only; and FIG. 6.2.3 illustrates the variant of FIG. 6.2.2 in plan view.

The device, wound dressing or bacterial sensor may comprise one or more bacteria binding ligands; preferably comprises one bacteria binding ligand; or comprises at least one gram positive bacteria-binding ligand and at least one gram negative bacteria-binding ligand and comprises indicator for each type specific ligand said ligands providing type specific indication.

In a further embodiment hydrophilic polymer is functionalised by the attachment of at least one gram positive bacteria-binding ligand and at least one gram negative bacteria-binding ligand within any given polymer molecule.

Alternatively an amount of hydrophilic polymer may be functionalised by at least one gram positive bacteria-binding ligand and a further amount of hydrophilic polymer may be functionalised by at least one gram negative bacteria-binding ligand, wherein indication is identified with one or other of respective hydrophilic polymers, for example by zone or location of respective hydrophilic polymers, by nature of indication, for example colour or wavelength or intensity or by type-specificity of indication.

The invention is of particular application in providing a bacteria sensor or wound dressing comprising microbe-responsive polyurethane foam as hereinbefore defined.

In a further aspect there is provided a method for manufacturing a wound dressing as hereinbefore defined comprising providing a sheet of conformable polyurethane material in desired shape and size, and optionally providing together with one or more layers of functional material as a laminar device, preferably together with one or more layers of perforated film, fluid-impermeable film, superabsorbent material and/or fluid distributing material, obscuring material and the like.

Suitably in the manufacture of a device the wound contacting surface and overlying fluid-impermeable membrane have a surface area which is greater than that of an intermediate layers.

Device or polyurethane material as hereinbefore defined may be sterile, and more particularly terminally sterile, as known in the art. Preferably such device or material is provided within sterilised primary packaging. Suitably the method includes optional sterilisation in known manner and packaging. Sterilisation is suitably for example by radiation such as gamma or ebeam radiation, or by thermal sterilisation.

In a particular advantage we have found that the materials and device may be provided in sterile or terminally sterile form, without deleterious effect thereon.

Suitably the method is a method for manufacture of a laminar wound dressing, for example an ALLEVYN or PICO dressing as hereinbefore defined or as known in the art.

Kit

In a further aspect there is provided a kit comprising at least one device as hereinbefore defined, the kit further comprising a reference strip providing reference information for processing information relating to indication and change in indication and generating output information relating to bacteria or pH.

Preferably a reference strip provides information to calibrate the device. For example a references strip will calibrate the device to pick up the desired wavelength of fluorescence emission and correct as necessary for processing acquired wavelength information.

A reference strip may alternatively be provided integral with material or a device or dressing as herein defined.

The device may be intended for visual inspection or inspection with use of a suitable inspection or scanning device or reader.

Inspecting or Scanning Device or Reader (Interfacing Device)

In a further aspect of the invention there is provided an inspection or scanning device or reader for example for inspecting or scanning or reading a sensing and/or detecting device, for example a device as hereinbefore defined, receiving information relating to indication or change in indication and providing output information relating to chemical or biological species or stimulus such such as microbes or pH present at a locus, the device comprising interrogation means for acquiring indicating information;

a processor for processing indicating information and generating output information, and a display or connectivity for a display for displaying output information.

Interrogation means herein is may conveniently be described as a sensor or detector, and preferably comprises a light sensor. Light sensors are known in the art and include for example charge coupled devices (CCDs) and active pixel sensors in complementary metal-oxide semiconductors (CMOS).

Interrogation means or sensor or detector may further comprise recording means such as a camera.

Interrogation means or sensor or detector is suitable for the indicating information to be acquired.

In the case that indicating information is a fluorescence signal, interrogation means or sensor or detector may additionally comprise an excitation light source. An excitation light source has the purpose of providing excitation light to fluorescent indicating means for the generation of fluorescence information, such as fluorescence emission in the form of a fluorescence reading or fluorescence signal as hereinbefore defined.

An emission filter may further be provided, suitably for the purpose of eliminating excitation light. Emission filters are known in the art of observing fluorescence. Preferably an emission filter allows passage of light in a narrow bandwidth of for example 635-660 nm, around a central wavelength for example 647 nm.

A fluorescence chamber may additionally be provided for the purpose of containing the excitation light source and an emission filter if present. A fluorescence chamber provides a controlled lighting environment for delivery of excitation light to the sensing device, receipt of emission light therefrom and control of ambient light. Preferably the fluorescence chamber excludes ambient light which might obscure excitation and emission light. The fluorescence chamber may be separate or integral with the interfacing device, a separate chamber for example may comprise a housing to receive the material.

A fluorescence chamber may be a closed chamber adapted to receive the material or comprise a skirt adapted to be located over the material Preferably a skirt is conformable or flexible. A conformable or flexible skirt may be located over material in situ at a locus and conform to the profile of the material and/or locus to exclude ambient light. In the case of wound management, a locus may be a body part of irregular shape.

A light source may be selected from one or more lasers, LEDs and the like. Light sources may emit light at same or different wavelengths. A light source may be associated with one or more filters allowing the desired wavelength emission.

A light source may comprise a light source for emission of broad spectrum light, together with an emission filter for selection of a desired wavelength excitation light, or may comprise one or more light sources for emission of a narrow bandwidth light, such as a specific narrow bandwidth light or a narrow bandwidth of a desired wavelength. For example a light source may comprise one or more LEDs emitting light in a narrow bandwidth around a central wavelength.

Preferably a light source emits light at a wavelength corresponding to the excitation wavelength of the indicating means. A suitable wavelength may be for example in the range 590 nm. Preferably the light source emits light in a narrow bandwidth of for example 580-600 nm around a central wavelength for example 590 nm.

A processor includes means to receive acquired indicating information, means to access software for processing acquired information and means to output processed information.

Means to receive acquired indicating information may comprise a wireless or wired connection. Means to access software may comprise an integral or external memory programmed with software, or internet access to remote software or a combination thereof.

A display may be an optical or digital display. A display suitably provides processed output information in optical or digital format. Preferably a display is a visual display unit for displaying digital images, digital quantitative read out or digital text. Text may for example include instructions to the user such as "infected", "take action", "see specialist" or the like.

Conveniently a display is a display comprised in a camera which combines light detector and display in a single unit.

A display may be integral with or remote and separate from the inspection or scanning device or reader. For example the scanning device or reader may be a mobile phone or other hand held with integral display adapted to be received within the fluorescence chamber. Alternatively or additionally a display is a remote display, for example the device may provide output information to a remote display, and may comprise means to transmit output information for display. In the case of a remote display, the device comprises connectivity for a remote display, for example a socket for a wired communication cable, a socket for a communications mounting or cradle, or wireless connection means such as Bluetooth, telecoms systems, wifi or other suitable means. A remote display may comprise one or more of a VDU, TV console (optionally wall mounted), printer, a component of the material or a construct comprising the material and the like. Variants are innumerable and well known in the art of visual displays, computing and telecommunications.

Preferably an interfacing device is mobile, more preferably is hand held.

Conveniently a mobile hand held interfacing device comprises a smart phone optionally together with an excitation light source and fluorescence chamber as hereinbefore defined. Software may be provided in the form of an App whereby external software access is not required. The App may capture and process an image of the indicating information such as emission fluorescence.

The inspection and/or scanning device or reader may comprise means such as a dock, panel or slot to receive the detection and/or sensing device and directly download information relating to indication or change in indication therefrom.

Processed output information may be in the form of a map, such as a map of fluorescence intensity or a "heat map", optionally calibrated against a fluorescence intensity reference or control.

Processed output information optionally includes location and/or orientation information, subject information for example patient information, date and the like. Processed output information may be overlaid on or otherwise compared with processed output information relating to the same or different locus.

In a further aspect there is provided a kit comprising two or more components of an inspection or scanning device or reader as hereinbefore defined.

In a further aspect there is provided a method for inspecting or scanning or reading a sensing and/or detecting device as hereinbefore defined comprising locating an inspection and/or scanning device or reader as hereinbefore defined in relation to the material, activating the inspection and or scanning device to interrogate the detection and/or sensing device and acquire indicating information for processing, optionally additionally to process indicating information, and optionally additionally to record or store, display or transmit for display output information.

The method suitably includes classifying output information as an assessment of wound health. An assessment may be generally classified as deteriorating, stable or improving.

Processed information may be further classified for example as an assessment of localised wound health. An assessment may be generally classified as localised, moderate or extensive health status.

Processed information may be further classified for example as an assessment of localised wound health. An assessment may be generally classified as isolated, moderate or extensive health status.

The method may further comprise determining a treatment plan based on the monitoring or assessment. Treatment may include for example continuing current treatment, increasing current treatment, changing treatment or seek further information on wound health.

A method is illustrated for example in the flow scheme of FIG. 6.3, which illustrates an example of "use of device as indicator on wounds" e.g. clinician decisions resulting from different responses which might be detected.

Method for Detecting or Sensing

In a further aspect there is provided a method for detecting or sensing bacteria or pH at a locus comprising applying material as hereinbefore defined to the locus and interrogating the material to obtain an indication indicating detection or sensing of species, and optionally additionally monitoring for an indication or change in indication.

The method may comprise for example monitoring a stimulus in a subject or locus comprising applying polyurethane material such as stimulus-responsive polyurethane material as hereinbefore defined to the subject or locus and monitoring for a change in stimulus or for a stimulus response.

Interrogating or monitoring may comprise interrogating or monitoring the material directly, for example by means of the indicator.

Alternatively interrogating or monitoring comprises interrogating or monitoring of the material indirectly by means of an optical or digital reading or signal in a device for scanning or interfacing with or inspection of the material, for example with the indicator.

Preferably the method is a method for detecting microbes in or in relation to a subject or locus, comprising applying stimulus-responsive polyurethane material as hereinbefore defined to the subject or locus and monitoring for change in stimulus or for a stimulus response initiated by a microbe-binding event. Microbes are selected from bacteria, fungi and yeast.

Alternatively or additionally the method is a method for detecting pH of or in relation to a subject or locus Method of Treatment In a further aspect there is provided a method for detecting or monitoring a species or stimulus in relation to a subject or locus comprising applying polyurethane material such as stimulus-responsive polyurethane material or species indicating polyurethane material or device as hereinbefore defined to the subject or locus and detecting or sensing an indication as hereinbefore defined or monitoring for an indication or a change in stimulus or for a stimulus response or for interaction or binding of species, for example directly with indicator or indirectly as a result of species binding by ligand.

Monitoring may comprise monitoring the material directly, for example by means of the indicator.

Alternatively monitoring comprises monitoring of the material indirectly by means of an optical or digital reading or signal in a device for scanning or interfacing with the material, for example with the indicator.

Preferably the method is a method for detecting microbes in or in relation to a subject or locus, comprising applying polyurethane material such as stimulus-responsive polyurethane material or species indicating polyurethane material or device as hereinbefore defined to the subject or locus and monitoring for change in stimulus or for a stimulus response initiated by a microbe-binding event or for detection or sensing of species. Microbes are selected from bacteria, fungi and yeast.

In a further aspect there is provided a method for treatment of a subject in need thereof comprising applying polyurethane material such as stimulus-responsive polyurethane material or species indicating polyurethane material or device as hereinbefore defined to the subject and monitoring for change in stimulus or for stimulus response or for sensing or detection of species or stimulus.

Preferably the method is for treatment of a wound in a subject in need thereof, wherein the wound is susceptible to microbial contamination or is suspected of being microbially contaminated, wherein monitoring is for a stimulus response induced by a microbe binding event or wherein monitoring is for interaction or binding of species for example directly with indicator or indirectly as a result of species binding by ligand.

Suitably the method includes interrogating, inspecting or scanning the microbe-responsive polyurethane material to determine binding or proximity of bacteria.

Process for Preparation

Preparation of Stimulus Responsive Polyurethane Material

There is provided a process for the preparation of polyurethane material as hereinbefore defined comprising the formation of a polyurethane network wherein the network formation is conducted in the presence of hydrophilic polymer comprising ligand or moiety and indicator as hereinbefore defined.

Preferably hydrophilic polymer is present during the formation of the network or part thereof. Preferably hydrophilic polymer is present in the process together with an amount of network forming agent, such as chain extending agent or cross linking agent.

The polyurethane network is suitably generated from the product of reaction of polyurethane prepolymers, preferably from the reaction of prepolymers generated by the reaction of isocyanate terminated monomer and long chain diol and/or polyol.

Network forming agent may be introduced simultaneously with or subsequent to reaction of prepolymers.

Network formation suitably comprises cross linking, chain extension or the like.

Preferably the hydrophilic polymer or part or an amount thereof is provided in fluid phase, preferably dissolved in suitable solvent or solvated by a component of the reaction to generate polyurethane. Hydrophilic polymer may be introduced in fluid phase or may adopt fluid phase in situ. Hydrophilic polymer or an amount thereof present in part or fully dissolved or solvated form is able to form an interpenetrating or entangled network with the polyurethane polymer.

Alternatively hydrophilic polymer is provided in solid phase such as in powder form for intimate mixing in a polyurethane reaction component, such as the isocyanate, prepolymer, aqueous phase, for example a HYPOL component, a diol component or the like, optionally together with an amount of added solvent for the hydrophilic polymer. Intimate mixing into a non-aqueous component may be conducted with simultaneous or subsequent addition of an aqueous component. Hydrophilic polymer or part or an amount thereof is thereby dissolved in the reaction component. Intimate mixing moreover provides hydrophilic polymer distributed throughout the resulting polyurethane material.

The process may comprise introducing a plurality of hydrophilic polymers as hereinbefore defined simultaneously or in sequence.

Suitably the hydrophilic polymer is combined with one or more polyurethane components prior to extrusion or casting of the combined polyurethane reaction components. Casting may be into a mould or onto a surface as known in the art. Extrusion or casting is suitably in manner to form a foamed or non foamed block or sheet, gel, membrane or film, or string, ribbon, thread or like fiber form.

It is one benefit of the invention that hydrophilic polymer may be simply blended with the polyurethane components or ingredients during the reaction thereof and prior to chain extension or crosslinking, whereby it is immobilised within the polyurethane network. Hydrophilic polymer may be blended with one of the polyurethane components or ingredients prior to combining the respective components or ingredients. For example hydrophilic polymer may be combined with an isocyanate component or polyol component or both such as the HYPOL phase or the long chain diol and/or polyol phase in a polyurethane system.

The process may be a process for preparing a foam, xerogel, film or other non-foamed material as hereinbefore defined.

There is a balance between a low water content gel necessary to preserve the immobilisation of hydrophilic polymer and the presence of water to assist in dissolving hydrophilic polymer and enable network interpenetration or entanglement. Polyurethane material may be cast, such as cast from solvent, or extruded into the above forms as known in the art.

The process may be a process for preparing stimulus-responsive polyurethane material as hereinbefore defined, preferably comprising polymerisation reaction of aromatic isocyanate monomer and long chain diol and/or polyol as hereinbefore defined, including optional step growth polymerisation, and chain extension or cross linking thereof, wherein part or all of the process is conducted in the presence of one or more highly branched hydrophilic polymer as hereinbefore defined.

The reaction may be aqueous or non aqueous.

The reaction may conveniently be illustrated in non-limiting manner as follows in Scheme a1:

Scheme a1

Polyurethane material is obtained by step growth polymerisation of diisocyanate with polyol as hereinbefore defined in the presence of hydrophilic polymer (I) as hereinbelow defined:

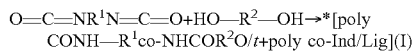

wherein $R^1$ is aromatic hydrocarbyl for example selected from toluene, methylenediphenyl, paraphenylene and naphthyl;

$R^2$ is selected from alkyl, polyester, polycaprolactone, polyether and polycarbonate;

* is highly branched hydrophilic polymer or linear hydrophilic polymer as hereinbelow defined and /t indicates terminal or in chain polymer moieties.

Preferably the process comprises step growth polymerisation as hereinbefore defined generating the corresponding isocyanate terminated oligomeric prepolymer which is simultaneously or subsequently crosslinked or chain extended. This reaction may conveniently be illustrated in non-limiting manner as follows in Scheme a2:

Scheme a2

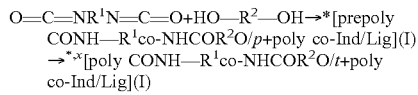

wherein variables are as hereinbefore and hereinbelow defined and

/p indicates terminal or in chain prepolymer moiety which may be the same as or different to /t; and X=crosslinker or chain extender as hereinbefore or hereinbelow defined.

Scheme a2 may be conducted as two separate steps or as a single step in which crosslinker or chain extender x is present throughout.

Polymerisation may be performed using any suitable method for example solution, suspension, emulsion and bulk polymerisation methods may all be used.

The process suitably comprises blending, optionally casting or extruding, optionally foaming, and curing as required. Preferably curing is initiated by mixing of the components Contacting may be in the presence of optional initiator, catalyst, blowing agent or foaming agent, surfactant, chain extender, cross-linker and the like as known in the art.

The polyurethane foam is suitably generated with the use of surfactants to regulate cell size and prevent collapse.

Where it is desired to prepare a foam, the process may generate foaming agent in situ. Alternatively or additionally foaming agent may be added. In situ generated foaming agent includes $CO_2$ gas generated from reaction of water and isocyanate. Added foaming agent includes $N_2$ gas and volatile liquids such as HFC-245fa (1,1,3,3-pentafluoropropane) and HFC-134a (1,1,1,2-tetrafluoroethane), and hydrocarbons such as n-pentane and the like.

Chain extenders (f=2) and cross-linkers (f=3 or greater) are suitably selected from low molecular weight hydroxyl and amine terminated compounds, as known in the art. Crosslinking agent may be selected from cross linking agents used in the preparation of foams, such as water or the like.

Polyol is commercially available in a resin or blend incorporating catalyst, surfactant, chain extender and/or cross-linker.

The process may be conducted at ambient temperature or at elevated temperature if it is desired to increase the rate of chain transfer. Preferably the process is conducted at ambient temperature up to 40 C. Elevated temperature is suitably in the range in excess of 100 C, preferably from 125 to 175 C.

The product polyurethane material, for example [poly CONH—$R^1$ co-NHCO $R^2$O/t+poly co-Ind/Lig] (I), is suitably isolated from reaction medium without need for further working up. If desired however the process may optionally include in a further step washing or extraction in an aqueous solvent for the polymer, to remove residual non immobilised polymer. This may be useful in the case that hydrophilic polymer is present in a wide diversity of molecular weight, branching functionalisation or the like, whereby some polymer is entrained but is not immobilised. Preferably washing or extraction is with any solvent for the hydrophilic polymer, preferably selected from ethanol, aqueous ethanol, $CH_2Cl_2$, acetone and DMSO. Known techniques may be employed such as a series of solvent bath, nip roller and oven. Preferred solvent is aqueous ethanol. Drying may be in excess of ambient temperature for example about 60 C.

The process is illustrated in non-limiting manner in FIG. 1.

Suitably the process comprises in a previous step the preparation of highly branched hydrophilic polymer as hereinbefore defined.

Preparation of Highly Branched Hydrophilic Polymer.

Preparation of highly branched hydrophilic polymer such as PNIPAM is known in the art and suitably comprises preparation from monomers of the aforementioned poly acrylamide, polyalkyl acrylamide, polyacrylate, polymethacrylate, polyacrylic acid, polymethacrylic acid, polyvinyl ether. poly vinyl caprolactam and copolymers thereof. Preparation is suitably as illustrated in FIG. 1.

Hydrophilic polymer is conveniently prepared by known radical polymerisation processes.

Preferably the polymer is prepared by controlled radical polymerisation, more preferably by reversible addition-fragmentation chain-transfer polymerisation (RAFT) employing a RAFT agent.

A RAFT agent may be selected from polymerisable dithioesters as commercially available. A RAFT agent is preferably a dithioate or dithioester such as of formula Z—C(=S)—S—R wherein Z and R are organic groups.

Suitably the radical polymerisation reaction to prepare hydrophilic polymer is conducted in the presence of indicator, such as Nile Red. This is also illustrated in FIG. 1. Nile Red is by this means incorporated in the polymer branches in desired ratio and location.

The process may be conducted at ambient temperature or at elevated temperature if it is desired to increase the rate of chain transfer. Preferably the process is conducted at elevated temperature in the range from ambient temperature up to 90 C for example of the order of 55 to 65 C.

The thus prepared polymer incorporating indicator is suitably further reacted to introduce reactive end groups for covalent bonding to ligand for binding and/or detection of species, for example vancomycin or polymyxin. Reactive end groups are suitably selected from succinimide, generated by reaction with N-hydroxy succinimide and dicyclohexyl carbodiimide.

The reaction may conveniently be illustrated in non-limiting manner as follows in Scheme b (i)-(iii):

In step i) Functional indicator copolymer (I) is obtained from hydrophilic polymer-indicator-copolymer (II):

Scheme b (i)

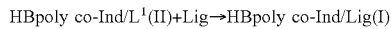

HBpoly co-Ind/L$^1$(II)+Lig→HBpoly co-Ind/Lig(I)

wherein

HBpoly indicates highly branched polymer as hereinbefore defined such as HBpolyNIPAM;

Ind is an indicator as hereinbefore defined such as Nile Red (NR);

co-indicates a copolymer of poly and Ind;

L$^1$ is reactive functionality such as succinimide moiety;

/ indicates one or more terminal moieties; and

Lig represents functional ligand as hereinbefore defined.

Preferably in step ii) reactive hydrophilic polymer-indicator-copolymers (II and II') are obtained by interconversion from hydrophilic polymer-indicator-RAFT polymer (III)

Scheme b (ii)

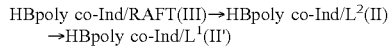

HBpoly co-Ind/RAFT(III)→HBpoly co-Ind/L$^2$(II)
→HBpoly co-Ind/L$^1$(II')

wherein HBpoly, co-, Ind, /, RAFT and L$^1$ are as hereinbefore defined and

L$^2$ is reactive functionality such as carboxylic acid moiety.

Preferably in step iii) hydrophilic polymer-indicator-RAFT polymer (III) is obtained by radical polymerisation from monomer (IV) and RAFT agent (V) in the presence of reactive Indicator (VI):

Scheme b (iii)

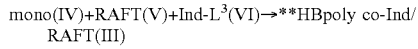

mono(IV)+RAFT(V)+Ind-L$^3$(VI)→**HBpoly co-Ind/RAFT(III)

wherein Ind, HBpoly, co- and/are as hereinbefore defined; and mono is any monomer for preparing hydrophilic polymer as hereinbefore defined;

RAFT is any suitable dithioate or dithioester such as eg 4-vinylbenzyl-pyrrolecarbodithioate;

L$^3$ is reactive functionality such as acrylate;

** is initiator such as AVCA as hereinbefore defined.

Conditions are as described above and as known in the art.

If it is desired to introduce indicator towards or at chain ends, in a variant of scheme b, Ind is introduced during or after step iii).

The process is further illustrated in non-limiting manner in FIG. 1a.

Preparation of Linear Hydrophilic Polymer.

Preparation of linear hydrophilic polymer such as PNIPAM is known in the art and suitably comprises polymerisation from monomers of the aforementioned poly acrylamide, polyalkyl acrylamide, polyacrylate, polymethacrylate, polyacrylic acid, polymethacrylic acid, polyvinyl ether. poly vinyl caprolactam and copolymers thereof.

Polymerisation is suitably conducted together with agent for attachment of functional ligand. Attachment agent is conveniently introduced pendant to the linear polymer chain, for example is introduced in the form of a pendant copolymer with the above monomer.

Attachment agent is for example vinyl benzoic acid (VBA)

Initiator for the polymerisation reaction may be present, and is suitably selected from AVCA.

Suitably the reaction to prepare linear polymer is conducted in the presence of indicator, such as Nile Red. Nile Red is thus incorporated along the polymer chain, pendant thereto in desired ratio as hereinbefore defined.

The process may be conducted at ambient temperature or at elevated temperature if it is desired to increase the rate of chain transfer. Preferably the process is conducted at elevated temperature in the range from 40 C up to 80 C, for example of the order of 55 to 65 C.

The linear polymer incorporating indicator and attachment agent is suitably interconverted to form for covalent bonding to ligand, for example vancomycin or polymyxin. Interconversion suitably replaces attachment agent with reactive groups selected from succinimide, generated by reaction with N-hydroxy succinimide and dicyclohexyl carbodiimide.

The reaction may conveniently be illustrated in non-limiting manner as follows in Scheme b (i)-(iii):

In step i) hydrophilic polymer-indicator-ligand copolymer (I) is obtained from hydrophilic polymer-indicator-copolymer (II)

Scheme b (i)

Lpoly co-Ind-co L$^1$(II)+Lig→Lpoly co-Ind-co-Lig(I)

wherein

Lpoly indicates linear polymer as hereinbefore defined such as LpolyNIPAM;

Ind is an indicator as hereinbefore defined such as Nile Red (NR);

co—indicates a copolymer;

L$^1$ is reactive functionality such as succinimide moiety; and

Lig represents functional ligand as hereinbefore defined.

Preferably in step ii) reactive hydrophilic polymer-indicator-copolymer (II) is obtained by interconversion from hydrophilic polymer-indicator-attachment agent (III)

Scheme b (ii)

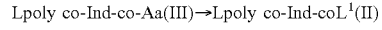

Lpoly co-Ind-co-Aa(III)→Lpoly co-Ind-coL$^1$(II)

wherein Lpoly, co-, Ind, and L$^1$ are as hereinbefore defined and

Aa is attachment agent such as VBA.

Preferably in step iii) hydrophilic polymer-indicator-attachment agent (III) is obtained by polymerisation from monomer (IV) and attachment agent (V) in the presence of reactive Indicator (VI):

Scheme b (iii)

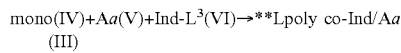
(III)

wherein Ind, Lpoly, Aa, co- are as hereinbefore defined; and mono is any monomer for preparing hydrophilic polymer as hereinbefore defined;

Aa is any suitable attachment agent such as VBA;

$L^3$ is reactive functionality such as acrylate;

** is initiator such as AVCA as hereinbefore defined.

Conditions are as described above and as known in the art.

If it is desired to introduce indicator towards or at chain ends, in a variant of scheme b, Ind is introduced during or after step iii).

The process is illustrated in non-limiting manner in FIG. 1*b*.

A number of classes of hydrophilic polymers may be produced:
I. Linear polymers with pendant indicator
II. Highly branched polymers with pendant indicator through out the polymer
III. Highly branched polymers with indicator in inner chain segments
IV. Highly branched polymers with indicator in outer linear segments
V. Highly branched polymers with indicator in outer branched segments
VI. Highly branched polymers with indicator attached to the chain ends Indicator is preferably selected from Nile Red and Nile Blue Here each class shows the existence of the indicator in a different location across the polymer chain, this indicator can be used to show the specific environment across that part of the polymer. Nile blue present in Class VI may equally be used as a substitute for nile red in other classes.

The linear polymers (class I) were prepared by copolymerizing NIPAM, nile red acrylate and vinyl benzoic acid. Then the carboxylic acid groups were modified by reaction with vancomycin (pH$_9$) via the N-hydroxy succinimide (NHS) ester. The highly branched polymers were produced using modifications of the technique illustrated in FIG. 1.3. These class II polymers were prepared by copolymerizing NIPAM, nile red acrylate and 4-vinylbenzyl-pyrrolecarbodithioate (VBP), followed by modification of the end groups to carboxylic acid and then conjugation of vancomycin, via the NHS ester, to the end groups.

Class III, IV and V polymers were prepared by a stepwise chain extension of HB-PNIPAM: i.e. in step 1 a polymerization similar to class II polymerization was performed then in step 2 a second monomer feed was polymerized by transfer to the dithioate chain ends that are produced in the SCVP-RAFT process. In class III polymers nile red acrylate was included in the first step and not in the second step, class IV polymers included nile red acrylate only in second step polymerization that the branching monomer (VBP) and in class V the second step monomer feed included nile red acrylate, NIPAM and VBP. Class VI polymers were made by attachment of Nile Blue to succinimide polymer chain ends via the NHS coupling reaction.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

The invention is now illustrated in non-limiting manner by the following Examples and Figures.

EXAMPLES

1. Hydrophilic (highly branched (HB), linear (L) or extended (combined branch ratio or combined HB/L)) copolymer was polymerised incorporating dye (Nile Red, dansyl etc.) label along the polymer chain and functionalised by having branch or linear termini functionalised with antibiotics vancomycin and/or polymyxin.

2. Hydrophilic (highly branched, linear, or extended) polymer was then mixed in with polyurethane prepolymer (polyol and isocyanate) under step growth polymerisation conditions with foaming.

3. Subsequent extraction studies were conducted to determine whether hydrophilic polymer leached from, or indeed could be extracted from, the thus formed PU foam. Nile Red label facilitated visualisation of HB polymer in relation to the polyurethane foam and to extraction washings isolated from the foam.

1. Synthesis of Highly Branched and Highly Branched Extended Copolymers 1.1 Synthesis of 4-Vinylbenzyl-Pyrrolecarbodithioate (RAFT Agent)

Sodium hydride (11.92 g) was added to a dry 500 ml three necked round bottomed flask together with 160 ml DMF. Pyrrole (20 g) in 10 ml DMF was added to the rapidly stirring mixture over a 30 minute period. The mixture was stirred for a further 30 minutes and then cooled to 0 C in an ice bath. Carbon disulphide (18 ml) in 10 ml DMF was added dropwise over 10 minutes and the solution stirred for 30 minutes and then cooled to 0 C. 4-vinyl benzoic acid (45.48 g) in 10 ml DMF was added dropwise over 20 minutes and the mixture stirred overnight at room temperature. The mixture was split in two and transferred to a separating funnel and 80 ml diethyl ether and 80 ml water added. The organic layer was recovered and the aqueous layer extracted 3 times with ether. This process was repeated for the other half and ether extracts were combined and dried with magnesium sulphate. The solvent was removed by rotary evaporation to give a red/brown oil. The crude RAFT agent was purified by column chromatography using petroleum spirit 40-60 C as the eluent. The solvent was removed by rotary evaporation to give a bright yellow oil that solidifies around room temperature. The yield was typically ~50-60%.

1.2 Synthesis of Nile Red Acrylate (5-Diethylamino)-2-Nitrosophenol Hydrochloride 3-Diethylaminophenol (5 g) was dissolved in a mixture of concentrated HCl (11 ml) and water (6 ml) and cooled on ice. A solution of sodium nitrite (2.1 g) in water (35 ml) was added dropwise over 1 hour and the resulting slurry stirred on ice for a further 2 hours. The crude product was dissolved in boiling ethanol and recrystallized with diethyl ether to yield a yellow/orange solid (3.7 g, 50% yield). Mass spectrometry found m/z=195, expected 195.

9-Diethylamino-2-hydroxy-5H-benzo[R]phenoxazin-5-one Hydroxy Nile Red

5-Diethylamino-2-nitrosophenol hydrochloride (1.5 g) and 1,6-dihydroxynaphthalene (1.05 g,) were dissolved in DMF (180 ml) and refluxed for 7 hours. The solvent was removed and the residue purified by silica gel column chromatography (petroleum spirit:ethyl acetate 20%-100%) yielding 0.52 g (20%) of a dark blue solid. $^1$H NMR in DMSO d6: ▢ =10.4 (1H, s), 7.95 (1H, d), 7.88 (1H, d), 7.6 (1H, d), 7.08 (1H, d), 6.8 (1H, d), 6.6 (1H, d), 6.15 (1H, s), 3.5 (4H, q), 1.18 (6H, t). Mass spectrometry found m/z=335, expected 335.

Nile Red Acrylate

Hydroxy nile (0.5 g) was dissolved in dichloromethane (140 ml) and triethylamine (870 ml) and acryloyl chloride (500 ml) added. The solution was stirred at room temperature for 7 hours. Solvent was removed and the residue purified by silica gel column chloromatography (petroleum spirit:ethyl acetate (2:1) yielding 0.2 g (34%). $^1$H NMR in DMSO d6: ▢ =8.3 (1H, d), 8.2 (1H, d), 7.6 (1H, d), 7.5 (1H, d), 6.85 (1H, d), 6.75 (1H, d), 6.6 (1H, d), 6.5 (1H, q), 6.3 (1H, s), 6.2 (1H, d), 3.5 (4H, q), 1.2 (6H, t). mass spectrometry found m/z=389, expected 389.

1.3 Highly branched PolyN-isopropyl acrylamide by RAFT polymerisation

HB-PNIPAM was prepared with different degrees of branching as follows:

1.3.1 15:1 NIPAM:RAFT Agent, Nile Red Copolymer 10 g N-isopropyl acrylamide, 1.53 g RAFT agent (1.1 above), 1.65 g 4,4'-azobis(4-cyanovaleric acid (ACVA, initiator), 0.02 g nile red acrylate dissolved in 50 ml dioxane were added to a glass ampule. Following degassing the ampule was flame sealed and placed in a waterbath at 60 C for 48 hours. The polymer was obtained by precipitation into diethyl ether and filtered to give a pink powder.

1.3.2 25:1 NIPAM:RAFT Agent, Nile Red Copolymer (0.2% and 0.4% Nile Red)

10 g N-isopropyl acrylamide, 0.91 g RAFT agent, 0.99 g ACVA, 0.02 g nile red acrylate dissolved in 50 ml dioxane were added to a glass ampule. Following degassing the ampule was flame sealed and placed in a waterbath at 60 C for 48 hours. The polymer was obtained by precipitation into diethyl ether and filtered to give a pink powder.

The corresponding copolymer 1.3.2.1 was prepared in the same manner using 0.04 g nile red acrylate.

1.3.3 45:1 NIPAM:RAFT Agent, Nile Red Copolymer 10 g N-isopropyl acrylamide, 1.53 g RAFT agent, 1.65 g ACVA, 0.02 g nile red acrylate dissolved in 50 ml dioxane were added to a glass ampule. Following degassing the ampule was flame sealed and placed in a waterbath at 60 C for 48 hours. The polymer was obtained by precipitation into diethyl ether and filtered to give a pink powder.

1.3.4 Synthesis of Highly Branched Extended Copolymers 1.3.4.1 15:1NIPAM:RAFT Agent Core, 15:1 NIPAM:RAFT Agent Nile Red Outer Extended Copolymer The corresponding copolymer with Nile Red in the outer only was prepared from 5 g 15:1 NIPAM:RAFT copolymer obtained using the methodology 1.3.1 above modified by omission of Nile Red, combined with 5 g N-isopropyl acrylamide, 0.77 g RAFT agent and 0.83 g ACVA, and 0.01 g Nile Red.

1.3.4.2 25:1 NIPAM:RAFT Agent Core, 25:1 NIPAM:RAFT Agent Nile Red Outer Copolymer The corresponding copolymer with Nile Red in the outer only was prepared from 5 g 25:1 NIPAM:RAFT polymer obtained using the methodology 1.3.2 above modified by omission of Nile Red, combined with 5 g NIPAM, 0.45 g RAFT agent, 0.5 g ACVA and 0.01 g nile red acrylate.

1.3.5 Synthesis of Copolymers with Variant Dyes 1.3.5.1 NIPAM:RAFT Agent, Dansyl Copolymer The corresponding copolymer with Dansyl was prepared by analogy with the above methodologies, using dansyl acrylamide in place of nile red acrylate.

1.3.6 Synthesis of Copolymers with Variant Monomers 1.3.6.1 25:1 EPAM:RAFT Agent, Nile Red Copolymer The corresponding copolymer with ethyl acrylamide monomer was prepared by analogy with the above methodology (1.3.2) using ethyl acrylamide in place of n-isopropyl acrylamide.

1.3.6.2 25:1 (EPAM/NIPAM 50/50):RAFT Agent, Nile Red Copolymer

The corresponding copolymer with ethyl acrylamide monomer was prepared by analogy with the above methodology (1.3.2) using ethyl acrylamide in place of n-isopropyl acrylamide.

1.4 Synthesis of Linear and Linear Extended Copolymers 1.4.1 Linear Polymer; Copolymer of N-Isopropyl Acrylamide and Vinyl Benzoic Acid and Nile Red 6 g N-isopropyl acrylamide, 0.31 g vinyl benzoic acid, 0.155 g ACVA, 0.012 g nile red acrylate dissolved in 37 ml dioxane, 7.5 ml dimethyl formamide were added to a glass ampule. Following degassing the ampule was flame sealed and placed in a waterbath at 60 C for 48 hours. The polymer was obtained by precipitation into diethyl ether and filtered to give a pink powder.

1.4.2 25:1NIPAM:RAFT Agent Core, Linear Nile Red Outer Extended Copolymer

The corresponding copolymer with branched core and linear outer with Nile Red in the outer only was prepared from 6 g 25:1 NIPAM:RAFT polymer obtained using the methodology 1.3.2 above modified by omission of Nile Red, combined with 6 g NIPAM, 0.31 g vinyl benzoic acid, 0.155 g ACVA and 0.012 g nile red acrylate using the methodology of 1.4.1 above.

1.5 Attachment of Vancomycin to Polymers 1.5.1 Attachment to 15:1 Polymer

Conversion of Chain Ends to Carboxylic Acid 3 g of RAFT polymer was dissolved in 25 ml DMF and heated to 65 C. Three additions of ACVA (10 g on each occasion) were made over 72 hours after which time the polymer was recovered by precipitation into diethyl ether and further purified by ultrafiltration. After rotary evaporation a red solid was obtained.

Conversion of Chain Ends to Succinimide.

1.5 g carboxylic acid terminated polymer was dissolved in 20 ml DMF. 0.4225 g N-hydroxy succinimide and 0.453 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 200 mg of succinimide derivatised polymer was dissolved in 10 ml water over ice and 120 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.2 Attachment to 25:1 Polymer

Conversion of Chain Ends to Carboxylic Acid 3 g of RAFT polymer was dissolved in 25 ml DMF and heated to 65 C. Three additions of ACVA (5.9 g on each occasion) were made over 72 hours after which time the polymer was recovered by precipitation into diethyl ether and further purified by ultrafiltration. After rotary evaporation a red solid was obtained.

Conversion of Chain Ends to Succinimide.

1.5 g carboxylic acid terminated polymer was dissolved in 20 ml DMF. 0.255 g N-hydroxy succinimide and 0.453 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 250 mg of succinimide derivatised polymer was dissolved in 10 ml water over ice and 100 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.3 Attachment to 45:1 Polymer

Conversion of Chain Ends to Carboxylic Acid 3 g of RAFT polymer was dissolved in 25 ml DMF and heated to 65 C. Three additions of ACVA (3.24 g on each occasion) were made over 72 hours after which time the polymer was recovered by precipitation into diethyl ether and further purified by ultrafiltration. After rotary evaporation a red solid was obtained.

Conversion of Chain Ends to Succinimide.

1 g carboxylic acid terminated polymer was dissolved in 15 ml DMF. 0.094 g N-hydroxy succinimide and 0.1.66 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 250 mg of succinimide derivatised polymer was dissolved in 10 ml water over ice and 112 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.4 Attachment to Linear polyNIPAM-Co-VBA

Conversion of Carboxylic Acid Groups to Succinimide 1.5 g of polymer was dissolved in 20 ml DMF. 0.255 g N-hydroxy succinimide and 0.453 g dicyclohexyl carbodiimide in 5 ml in DMF was added and the solution stirred for 24 hours after which the polymer was precipitated in diethyl ether and ultra filtered. After rotary evaporation a red solid was obtained.

Attachment of Vancomycin 300 mg of succinimide derivatised polymer was dissolved in 10 ml water over ice and 135 mg vancomycin dissolved in 5 ml water, 5 ml phosphate buffered saline pH8.5 added and the pH adjusted to 10. After 48 hours at 4 C the polymer was purified by ultrafiltration and freeze dried to give a pink solid.

1.5.5 Attachment to Extended Copolymers with Variant Dyes 1.5.5.1 15:1 NIPAM:RAFT Agent Core, 15:1 NIPAM:RAFT Agent Nile Red Outer Copolymer The copolymer 1.3.4.1. was derivatised with vancomycin in the same way as copolymer 1.5.1 above to give vancomycin chain ends.

1.5.5.2 25:1 NIPAM:RAFT Agent Core, 25:1 NIPAM:RAFT Agent Nile Red Outer Copolymer The copolymer 1.3.4.2. was derivatised with vancomycin in the same way as copolymer 1.5.2 above to give vancomycin chain ends.

1.5.5.3 25:1NIPAM:RAFT Agent Core, Linear Nile Red Outer Extended Copolymer

The copolymer 1.4.2. was derivatised with vancomycin in the same way as copolymer 1.5.4 above to give vancomycin chain ends.

1.5.6 Attachment to Copolymers with Variant Dyes 1.5.6.1 NIPAM:RAFT Agent, Dansyl Copolymer The copolymer 1.3.5.1 was derivatised with vancomycin in the same way as copolymers 1.5 above to give vancomycin chain ends.

1.5.7 Attachment to Copolymers with Variant Monomers 1.5.7.1 25:1 EPAM:RAFT Agent, Nile Red Copolymer The copolymer 1.3.6.1 was derivatised with vancomycin in the same way as copolymer 1.5.2 above to give vancomycin chain ends.

1.5.7.2 25:1 (EPAM/NIPAM 50/50):RAFT Agent, Nile Red Copolymer

The copolymer 1.3.6.2 was derivatised with vancomycin in the same way as copolymer 1.5.2 above to give vancomycin chain ends.

1.6. Attachment of Polymyxin to Polymers

Modification of Polymyxin B Sulphate 200 mg fluoronylmethyloxycarbonyl chloride FMOC (200 mg) was added to 5 ml 1M sodium carbonate solution and mixed with 500 mg polymyxin sulphate B dissolved in 10 ml water and stirred for 24 hours. The resulting solid was filtered and washed with water and then dried. 200 mg of FMOC-polymyxin in 20 ml TRIS buffer was mixed with 8 mg polymyxin acylase in 8 ml phosphate buffered saline pH8 and stirred overnight. The product was filtered and washed with water.

Attachment of polymyxin to hyperbranched polymers with succinimide derivatised chain ends 1.6.1 Attachment to 25:1 Polymer 300 mg of polymer was dissolved in 5 ml DMF. 100 mg of derivatised polymyxin was added and the solution was stirred for 48 hours. The solution was poured into 100 ml of water together 10 ml 20% aqueous pipiridine to cleave the protecting FMOC groups. The polymer was purified by ultrafiltration and freeze dried to give a pink solid.

1.6.2 Attachment to 45:1 Polymer 250 mg of polymer was dissolved in 5 ml DMF. 75 mg of derivatised polymyxin was added and the solution was stirred for 48 hours. The solution was poured into 100 ml of water together 9 ml 20% aqueous pipiridine to cleave the protecting FMOC groups. The polymer was purified by ultrafiltration and freeze dried to give a pink solid.

1.6.3 Attachment without FMOC

Attachment was carried out without FMOC protection, at low pH and under dilute conditions.

2. Immobilisation of Synthesised Copolymers in Polyurethane Material 2.1 Generation of HBPNIPAM/Vancomycin/Nile Red Immobilised PU Foam Materials PNIPAM/Nile Red/van (1.5 above)

Hypol 2002 (isocyanate solution): Batch no 21.8.12 (Smith & Nephew)

Brij solution: Batch no 21.8.12 (Smith & Nephew)

THF: Batch no STBD2989V (Sigma)

2.1.1 Method

Step 1. Hypol 2002 (batch no. 21.8.1, stored at 38 C, 10 g) was weighed into a small 60 ml plastic container and PNIPAM/Nile Red polymer (0.5 g, powder or dissolved in THF 5 ml) was added and mixed thoroughly, and then placed in the incubator for approximately 5 minutes.

Step 2. The aqueous phase (Brij solution) was weighed (8.5 g) into a small 60 ml plastic pot.

Step 3. The Hypol/polymer mix was removed from the incubator and the aqueous phase immediately added, and the mixture stirred rapidly with a spatula, until the two phases had created a creamy emulsion (approximately 10-15 seconds).

Step 4. The emulsion was poured into a clean 60 ml container and allowed to foam.

Step 5. After approximately 15 minutes once the foam had cured to a non-tacky elastomeric foam, it was removed from the container and dried at 40-50 C overnight in a vacuum oven set at 20 mbar.

2.1.2 Method

Steps 1-5 of Method 2.1.1 were followed with the following adaptation:

Step 1. Hypol (5 g) placed in an incubator.

Step 2. Brij (5 g), PEG 3400 (40 mg) and PNIPAM/Nile Red vancomycin copolymer (0.25 g) mixed together and placed in fridge to cool.

Step 3-5 as Method 2.1.1.

Steps 1 to 5 of the above Methods were repeated using the following quantities of HB-PNIPAM sample polymers, Hypol and aqueous phase:

| Foam | Sample/g | Hypol/g | Aqueous phase/g |
|---|---|---|---|
| 2.1.1.1 | 1.5/0.28 | 5 | 4.25 |
| 2.1.1.2 | 1.5/0.29 | 5 | 4.25 |
| 2.1.1.3 | 1.5.2/0.5 | 5 | 5 (+40 mg PEG3400) |
| 2.1.1.4 | 1.5.2/0.2 | 5 | 5 (+40 mg PEG3400) |
| 2.1.1.5 | 1.6.3/0.2 | 5 | 4.5 (+10 mg PEG 3400) |
| 2.1.1.6 | 1.5.6.1/0.2 | 5 | 4.5 (+10 mg PEG 3400) |
| 2.1.2.1 | 1.5.2/0.25 | 5 | 5 (+40 mg PEG3400) |

In all cases and in all subsequent immobilisations, the copolymer was incorporated without affecting the foaming reaction. Good quality foams were obtained with uniform pink colour or (2.1.1.6—Dansyl) cream colour, showing the dye evenly dispersed in the foam.

2.2 Generation of HBPNIPAM/Vancomycin/Nile Red Immobilised PU Film

Materials

Materials

HBPNIPAM/Nile Red/van (1.5 above)

Hypol 2002(isocyanate solution): Batch no 857370(Smith & Nephew)

THF (Sigma Aldrich Batch no STBB0055H9)

Tin octoate Sigma Aldrich Batch no SLBC8056V

Butane diol Sigma Aldrich Batch no STBF1852V

2.2.1 Method

Step 1. Hypol (5 g) heated to 40 C for ease of handling and tin octoate (0.5 ml) were dissolved in THF (40 ml). Butane diol (0.227 g) in THF (10 ml) was added and the solution refluxed for 5 hours.

Step 2. HBPNIPAM/Nile Red polymer (0.5 g, dissolved in water/THF (1 ml/2 ml) was added to the HYPOL/butane diol solution and refluxed for a further hour.

Step 3. The Hypol/polymer solution was allowed to cool.

Step 4. The cooled Hypol/polymer solution was poured onto siliconized release paper.

Step 5. Solvent was allowed to evaporate. The resulting film was washed using established procedure.

2.2.1 Results

A pink colored film was obtained. Further extraction produced clear washings indicating that PNIPAM was successfully immobilised in the film.

2.3 Generation of HBPNIPAM/Vancomycin/Nile Red Immobilised PU Xerogel Adhesive Materials As 2.2 above

2.3.1 Method

Step Pre 1. Generation of Prepolymer: A polyoxyethylene—polyoxypropylene diol monobutyl ether, which has a ratio of polyoxyethylene to polyoxypropylene residues of 1:1 and molecular weight of 4095 {300 g, 0.073 moles based on OH value) and a polymericmethylene diphenyldiisocyanate (3721 g, 0.266 moles, —NCO functionality of 2.7) were mixed together at an NCO/OH ratio of 2.5 in a 700 cm$^3$ flange flask fitted with an overhead stirrer.

The flask was heated in a waterbath set to a temperature of 90° C.

A catalyst comprising dibutyltindilaurate {0.2% w/w) was added. The mixture was stirred at 90° C. for two hours.

The prepolymer so formed was allowed to cool. The prepolymer was a golden yellow viscous liquid which may be stored in a capped bottle until ready for use.

The prepolymer was found to have an isocyanate content of 1.98%.

Step 1. HBPNIPAM/Nile Red polymer is dissolved in prepolymer from Step Pre 1, used in place of HYPOL of Method 2.1.1.

Steps 2-3 of Method 2.1.1 and Steps 4-5 of Method 2.2.1 are followed with the following adaptation:

Step 2 of Method 2.1.1. A glycol used in place of the Brij solution. A portion of the prepolymer and the calculated quantity of glycol which would react with all the available isocyanate are mixed at room temperature until homogeneous.

Step 3 as Method 2.1.1.

Step 4 as Method 2.2.1. The prepolymer PNIPAM diethylene glycol then spread onto a silicone release paper at a weight per unit area of 280 gsm and cured at 90° C. to give an adhesive mass.

Step 5 as Method 2.2.1. The adhesive mass contains 85% by weight of water when fully hydrated.

A pre cast film of a thermoplastic polyether polyurethane may be transfer coated onto the adhesive mass. and the laminate strip so formed cut into pieces which are suitable for adhesive dressings and packed in a bacteria proof and waterproof package and sterilised by irradiation.

2.3.2 Method

Step 1 as Method 2.3.1 except that polyoxyethylene/polyoxyproylene glycol is reacted with Desmodur N100, a solvent free aliphatic polyisocyanate, essentially 3 functional, in a molar ratio of 2:1 to form a prepolymer.

3. Immobilisation and Extraction Studies; Hydrophilic Response and Sterilisation Aim: This example shows the immobilisation of branched polymer in the polyurethane network. The hydrophobic response of the immobilised branched polymer was maintained as evidenced by change in Nile red coloration in different solutions. 5 washings were found to be effective in removing residual non-bound polymer. UV and compiled peak wavelengths of aqueous EtOH and pure EtOH washings of HBPNIPAM polymers immobilised in foam (eg ALLEVYN foam) were analysed.

Example 3.1/Solvent Extraction Aqueous Ethanol

Three polymers produced by the above methodology were incorporated into foam during the foaming process. These foams were then washed and the washing solution analysed to determine if any of the polymers had leached out of the foam. The foams were also tested in different hydrophilic environments to determine the effect of hydrophobicity on the foams.

Samples
3.1.1 HBPNIPAM/Nile red copolymer immobilised PU foam, RAFT agent still attached
3.1.2 HBPNIPAM polymer immobilised PU foam, RAFT agent removed to give carboxyl functionality contains, fluorescent tag
3.1.3 HBPNIPAM polymer immobilised PU foam, RAFT agent removed to give carboxyl functionality Aqueous/Ethanolic Extracts of Polymer Foams
1. Samples of each of the foams (0.5 g) were placed in plastic containers (60 ml) and 5% aqueous ethanol (20 ml) added
2. The mixture was agitated using an orbital shaker and left for 2 hours
3. The foams were removed from the liquid and squeezed to release as much solution as possible
4. The extracted solution were then tested using UV spectral analysis, the following samples were analysed Control foam was made and washed in addition to the polymer foams. The UV spectra of the washes from the control foam gave an indication of any residues that are washed out of standard foams, and can be used to determine any differences seen with the polymer foams wash spectra. The UV spectra showed washes 1 and 2 carried out using 5% aqueous ethanol and a wash carried out in ethanol. All three spectra for the control foam had a peak with a maxima between 284.49 nm and 285.48 nm, hence for any foam that was washed in these conditions a peak in or close to this region would be expected.

The polymer was successfully immobilised into foam and only a small amount of the appeared to wash out. The polymers 1.3.2 and 1.3.3 were also successfully immobilised into foam and only small amounts of these were washed out, as seen from UV spectra.

Results Hydrophobic and Hydrophilic Response of Nile Red Polymer and Nile Red Polymer Foam The Nile red polymer sample 3.1.1 was placed in deionised water and THF to give the two different environments for the polymer to respond the hydrophobicity. The Nile red in the water responded by having a purple/pink colouration and the Nile red in the THF gave a pink/orange slightly fluorescent solution. This indicates that the Nile red still reacts to changes in the degree of hydrophobicity while co-polymerised with NIPAM. The polymer was also put into ethanol and acetone to show the colour spectrum in different degrees of hydrophobicity, with ethanol being the least hydrophobic and THF being the most hydrophobic environment. This can be seen in FIG. 3.1 (a).

The foam 3.1.1 was placed in both water and THF and an image of these pieces of foam can be seen in FIG. 3.1 (b). The foam in water has a purple/blue colour and the foam in the THF has a pink/orange colour, showing that the Nile red polymer is still reactive to different hydrophobicity environments when incorporated/immobilised into the foam.

Example 3.2/Immobilisation of Foams

Samples
3.2.1 HBPNIPAM/Vancomycin/NR Copolymer Immobilised Foam

UV of aqueous EtOH washings of Allevyn/HBPNIPAM NR vancomycin showed the immobilisation of vancomycin functionalised polymer. 5 washings were found to be effective in removing residual non-bound polymer (standard protocol).

Example 3.3/Solvent Extraction Aqueous Ethanol

The determination of whether HBPNIPAM/Vancomycin copolymer and HBPNIPAM/Polymyxin copolymer had become immobilised in Allevyn type foam was determined by IR analysis.

1 Method
Sample 3.3.1 HBPNIPAM/Vancomycin Copolymer
1. Hypol (5.13 g) was weighed into a plastic 100 ml beaker and HBPNIPAM/Vancomycin copolymer (0.25 g) was added and they were mixed together thoroughly
2. The mixture was placed in an incubator so that its temperature would reach 38° C.
3. Once the mix was at 38° C. the Brij suspension (4.25 g at 5° C.) was added and the entire mixture was agitated vigorously for 5-6 seconds and then poured into a fresh beaker and allowed to rise
4. After approximately 10 minutes the foam had cured and was removed from the beaker and dried in an oven overnight (50° C., 48 hours)

Sample 3.3.2 HBPNIPAM/Polymyxin Copolymer
The method was as detailed above. The following quantities were used.

| HBPNIPAM/Polymyxin copolymer | 0.26 g |
| Hypol | 5.12 g |
| Brij suspension | 4.25 g |

The exhaustive washing of both foams was carried out as in the standard protocol.

The IR results for the two different foams were compared to the control foam and reference spectra for 3.3.1 and 3.3.2. It was seen that there are few differences in the IR spectra for the HBPNIPAM/Vancomycin copolymer foam than to the standard foam. At wavelength numbers 1650 and 1375 cm$^{-1}$ there were some additional peaks apparent for the HBPNIPAM/Vancomycin copolymer foam these would be in similar places to peaks from the HBPNIPAM/Vancomycin copolymer IR reference. This would suggest that the HBPNIPAM/Vancomycin copolymer had become entrapped within the foam. Stacked plots showed the HBPNIPAM/Vancomycin copolymer foam IR with the IR of the foam reference subtracted; when compared with the HBPNIPAM/Vancomycin copolymer reference it could clearly be seen that some HBPNIPAM/Vancomycin copolymer had become entrapped within the foam (emphasised by overlay plots).

The HBPNIPAM/Polymyxin copolymer foam was evaluated further using a light microscope (FIG. 3.3) from which it could be seen that a few strands of the HBPNIPAM/Polymyxin copolymer Sample 3.3.2 were encapsulated within the foam.

A piece of each foam was also exhaustively washed and UV run on each of the washing solutions. It could be seen that for both foams all residues were washed out by the fifth wash, meaning any remaining polymer was entrapped within the foam.

Example 3.4/Solvent Extraction Aqueous Ethanol

Samples
3.4.1 HBPNIPAM/Vancomycin/Nile Red (15:1, NIPAM:RAFT) Immobilised Foam
3.4.2 HBPNIPAM/Vancomycin/Nile Red (25:1, NIPAM:RAFT) Immobilised Foam
3.4.3 HBPNIPAM/Vancomycin/Nile Red (45:1, NIPAM:RAFT) Immobilised Foam The determination of whether there has been immobilisation of HBPNIPAM/Vancomycin into Allevyn type foam was determined by IP analysis and UV of washing solutions of the foams.

For the control foam the peak of interest is around 284-285 nm, although the lambda max shifts as the absorbency intensity decreases. It can be seen that with every wash the peak is decreasing in height (/intensity), showing that by wash 5 practically all residues have been washed away from the foam. Results for the HBPNIPAM/Vancomycin/Nile red immobilised foams show that although the peaks of interest start off more intense than with the control foam they are all practically gone by wash 5 for each foam, again showing that all the residue is washed away by wash 5.

IR spectra show a few key differences between the control foam and the foams with immobilised polymer. The most obvious difference is at 1650 cm$^{-1}$, which indicates that the more the ratio of NIPAM: RAFT increases the less polymer appears to be immobilised in the foam. There is also a difference in the IR spectra at 1380 cm$^{-1}$. These differences in the in the IR spectra show that the Vancomycin polymer has become immobilised within the foam.

Example 3.5/Immobilisation of Polymers

Samples
3.5.1 Control foam
3.5.2 HBPNIPAM/Polymyxin copolymer (45:1 NIPAM:RAFT) immobilised foam
3.5.3 HBPNIPAM/Polymyxin copolymer (25:1 NIPAM:RAFT) immobilised foam
3.5.4 HBPNIPAM/Nile red extended outer shell Vancomycin copolymer (15:1 NIPAM:RAFT) immobilised foam
3.5.5 Linear PNIPAM/Vancomycin copolymer (25:1 NIPAM:VBA) immobilised foam
3.5.6 Linear PNIPAM/Vancomycin copolymer (20:1 NIPAM:VBA) immobilised foam All of the samples were washed with 5% aqueous ethanol and UV spectra taken of the washings to determine when the extractable residues had been removed from the foams. It can be seen from the spectra that for each foam by the fifth wash practically all the residues had been washed out. From the spectra there appeared to be no additional residues removed from the functional test foams than there has been from the control foam.

The washed foams were also analysed by IR.

Samples 3.5.2 and 3.5.3 both contained an immobilized copolymer that contained Polymyxin. The IR spectra for these foams and the control foam were compared.

In addition the spectra for sample 3.5.3 (Polymyxin PNIPAM immobilized foam) with the spectra for the control foam subtracted, showing what is truly entrapped within the foam. The peaks for this spectrum correspond to those for the reference Polymyxin and PNIPAM polymer (Farapak), indicating that the functional polymer is entrapped.

Spectra were compared for the foams that have Vancomycin functional PNIPAMs incorporated during the foaming process. When compared to the control there is increased signal at 3600-3200 cm$^{-1}$, at 1650 cm$^{-1}$ and 1375 cm$^{-1}$ indicating that the functional PNIPAM has become entrapped within the foam. This is further indicated by looking at comparison spectra for which the control has been subtracted from sample 3.5.5 showing the remaining peaks correspond with those from the reference Vancomycin and reference polymer (Farapak) spectra. This means there is functional PNIPAM within the foam.

Finally the IR spectra of Vancomycin PNIPAM foam samples 3.4.1 to 3.4.3 above were compared to the 3.5.4-6 Vancomycin PNIPAM foams which appear to have a stronger signal at 1650 cm$^{-1}$, possibly meaning that a more concentrated amount of Vancomycin PNIPAM has become entrapped within the foam.

Example 3.6/Solvent Extraction Aqueous Ethanol; Sterilisation

Samples
3.6.1 HBPNIPAM/Vancomycin copolymer (25:1 NIPAM:RAFT) immobilised in polyurethane foam
3.6.2 HBPNIPAM/Polymyxin copolymer (25:1 NIPAM:RAFT) immobilised in polyurethane foam
3.6.3 Linear PNIPAM/Vancomycin copolymer (25:1 NIPAM:VBA) immobilised in polyurethane foam A piece of each of the three sample foams was subject to gamma sterilisation, with another sent to ETOX sterilisation and a third piece kept as a non-sterile comparison. For all three foams it could be seen that sterilisation had no visible effect on the sample colour.

Example

Small pieces of the foam were then placed into a 5% aqueous ethanol solution and acetone; the aqueous ethanol represents a more hydrophilic environment and the acetone a more hydrophobic environment. The hydrophilic environment represents the environment the polymer would be exposed to when there are no bacteria around and the branches of the polymer are open as they would be surrounded by water molecules. The hydrophobic environment is representative of when the polymer is in the presence of bacteria and water molecules are no longer surrounding each branch of the polymer and these branches curl up on themselves.

The foam in ethanol has a purple colour and the foam in acetone has a pink colour, showing that the Nile red polymer is still reactive to different hydrophobicity environments when incorporated/immobilised into the foam.

The linear Vancomycin polymer foam sample 3.6.3 was then examined; the ETOX sterilised samples showed that in two different environments a clear difference in colour is observed with the hydrophilic aqueous ethanol environment causing a purple colour and the hydrophobic acetone environment causing a pink colour. With the gamma sterilised samples the colour changes still occur and appear as strong as for the ETOX samples.

For the ETOX sterilised samples in the two different environments a clear difference in colour was observed with the hydrophilic aqueous ethanol environment causing a purple colour and the hydrophobic acetone environment causing a pink colour with all samples. With the gamma sterilised samples the colour changes still occurred but were not quite as strong as for the ETOX samples.

For the gamma sterilised linear Vancomycin polymer foam sample 3.6.3 the colour changes still occurred and appeared as strong as for the ETOX samples.

Example 3.7—Solvent Extraction Ethanol, Acetone, Dichloromethane

Observation of red coloration of solvent washings and change in red coloration of foams for a number of foams washed in solvents EtOH, acetone, CH2Cl2
25:1 HBPNIPAM/NR/Van/Polymyxin immobilised foam
45:1 HBPNIPAM/NR/Polymyxin immobilised foam (slightly paler and therefore further investigated)
25:1 HBPNIPAM/NR/VAN/Polymyxin immobilised foam (appears unchanged and is representative of no colour change observed with all the other samples).

Tables 1 and 2 show observations of each of the solvents post extraction indicating whether they were clear or coloured. The findings are that all of the samples are clear except for the 45:1 HBPNIPAM/NR/Polymyxin foam which had a pink colouration for all extracting solvents and 45:1 HBPNIPAM/NR/Van foam ethanol extract which was only very slightly pink colour.

An extended extraction was therefore carried out for the 45:1 HBPNIPAM/NR/Polymyxin foam with ethanol for 2 hours then replacing the solvent with fresh ethanol and extracting for another 2 hours so a total of 4 hours extraction. The ethanol after 2 hours was pink coloured as anticipated but the ethanol used for the subsequent 2 hours was clear indicating that no more material could be leached from the foam. In addition an extended extraction over 2 hours with dichloromethane resulted in the foam still retaining a pink colour with the solvent also taking on a pink colour. Continued washing of this foam with fresh solvent was not carried out, as it was anticipated to also show clear after 4 hours.

Therefore the PNIPAM polymers are quite firmly held within the foam structure. Material extracted from the 45:1 polymer samples is attributed to a greater amount of residual material which would be removed on work up as hereinbefore defined. All foams after extraction including those that were extracted for longer lengths of time remain pink indicating that not all polymer is removed.

TABLE 1

Solvent extraction of PNIPAM/Foam Composites

| Sample Foam | Wt (g) | Ethanol | Wt (g) | Acetone | Wt (g) | CH$_2$Cl$_2$ |
|---|---|---|---|---|---|---|
| 25:1* HBPNIPAM/NR/Van | 0.28 | Clear | 0.23 | Clear | 0.23 | Clear |
| 15:1 HBPNIPAM/NR/Vancomycin | 0.13 | Clear | 0.16 | Clear | 0.12 | Clear |
| 45:1 HBPNIPAM/NR/Vancomycin | 0.16 | Very slightly pink | 0.14 | Clear | 0.15 | Clear |
| 25:1 HBPNIPAM/NR/Polymyxin | 0.13 | Clear | 0.13 | Clear | 0.14 | |
| 45:1 HBPNIPAM/NR/Polymyxin | 0.13 | Pink | 0.12 | Pink | 0.12 | Pink |
| HBPNIPAM/NR/Vancomycin/Polymyxin | 0.14 | Clear | 0.15 | Clear | 0.13 | Clear |

*Wt (g) DMSO Clear

TABLE 2

Solvent extraction of various PNIPAM/Foam Composites

| Sample Foam | Wt (g) | 2 Hr Ethanol Extract | 4 Hr Ethanol Extract | Wt (g) |
|---|---|---|---|---|
| 45:1 HBPNIPAM/NR/Polymyxin** | 0.23 | Pink | Clear | 0.24 |

**2 Hr CH$_2$Cl$_2$ extract pink

Example 3.8 Retention of Polymer in PU Shown by Fluorescence Detection Using LED Powered MLD Device Aim To investigate the retention of P-NIPAM/van/nile red polymers when made into a polyurethane foam dressing.

Materials

25:1 P-NIPAM/van/NR (4% wt in PU foam prepared by the method of Example 2.1.1 and 10% wt in PU foam prepared by the method of Example 2.1.2)

Methods

Images of foam and film dressings were taken using an interfacing device (Excitation with a 580 nm LED array and emission measured with a 647±5 nm band pass filter).

25:1 P-NIPAM/van nile red polyurethane foam were imaged with the device then washed five times in 5% aqueous ethanol. Following the washes the foam was imaged again with the device.

Results

No difference was seen post washing in the fluorescence of the 25:1 P-NIPAM/van nile red (10% wt) foam.

The corresponding 25:1 P-NIPAM van/NR foam (4% wt) following washing showed excellent retention of polymer as shown in FIG. 3.8. This example clearly shows the retention of polymer in the foam Increased loading of the foam (4% to 10%) with 25:1 P-NIPAM/van/NR polymer resulted in enhanced fluorescence when imaged, as illustrated in FIG. 3.8 (*b*)

Example 4

Example 4.1 Polymer Distribution in Polyurethane Foam

Aim

To investigate the distribution of P-NIPAM/van nile red polymer when added to polyurethane foam.

Materials

25:1 P-NIPAM/van/NR (4% wt polymer in PU foam prepared by the method of Example 2.1.1)

Methods

25:1 P-NIPAM/van nile red polyurethane foam was embedded in paraffin wax and 4 μm sections were cut using a microtome. The section was then mounted on a microscope slide. Fluorescence within the foam was visualised using an inverted fluorescent microscope.

Results

Nile red fluorescence (shown as white in FIG. 4.1) could be seen throughout the histological section of polyurethane foam, however no fluorescence was seen within the voids or pores of the foam section.

Example 4.2 Fluorescence Detection of Polymer in PU Foam Using LED Powered Device Images of foam were taken using a fluorescence excitation and imaging device (Excitation with a 580 nm LED array and emission measured with a 647±5 nm band pass filter).

4.2.1 Thermal Response of Polymer

Aim

To investigate the fluorescent properties of P-NIPAM/van nile red polymers when made into a polyurethane foam or film dressing.

Materials

25:1 P-NIPAM/van/NR (4% wt polymer in PU foam prepared by the method of Example 2.1.1

Methods

Images were taken of foam dressings at various temperatures and post washing 5× with 5% aqueous ethanol.

Results

25:1 P-NIPAM/van nile red polymer in polyurethane foam was incubated at 4° C., room temperature, and 50° C. alongside polyurethane foam without polymer (Control). The foam was then imaged using the excitation and imaging device and an increase in fluorescence saturation (blue pixels) could be clearly seen when increasing temperature. This result suggested that the polymer was still capable of undergoing a thermoresponsive coil-to-globule transition Results are Shown in FIG. 4.2.1

Example 4.2.2 Fluorescent Activity of Dressing Comprising Polymer in PU Foam Supported on Adhesive Film Aim To investigate the ability to detect fluorescence of P-NIPAM/van/nile red polymers when made into a polyurethane foam dressing.

Materials

Island Dressing comprising 25:1 P-NIPAM/van/NR in PU foam (prepared by the method of Example 2.1.1) supported on OPSITE adhesive film Methods The material was imaged Results The results in FIG. 4.2.2 show excellent imaging of fluorescence of the material.

Example 4.4 Binding of Bacteria by Polymer in PU Film Shown by Fluorescence Detection Aim To investigate the binding of bacteria by P-NIPAM/van/nile red polymers when made into a polyurethane film dressing.

Materials

25:1 P-NIPAM/COOH/NR (polymer in PU film)

Methods

25:1 P-NIPAM/COOH nile red polymer (1.5.2) was cast into a polyurethane film. Using the interfacing device it was possible to image the fluorescence from nile red and this appeared to show some increase with temperature. Fluorescence was also measured over 30 minutes as the temperature of the film was increased from 4° C. to 42° C. using a fluorescent plate reader as described above.

Results

This result shown in FIG. 4.4 suggests that the polymer within the film is thermoresponsive and capable of undergoing a coil-to-globule transition.

Example 5—Bacterial Binding and Indication 5.1 Selective Binding of Bacteria (by Gram Type) by Polymer (by Degree of Branching) in PU Shown by Fluorescence Detection Aim To investigate the binding of bacteria by P-NIPAM/van/nile red polymers when made into a polyurethane foam dressing.

Materials

25:1 P-NIPAM/van/NR (polymer in PU foam prepared by the method of Example 2.1.1) 15:1 P-NIPAM/van/NR (polymer in PU foam prepared by the method of Example 2.1.1) Linear extended P-NIPAM/van/NR (polymer in PU foam prepared by the method of Example 2.1.1)

Hyperbranched extended P-NIPAM/van/NR (polymer in PU foam prepared by the method of Example 2.1.1)

Methods

25:1, 15:1, Linear-Extended, and Hyperbranched-Extended P-NIPAM/van nile red polyurethane foam samples were cultured with either PBS, *S. aureus* or *P. aeruginosa* for 30 minutes. Fluorescent readings were taken using a Tecan M200 plate reader every 60 seconds. Foam fluorescence varied substantially at the beginning of the experiment due to variation in thickness and porosity and therefor fold change in fluorescence between 2 minutes and 15 minutes was used to determine if an effective response to *S. aureus* had occurred.

Results

25:1, 15:1 and HB-ext P-NIPAM/van nile red foam dressings had a positive fold change when cultured with *S. aureus* but not *P. aeruginosa*, suggesting that these dressings are responding to the bacteria in a similar manner to the soluble polymer.

Example 5.2 Bacterial Growth Inhibition

Aim

To test whether P-NIPAM/van nile red polymer is bactericidal

To demonstrate that P-NIPAM/van nile red polymer does not release van

Materials

25:1 P-NIPAM/van/NR (prepared by the method of Example 2.1.1)

Method

*S. aureus* was spread on a brain heart infusion agar plate (1) so as to cover the entire plate with a lawn of bacteria (2). Three 10 µl drops of vancomycin (1 mg/ml) (4) were dispensed on one side of the plate as a positive control for bacterial inhibition and three 10 µl drops of 25:1 P-NIPAM/van nile red polymer after washing (3) were added to the plate on the other side. The plate was then incubated at 37° C. overnight.

Results

Following overnight incubation, growth inhibition of *S. aureus* was clearly visible where the drops of vancomycin (4) had been placed whereas there was no visible growth inhibition from the drops of 25:1 P-NIPAM/van nile red polymer (3).

The results are shown in FIG. 5.2 illustrating agar plate (1) having lawn of bacteria (2) with drops of vancomycin (4) and drops of 25:1 P-NIPAM/van nile red polymer after washing (3).

Example 5.3 Non Bactericidal Activity of Polymer in PU Foam Shown by Bacterial Recovery after Binding Aim To investigate the non-bactericidal activity of polymer in PU foam by recovery of live bacteria after binding by P-NIPAM/van/nile red polymers when made into a polyurethane foam dressing.

Materials

25:1 P-NIPAM/van/NR (polymer in PU foam prepared by the method of Example 2.11.)

Methods

Additional graphs/images

Results

FIG. 5.3 shows recovery of bacteria from 15:1 P-NIPAM/van corresponding to that from PBS. The polymer in foam is concluded to be non-bactericidal.

EXAMPLE 5.4 Binding of Bacteria by Polymer in PU Shown by Fluorescence Detection Aim To investigate the binding of bacteria by P-NIPAM/van/nile red polymers when made into a polyurethane foam dressing.

Materials

25:1 P-NIPAM/van/NR (polymer in PU foam prepared by the method of Example 2.1.1)

Methods

Binding of *S. aureus* to 25:1 P-NIPAM/van nile red polyurethane foam was evaluated following a 24 hour incubation of bacteria with foam at 37° C. Foam was then embedded in paraffin wax and 4 µm sections were cut using a microtome. The sections were mounted on a microscope slide and xylene was used to remove the wax. The sections were then Gram stained to highlight bacteria. Sections were imaged using an upright brightfield microscope with a 20× magnification lens.

Results

The Results are illustrated in FIG. 5.4. Vast amounts of *S. aureus* (dark violet cocci) could be seen attached to the foam, particularly on the edges Example 5.5—Gram Staining of Foams Incubated with Bacteria Aim To investigate the selective binding of gram positive and gram negative bacteria by P-NIPAM/van/nile red and P-NIPAM/poly/nile red polymers when made into a polyurethane foam dressing.

Materials

P-NIPAM/van/NR (polymer in PU foam prepared by the method of Example 2.1.1)

Methods

Using the method of Example 5.4

Vancomycin-HB-PNIPAM based polymer and the Polymyxin-HB-PNIPAM based polymer have both been incorporated into polyurethane foam, which can easily be incorporated into any foam based dressing.

Results

The two polymers have been shown to react differently to gram positive and gram negative bacteria. Example images can be seen in FIG. 5.5.1 to FIG. 5.5.4, where FIG. 5.5.1 shows a gram stain of the control foam (no polymer present) with staph aureus (gram positive bacterium). FIG. 5.5.2 shows the Vancomycin nile red polymer immobilised in foam in PBS (phosphate buffer solution), FIG. 5.5.3 the foam has been incubated with Pseudomonas aeruginosa (gram negative bacteria) it can be seen that there is no difference between FIG. 5.5.2 and FIG. 5.5.3, meaning there has been no capture of the bacteria onto the foam. Whereas in FIG. 5.5.4 the Vancomycin nile red polymer immobilised in foam has been incubated with Staph aureus, black particles can be seen on the foam showing that the gram positive bacteria has been captured by the polymer in the foam.

The example illustrates the advantages of the described invention, in relation to the ability to detect whether bacteria is gram positive or gram negative.

The invention claimed is:

1. A device for detecting a microbe or a pH change due to the presence of a microbe at a locus comprising a polymeric material, wherein the polymeric material comprises:
    a semi-interpenetrating network of a polyurethane and a hydrophilic polymer, wherein the hydrophilic polymer comprises a polyacrylamide or a copolymer thereof;
    a first moiety comprising an antibiotics or a derivative of antibiotics modified to be devoid of antibiotic activity configured to bind the microbe, or an acid group that becomes charged at a different pH, wherein the hydrophilic polymer is configured to change from a coiled configuration to a globular configuration in response to the binding of the microbe or the charge on the acid group;
    a second moiety as an indicator comprising a solvatochromic dye configured to change color in response to the hydrophilic polymer being changed from the coiled configuration to the globular configuration, wherein the second moiety is different from the first moiety; and
    wherein the first moiety and the second moiety are covalently bonded to the hydrophilic polymer.

2. The device of claim 1, wherein the microbe is selected from the group consisting of bacteria, yeast, fungus, and combinations thereof.

3. The device of claim 1, further comprising a locus-contacting surface, wherein the locus-contacting surface comprises the polymeric material.

4. The device of claim 1, further comprising a locus-contacting surface and an opposing non-locus-contacting surface, wherein one of the locus-contacting surface and the opposing non-locus-contacting surface comprises the polymeric material; or both of the locus-contacting surface and the opposing non-locus-contacting surface comprise the polymeric material.

5. The device of claim 1, wherein the polymeric material is fluid permeable.

6. The device of claim 1, wherein the device is configured to be activated by fluid contact.

7. The device of claim 1, wherein the hydrophilic polymer is a copolymer of a hydrophilic monomer and an indicating monomer.

8. The device of claim 1, wherein said first moiety and said second moiety are immobilised in the semi-interpenetrating network and are not leached from the device.

9. The device of claim 1, wherein the change of color is configured to indicate the detection of the microbe or the pH change due to the presence of the microbe by means of a change in fluorescence, or wavelength, or intensity thereof.

10. The device of claim 1, wherein the locus comprises an exuding or humid wound environment.

11. The device of claim 1, wherein the polymeric material is in the form of foam, or of a film, perforated film, membrane, water impermeable membrane providing moisture vapour transmission (MVT), adhesive layer or coating, sheet, block, non-woven or woven fabric, thread, ribbon or combinations thereof.

12. The device of claim 1, wherein the hydrophilic polymer comprises a polymer selected from the group consisting of polyacrylamide, polyalkyl acrylamide, polyallyl acrylamide, wherein alkyl is ethyl, propyl or butyl.

13. The device of claim 1, further comprising a wound dressing, a device for interrogation of wound fluid, a medical or dental sponge or wipe, or pH sensor.

14. The device of claim 1, further comprising an inspection or scanning device or reader configured to receive information relating to color or change in color and provide output information,
wherein the inspection or scanning device or reader comprises: interrogation means for acquiring indicating information; a processor for processing indicating information and generating output information; and a display or connectivity for a display for displaying output information.

15. A kit for detecting a microbe or a pH change due to the presence of a microbe at an wound, comprising the device of claim 14 and a reference strip providing reference information for processing information relating to color and change in color and generating detection information.

16. A method for detecting a microbe or a pH change due to the presence of a microbe at a locus comprising:
providing the device of claim 1;
applying the device of claim 1 in or on the locus; and
detecting a change in color of the polymeric material.

17. The method of claim 16, wherein detecting the change in color of the polymeric material comprises providing an inspection or scanning device or reader; acquiring indication information for processing; and displaying or transmitting for display output information.

18. The method of claim 16, further comprising quantifying or classifying the change in color.

19. A method for detecting a microbe or a pH change due to the presence of a microbe, comprising:
providing a device comprising a wound contacting surface, wherein the wound contacting surface comprises a polymeric material, wherein the polymeric material comprises:
a semi-interpenetrating network of a polyurethane and a hydrophilic polymer, wherein the hydrophilic polymer comprises a polyacrylamide or a copolymer thereof:
a first moiety comprising an antibiotics or a derivative of antibiotics modified to be devoid of antibiotic activity configured to bind the microbe, or an acid group that becomes charged at a different pH, wherein the hydrophilic polymer is configured to change from a coiled configuration to a globular configuration in response to the detection of the microbe or the change on the acid group;
a second moiety as an indicator comprising a solvatochromic dye configured to change color in response to the hydrophilic polymer being changed from the coiled configuration to the globular configuration, wherein the second moiety is different from the first moiety; and
wherein the first moiety and the second moiety and the second moiety are covalently bonded to the hydrophilic polymer; applying the wound contacting surface in or on the wound; and detecting a change in color in the indicator.

20. The device of claim 1, wherein the second moiety comprises one or more selected from a group consisting of: Nile Red, Nile Blue, Dansyl cadavarine Dansyl chloride, DANSAEP, 1-hydroxy-4-[4[hydroxyethylsulphonyl)-phenylazo]-napthalene-2-sulphonate, 2-fluoro-4-[4[(2-hydroxyethanesulphonyl)-phenylazo]-6-methoxy phenol, 4-[4-(2-hydroxyethylsulphonyl)-phenylazo]-2,6-dimethoxyphenol, 4-(2-acryloyl oxyethylamino)-7-nitro-2,1,3-benzoxadiazole (NBD-AE), 4-(2-acryloylaminoethylamino)-7-nitro-2,1,3-benzodiazole (NBD-AA), 2-(6-(dimethylamino)-1,3-dioxo-1H-benzo(de)isoquinolin-2 (3H)-yl) ethyl methacrylate and derivatives and combinations thereof.

21. The device of claim 12, wherein the hydrophilic polymer comprises poly(N-isopropyl acrylamide).

22. The device of claim 1, wherein the first moiety comprises a carboxylic acid group, a succinimide group, vancomycin, polymyxin, beta-lactam, teicoplanin antibiotics, cecropin and melittin hybrid, CEME, defensins or a derivative thereof modified to be devoid of antibiotic activity.

23. The device of claim 12, wherein the hydrophilic polymer comprises poly(N-isopropyl acrylamide).

* * * * *